(12) United States Patent
Ambrose et al.

(10) Patent No.: US 8,774,435 B2
(45) Date of Patent: Jul. 8, 2014

(54) AUDIO DEVICE, SYSTEM AND METHOD

(75) Inventors: Stephen D. Ambrose, Longmont, CO (US); Samuel P. Gido, Hadley, MA (US)

(73) Assignee: Asius Technologies, LLC, Longmont, CO (US)

( * ) Notice: Subject to any disclaimer, the term of this patent is extended or adjusted under 35 U.S.C. 154(b) by 0 days.

(21) Appl. No.: 13/288,515

(22) Filed: Nov. 3, 2011

(65) Prior Publication Data

US 2012/0217087 A1 Aug. 30, 2012

Related U.S. Application Data

(63) Continuation-in-part of application No. 12/178,236, filed on Jul. 23, 2008, now Pat. No. 8,340,310, and a continuation-in-part of application No. 12/777,001, filed on May 10, 2010, now Pat. No. 8,391,534, and a continuation-in-part of application No. 13/086,138, filed on Apr. 13, 2011, and a continuation-in-part of application No. 13/222,943, filed on Aug. 31, 2011.

(60) Provisional application No. 61/409,724, filed on Nov. 3, 2010.

(51) Int. Cl.
*H04R 25/00* (2006.01)
*H04R 1/00* (2006.01)

(52) U.S. Cl.
USPC .......................................... 381/328; 381/417

(58) Field of Classification Search
USPC ........ 381/23.1, 312, 328, 380, 370–374, 381; 181/135
See application file for complete search history.

(56) References Cited

U.S. PATENT DOCUMENTS 2,876,767 A 3/1959 Wasserman
3,602,654 A * 8/1971 Victoreen ..................... 181/135
3,985,960 A 10/1976 Wallace, Jr.
4,133,984 A * 1/1979 Akiyama ..................... 381/328

(Continued)

FOREIGN PATENT DOCUMENTS

DE 2825233 A1 1/1979
DE 2913644 A1 10/1980

(Continued)

OTHER PUBLICATIONS

"Sound Fit(TM) In-Canal Sound Delivery and Custom Fit Sleeve for Bluetooth(TM) Headsets", http://ctiait.ctia.org/eTechw2009public/index.cfm?fuseaction=main.viewEntry&productID=692&start=1&subCat=5&scoreStatus=all&ct=1[Mar. 30, 2009 12:41:13 PM] E-Tech Awards 2009 Public Site 2009.

(Continued)

*Primary Examiner* — Brian Ensey
*Assistant Examiner* — Norman Yu
(74) *Attorney, Agent, or Firm* — Marvin Petry; Stites & Harbison PLLC

(57) ABSTRACT

A device and method for alleviating the effects of alternating or changing pneumatic pressures when sound is transmitted through an audio device into a substantially trapped volume to the tympanic membrane. Alternating or changing pneumatic pressures are partially or fully alleviated and allowed to remain as normal sound waves. The audio device and method could be any number of audio devices including ear buds, over-ear headphones or hearing aids. A passageway from the substantially trapped volume to an unsealed space at ambient pressure is blocked by a flexible compliant member.

55 Claims, 37 Drawing Sheets

COVERED VENT

(56) References Cited

U.S. PATENT DOCUMENTS

| | | | |
|---|---|---|---|
| 4,852,177 A | 7/1989 | Ambrose | |
| 5,483,027 A * | 1/1996 | Krause | 181/135 |
| 6,094,494 A | 7/2000 | Haroldson | |
| 6,354,990 B1 | 3/2002 | Juneau et al. | |
| D478,062 S | 8/2003 | Stephens | |
| 7,130,437 B2 | 10/2006 | Stonikas et al. | |
| 7,227,968 B2 | 6/2007 | van Halteren et al. | |
| 7,292,704 B2 | 11/2007 | Lederer | |
| 7,362,875 B2 | 4/2008 | Saxton et al. | |
| 7,425,196 B2 | 9/2008 | Jorgensen et al. | |
| 7,822,218 B2 * | 10/2010 | Van Halteren | 381/324 |
| 8,098,872 B2 * | 1/2012 | Chang | 381/371 |
| 2002/0076057 A1 | 6/2002 | Voix | |
| 2007/0116319 A1 | 5/2007 | Hagberg | |
| 2007/0270988 A1 | 11/2007 | Goldstein et al. | |
| 2008/0015463 A1 | 1/2008 | Goldstein | |
| 2008/0031475 A1 | 2/2008 | Goldstein | |
| 2008/0037797 A1 | 2/2008 | Goldstein et al. | |
| 2008/0137873 A1 | 6/2008 | Goldstein | |
| 2008/0144842 A1 | 6/2008 | Goldstein et al. | |
| 2008/0181419 A1 | 7/2008 | Goldstein et al. | |
| 2008/0181442 A1 | 7/2008 | Goldstein | |
| 2008/0187163 A1 | 8/2008 | Goldstein et al. | |
| 2008/0212787 A1 | 9/2008 | Goldstein et al. | |
| 2008/0219486 A1 | 9/2008 | Goldstein et al. | |
| 2008/0240458 A1 | 10/2008 | Goldstein | |
| 2008/0253583 A1 | 10/2008 | Goldstein et al. | |
| 2008/0299339 A1 | 12/2008 | Keady | |
| 2008/0311324 A1 | 12/2008 | Keady | |
| 2009/0007596 A1 | 1/2009 | Goldstein et al. | |
| 2009/0010442 A1 | 1/2009 | Usher et al. | |
| 2009/0012420 A1 | 1/2009 | Keller | |
| 2009/0014014 A1 | 1/2009 | Roos et al. | |
| 2009/0022294 A1 | 1/2009 | Goldstein et al. | |
| 2009/0022353 A1 | 1/2009 | Goldstein et al. | |
| 2009/0034765 A1 | 2/2009 | Boillot et al. | |
| 2009/0067661 A1 | 3/2009 | Keady et al. | |
| 2009/0071486 A1 | 3/2009 | Perez et al. | |
| 2009/0071487 A1 | 3/2009 | Keady | |
| 2009/0130423 A1 | 5/2009 | Keady | |
| 2009/0147966 A1 | 6/2009 | McIntosh et al. | |
| 2009/0155518 A1 | 6/2009 | Keady | |
| 2009/0173353 A1 | 7/2009 | Purcell et al. | |
| 2009/0192407 A1 | 7/2009 | Keady et al. | |
| 2009/0232340 A1 * | 9/2009 | Yang | 381/371 |
| 2009/0232684 A1 | 9/2009 | Hirata et al. | |
| 2010/0030131 A1 | 2/2010 | Morriss et al. | |
| 2011/0182453 A1 * | 7/2011 | Van Hal et al. | 381/328 |
| 2012/0051576 A1 * | 3/2012 | Shiomi et al. | 381/374 |
| 2012/0093331 A1 * | 4/2012 | Lin et al. | 381/71.6 |
| 2012/0103346 A1 * | 5/2012 | Keady | 128/865 |

FOREIGN PATENT DOCUMENTS

| | | | |
|---|---|---|---|
| DE | 4300804 A1 | 7/1994 | |
| DE | 10138613 A1 | 3/2003 | |
| DE | 102005016018 A1 | 10/2006 | |
| EP | 0383483 | 8/1990 | |
| EP | 0755168 A2 | 1/1997 | |
| EP | 1 272 003 A1 | 1/2003 | |
| GB | 2323295 A | 9/1998 | |
| JP | 52019905 A | 2/1977 | |
| JP | 53-030316 | 3/1978 | |
| JP | 53147526 A | 12/1978 | |
| JP | 55047713 A | 4/1980 | |
| JP | 61238198 A | 10/1986 | |
| JP | 62-002798 | 1/1987 | |
| JP | 1101794 A | 4/1989 | |
| JP | 01-269398 | 10/1989 | |
| JP | 06-047005 | 2/1994 | |
| JP | 06-077392 | 10/1994 | |
| JP | 06-35473 | 12/1994 | |
| JP | 3035669 | 1/1997 | |
| JP | 2002-320292 A | 10/2002 | |
| JP | 2004187953 A | 7/2004 | |
| JP | 2006-237783 A | 9/2006 | |
| WO | WO 86/01399 | 3/1986 | |
| WO | WO 99/31934 | 6/1999 | |
| WO | WO 99/31935 | 6/1999 | |
| WO | WO 00/08895 | 2/2000 | |
| WO | WO 01/00267 A1 | 1/2001 | |
| WO | WO 02/082788 A1 | 10/2002 | |
| WO | WO 03/005765 A2 | 1/2003 | |
| WO | WO2009/015210 A2 | 1/2009 | |
| WO | WO2009/055347 A2 | 4/2009 | |
| WO | WO-2009-125186 | 10/2009 | |

OTHER PUBLICATIONS

Compton, John, "Notes on the Diaphone", *The Organ* London, vol. 3, No. 9 Jul. 1, 1923, 42-47.

Mays, Jimmy W. et al., "Synthesis and Structure—Property Relationships for Regular Multigraph Copolymers", *Macromol. Symp.* vol. 215 2004, 111-126.

O'Brien, Jr., William D. et al., "Evaluation of Acoustic Propagation Paths into the Human Head", *New Directions for Improving Audio Effectiveness* 2005, 15-1 to 15-24.

Staudinger, U. et al., "Mechanical Properties and Hysteresis Behaviour of Multigraft Copolymers", *Macromol. Symp.* 2006, 42-50.

Tiku, Nitasha, "When his bank cut the cord, Kevin Semcken faced a tough choice: Stick to his own big plans? Or listen to his board and play it safe?", *Inc.* Jul./Aug. 2009, 58-61.

Weidisch, R. et al., "Tetrafunctional Multigraft Copolymers as Novel Thermoplastic Elastomers", *Macromolecules* vol. 34 2001, 6333-6337.

Zhu, Yuqing et al., "Morphology and Tensile Properties of Multigraft Copolymers with Regularly Spaced Tri-, Tetra-, and Hexafunctional Junction Points", *Macromolecules* vol. 39 2006, 4428-4436.

Zwislocki, Jozef, "Factors Determining the Sound Attenuation Produced by Earphone Sockets", *The Journal of the Acoustical Society of America* vol. 27, No. 1 Jan. 1, 1955, 146-154.

Zwislocki, J., "In Search of the Bone-Conduction Threshold in a Free Sound Field", *The Journal of the Acoustical Society of America* vol. 29, No. 7 Jul. 1, 1957, 795-804.

International Search Report for PCT/US2011/059137, issued Apr. 27, 2012.

International Search Report for PCT/US2011/032223, issued Feb. 8, 2012.

Supplementary European Search Report for EP Application No. EP 08 78 2266, Mar. 8, 2012.

* cited by examiner

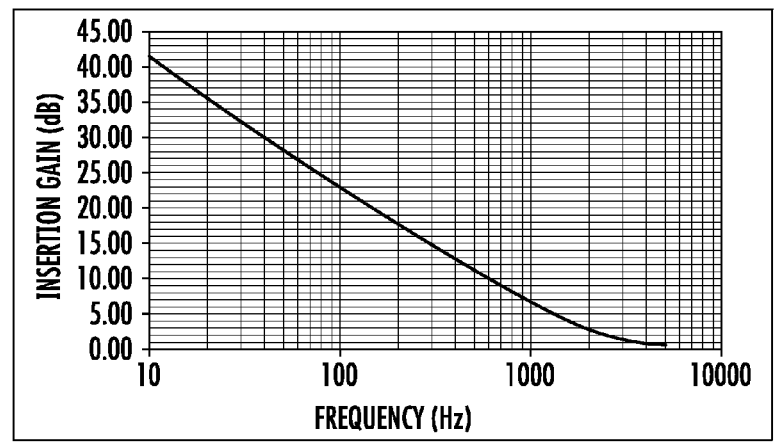
FIG. 26
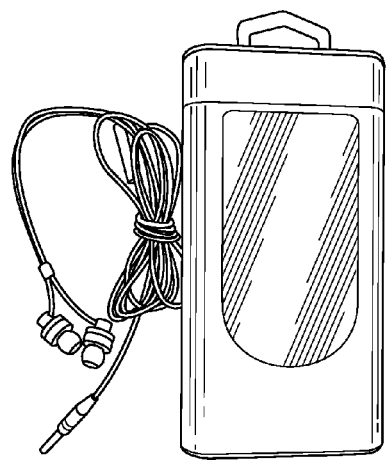
FIG. 27A
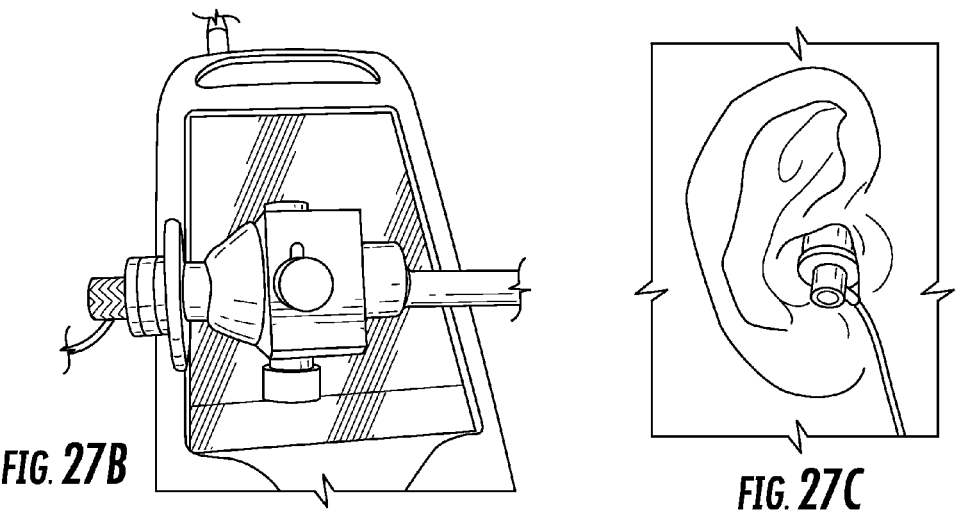
FIG. 27B
FIG. 27C

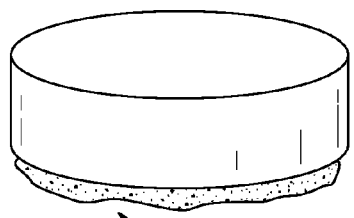
FIG. 57A   COMPLIANT MEMBRANE
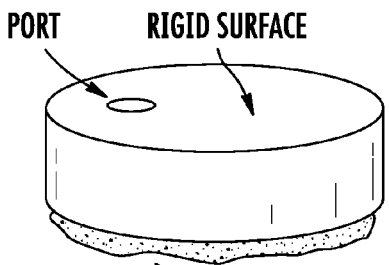
FIG. 57B   COMPLIANT MEMBRANE
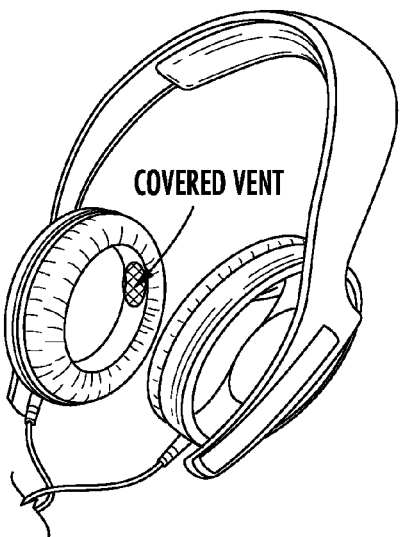
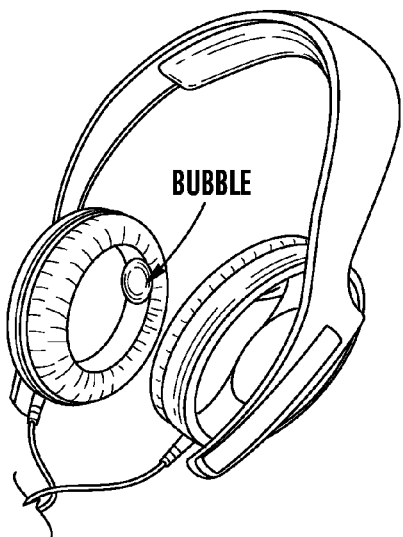
FIG. 45A                FIG. 45B EAR TIP WITH 3mm
HOLE PUNCHED

AUDIO DEVICE, SYSTEM AND METHOD

CROSS-REFERENCE TO RELATED APPLICATIONS

The present application claims filing priority to U.S. Provisional Application No. 61/409,724, dated Nov. 3, 2010. This application also claims the benefit of U.S. application Ser. No. 13/222,943, titled "Hearing Device System and Method" and filed on Aug. 31, 2011, as well as U.S. application Ser. No. 13/086,138, titled "Inflatable Bubble," filed Apr. 13, 2011. In addition, the present application is also a continuation-in-part of U.S. application Ser. No. 12/777,001, to Ambrose et al. and titled "Inflatable Ear Device," filed on May 10, 2010 and published as Publication No. 2010/0322454 A1 on Dec. 23, 2010, which is a continuation-in-part of U.S. application Ser. No. 12/178,236, to Ambrose et al. and titled "Diaphonic Acoustic Transduction Coupler and Ear Bud," filed on Jul. 23, 2008 and published as Publication No. 2009/0028356 A1 on Jan. 29, 2009. The complete content of each of the above-listed applications is hereby incorporated by reference.

TECHNICAL FIELD OF THE INVENTION

The present device, system and methods relate to the structure, operation and manufacture of an insertable sound transmission instrument for a user's ear. Specifically, the device and methods relate to such a sound delivery instrument which can be coupled with any number of electronic sound devices, such as a hearing aid, MP3 player, Bluetooth® device, computer, phone, and the like, while providing improved comfort and control to the user.

BACKGROUND OF THE INVENTION

With the invention of the professional in-ear, stage and studio, monitoring systems in the 1970's, large numbers of people began to experience the sealing of high fidelity speakers to the ear canal for the first time. These devices have protected hundreds of thousands of amateur and professional musicians and sound engineers from hearing loss due to excessive performance volumes. However, in-ear monitors have been, and remain, a persistent source of audio fatigue and potential short term or long term hearing loss. They share this problem with other in-ear listening devices such as hearing aids, insert headphones, ear buds, and the like, as well as over-ear devices. Professional applications of in-ear monitors have called for some musicians and sound engineers to tolerate conditions of persistent audio fatigue which can become nearly intolerable by the end of a performance or recording session. These users often refer to a sensation of percussiveness beating their ears, which cannot be eliminated by simply turning down the volume. The device, system and methods disclosed herein shed light on the nature of this percussiveness, and discloses inventive measures to mitigate it.

Almost every person has experienced a situation where the volume from another person's headphones could be heard even from across a room, on a bus, in a store, or any number of public venues. Given the sound volume necessary to be heard at a distance, the volume blasting directly into a listener's ear in such a situation must be excessive. The listener might be asked (or admonished) to turn down their headphones for the sake of their own health and for the courtesy to others, but what has not been hitherto widely realized is that the person listening to the headphones has already, unknowingly turned down their own personal perception of the volume through a natural hearing protection mechanism known as the "Stapedius reflex." The persistent triggering of this reflex by insert headphones, hearing aids, and the like, perpetuates a vicious cycle in which even more volume may be needed to counteract the effects of the stapedius reflex.

The persistent triggering of the stapedius reflex also sets up an additional dangerous situation: i.e., the listener, who is already tolerating very loud volumes because of the stapedius reflex, accidentally or intentionally turns the volume up even more. At this point the stapedius muscle may already have become exhausted or reached a limit of its inherent ability to protect the ear from loud sounds and temporary or even permanent hearing loss.

The following is an extensive introduction explaining the scientific basis for the previously unrealized fact that audio speakers when inserted into the human ear produce large oscillations in pressure within the ear canal, even when the speakers are operated at what would normally be considered modest outputs. These large pressures in the sealed volume of the ear canal translate into high sound pressure levels that trigger the Stapedius Reflex. The Stapedius Reflex is a natural mechanism by which the contraction of the stapedius muscle in the ear reduces the ear's sensitivity in order to protect itself from being damaged by loud noises and to widen its dynamic range to higher sound pressure levels. The resulting reduction in hearing sensitivity has the potential to diminish the quality of audio perception through insert headphones or hearing aids.

It will be shown that the acoustic, standing waves produced from a speaker in the ear canal are physically and mathematically equivalent to a static pressure, akin to the air pressure confined within an inflated balloon or the static pressure employed in tympanometry. The magnitude of this static pressure in the sealed ear canal is, unlike the static pressures normally encountered, oscillating at acoustic frequencies. This oscillating static pressure results from the trapping of a closed volume of air in the ear canal when the sound producing device is sealed in the ear. The oscillating static pressure is responsible for gross over-excursions of the tympanic membrane (ear drum) that can be one hundred, one thousand or more times greater than the normal oscillations of the ear drum associated with sound transmitted through the open air.

When sealed in the ear, the motion of the speaker diaphragm produces a set of static pressure oscillations, which are 90 degrees out of phase with equivalent open air sound waves. These static pressure oscillations in the sealed ear canal are also 90 degrees out of phase with the oscillating particle-velocity component of the waves, whereas they would be in phase with the velocity component were the waves occurring in open air. Especially at lower and midrange frequencies, the static pressure oscillations in the sealed ear canal produce a large boost in the sound volume transmitted to the tympanic membrane. Just as the open-air acoustical wave spectrum can contain the superposition of different sound waves at different frequencies, the corresponding static pressure oscillations in a sealed volume, such as the ear canal, superpose to form a spectrum of co-existing static pressure oscillations with a range of frequencies.

The large amplitude static pressure oscillations, typically associated with the lower frequency and/or greatest amplitude motions of the speaker produce an effect, which we will call Trapped Volume Insertion Gain (TVIG). TVIG is related to insertion gain as measured and used by the audio and hearing aid industries. TVIG is defined as the increase in sound pressure level (SPL), resulting from the static pressure oscillations in the ear canal across all frequencies, occurs when a speaker containing device is sealed in the ear. It is measured relative to the SPL in the ear canal when the device is held in approximately the same position at the entrance to the ear canal, but is not sealed with an air-tight seal. In this unsealed reference state, the sound waves in the ear are not equivalent to static pressures. It is shown herein that the trapped volume insertion gain of insert headphones or hearing aids is often sufficient to boost the SPL experienced by the listener above the threshold at which the stapedius reflex reduces hearing sensitivity.

It seems particularly counter-productive to have devices intended to provide high fidelity audio (insert headphones, ear buds, etc.), or aid to the hearing impaired (hearing aids) that simultaneously reduce hearing sensitivity by triggering the stapedius reflex. It is possible that trapped volume insertion gain, which is operating continuously as long as the device is sealed in the ear canal, causes the stapedius muscle to remain in a continuously clenched state. This is not a normal condition for the stapedius muscle, and it significantly contributes to and may even be the main cause of listener fatigue, in which peoples' ears begin to physically ache or hurt after prolonged use of in-ear devices.

The gross over-excursions of the tympanic membrane, produced by sealing a sound producing device in the ear, occur despite the best efforts of the clenched stapedius muscle to limit their amplitude. The trapped volume pressure, and trapped volume insertion gain, along with their influence on the stapedius reflex, have not been widely appreciated or acknowledged by audio science or industry. And, as such, their potential long term damaging impacts on human hearing have not been studied. It is hypothesized that the pressure-driven pounding may also contribute to hearing damage that popular opinion and recent study attribute to the use of in-ear listening devices.

The present application addresses the need for an in-ear listening device to lessen the impact of tympanic membrane over-excursions, oscillating static pressure in the ear canal, trapped volume insertion gain, and the constant triggering of the stapedius reflex. The inventive technology disclosed is applicable to ear buds, headphones, hearing aids, Bluetooth headsets and the like. The technology mitigates the detrimental effects of sealing a sound producing device in the ear canal by the use of an inflatable in-ear bubble-seal of the type claimed in our previous patent applications. Additionally, this application discloses a new inventive approach and a family of resultant devices that achieve the mitigation of trapped volume insertion gain, oscillating static pressure, tympanic membrane over-excursions, and the stapedius reflex in a simple and potentially inexpensive retrofit to existing in-ear devices. Both the inflatable ear seals, and the retrofit devices operate to at least partially transform the sound energy in the trapped volume in the ear canal from an oscillating static pressure back into a normal acoustic wave, which is lower in amplitude and less punishing in its effects on the ear drum, the stapedius muscle, and the ear in general.

1.1 Sound Waves in Open Air

Sound waves in open air propagate through alternating rarefactions and densifications of the gas molecules comprising the air. The propagation of sound, however, does not change the average density of the air. At any instant in time, higher pressure in densified sound wave maxima are compensated by lower pressure in rarified sound wave minima. Overall, the average air pressure remains the same. Additionally, the magnitude of sound pressure fluctuations in the open air are tiny: for instance a 100 dB sound pressure level (SPL) in air at atmospheric conditions is accompanied by a fluctuating pressure amplitude of about 5 Pa (rms average), while the atmospheric pressure itself is 101,000 Pa. Thus, this relatively loud sound is transported through air via a pressure fluctuation about twenty-thousand times smaller than the static pressure of the air itself. When a person hears sound transmitted to their open ear, through open air, these tiny, acoustic pressure fluctuations drive the motion of the tympanic membrane, and these motions are correspondingly tiny, on the order of tens to hundreds of nanometers.

1.2 Sound Generation in Open Air

When a vibrating surface (such as a speaker diaphragm) is the source of sound waves in open air, the amplitude of the oscillating pressure wave that results (i.e. the loudness) is directly proportional to the maximum transverse velocity of the surface. As with any harmonic motion, this maximum velocity occurs at the mid-point of the surface's oscillation, where displacement is zero and speed is greatest. Thus the loudness of sound from a speaker in open air is determined by how rapidly the surface can be made to move at its fastest point, not by the total amplitude of the excursions of the surface. Of course, as sound volume increases, the amplitude of speaker motion can be seen to obviously increase. In fact, for a sinusoidal profile of speaker displacement vs. time, the maximum speed of speaker motion can easily be shown to be equal to $\omega L$, where $\omega$ is the angular frequency ($2\pi$ time frequency) and L is the maximum extent of the speaker motion. This is a secondary effect, however; these large excursions are not directly responsible for the increase in sound volume. The speaker surface and its underlying electromagnetic drive are physical objects with mass and inertia, and therefore greater speed requires more distance to accelerate, and then to slow down and reverse direction at the extremes (greatest amplitude and zero velocity) of the cyclical motion. Clearly the amplitude or distance of the speaker motion, L, is not responsible for sound generation since a surface can move slowly over large distances (like picking up a speaker and carrying it across a room) without creating sound waves.

2. Speaker Sealed in the Ear Canal

When a speaker is sealed in the ear canal, creating a small trapped volume of air, the familiar physics of sound generation and sound propagation in open air is altered dramatically. If the length of this trapped volume in the ear canal is taken to be about 1 cm or less (values vary by individuals and with the type of device and depth of insertion in the ear), FIG. 1 shows the length of the trapped volume as a fraction of the wavelength of sound across the frequency range. Especially for low frequencies, but extending up into the mid-range, the trapped volume in the ear canal is only a small fraction of the wavelength of the sound.

Within this small trapped volume, only a tiny snippet at a time of an oscillating pressure profile (what would be a normal sound wave in open air) can exist. Especially for lows and mid-range frequencies, the pressure across this small trapped volume is very nearly constant because the ear canal is only sampling a small section of the "wave" at a given instant. As a result of the fact that pressure maxima can no longer coexist in time with pressure minima (as they do in open air sound waves) the average static air pressure of the system is no longer constrained to remain constant (as it is for sound wave propagation in open air). In fact, the overall pressure in the trapped volume of the ear canal can oscillate dramatically, and this results in excursions of the tympanic membrane that are orders of magnitude larger than in normal, open-ear listening.

We refer to this pressure, caused by a sealed speaker in the ear canal, as a static pressure. One reason for doing so is that this pressure bears some similarity in its effect on the ear to the static pressure applied in the diagnostic technique of tympanometry. In tympanometry, the ear canal is sealed with an insert headphone and air is pumped in and out of the sealed volume to both increase and reduce the pressure in the sealed volume relative to atmospheric pressure (and the pressure in the middle ear). This pressurization of the ear canal in tympanometry is referred to as static pressure, to distinguish it from the SPL employed in the technique, which is oscillating at acoustical frequencies, and is generally of much lower magnitude. Tellingly, it is known that the application of static pressure in the ear canal, during tympanometry can trigger the stapedius reflex. This is a non-acoustical triggering of the reflex, which must come about due to the large excursion of the tympanic membrane resulting from the pressure difference between the ear canal and the middle ear, rather than expose to a threshold SPL level. As discussed below, the static pressure induced when a headset or hearing aid with a speaker is sealed in the ear canal, has a dual character. It is simultaneously a static pressure, like the pressure produced by pumping air into the ear canal in tympanometry, and an oscillating sound pressure which can be measured as SPL. It can, therefore, potentially trigger the stapedius reflex both by its acoustical SPL and by the magnitude of its static pressure.

The static pressure in the ear canal is the pressure that results from a change in the volume (a compression or rarefaction) of a fixed amount of air trapped in the ear canal. This static pressure may, at any instant, be greater than, equal to, or less than the barometric pressure outside the ear. The static pressure may be changing (oscillating) rapidly, and thus the use of the term static may seem strange. However, the term static refers to the fact that this pressure is not a transient oscillation in pressure (i.e. a sound wave in open air) but rather is a thermodynamic, equilibrium property of the air mass associated with its volume. If the volume of this fixed mass of air is held constant (i.e. the speaker diaphragm is frozen at any point of its motion) then the static pressure will remain constant. If the volume of this air mass is changing or oscillating with the speaker motion then this thermodynamic, equilibrium property (static pressure) will also be changing or oscillating. This is true of the static pressure oscillations produced by a speaker sealed in the ear canal, provided that the rate at which pressure equilibrium is established at every incremental position of the moving speaker diaphragm is much faster than the motion of the diaphragm. The static pressure equilibrates via molecular motions that propagate across the 1 cm length of the trapped volume at the speed of sound. FIG. 2 plots the ratio of the speed of pressure equilibration vs. the peak speed of speaker motion across the frequency range. Clearly, the equilibration of pressure is much faster (thousands to hundreds of thousands of times faster) than the change in pressure resulting from speaker motion, and thus the pressure is at quasi-equilibrium, at any given instant, with respect to the influence of the moving speaker diaphragm, especially at lower frequencies.

2.1 Classical Acoustic Analysis

Beranek, analyzed case of a rigid piston oscillating in one end of a rigid tube, which is closed on the opposite end (Leo L. Beranek, Acoustics (New York: McGraw-Hill, 1954) Section 2.4, pp. 28-35). FIG. 2.3 of the Beranek reference reproduced as FIG. 3.

The analysis focuses mainly on tubes, which are long enough to set up standing wave patterns with various locations of increased and decreased pressure along the tube. However, Beranek's Equations 2.47 and 2.48 (reproduced below), which give the pressure profiles along the length of the tube, are equally applicable to very short tubes, although Beranek, himself, did not explore the implications in his book. Clearly, insert headphones that seal in the ear canal were not around in the 1950's, when Beranek did this work.

$$p(x, t) = -j_{p_0c} \sqrt{2} \, u_i e^{i\omega t} \frac{\cos k(l - x)}{\sin kl} \quad (2.47)$$

$$p = -j_{p_0 c u_0} \frac{\cos k(l - x)}{\sin kl} \quad (2.48)$$

In these equations u is the piston speed, $\rho$ is the density of air, c is the speed of sound, l is the tube length, x is the coordinate along the tube from zero at the piston's zero displacement position up to l. k is $2\pi/\lambda$, where $\lambda$ is the wavelength. The "o" subscripts on the u and $\rho$ values indicate the use of root-mean-square (rms) values and the equations then yield rms pressures. The equations, however, apply equally well to peak valves (drop the subscripts) and then give peak pressure (i.e., amplitude of the pressure oscillations). The term j is an imaginary number, also frequently known as i. Disregarding the i, which has to do with getting the correct phase of the time oscillation, Equation 2.48 gives the amplitude of the resulting pressure wave in the tube as a function of distance x, along the tube.

FIG. 4 shows the pressure profiles along a 1 cm long tube, approximating the length of the sealed, trapped volume in the ear canal calculated from Beranek's equations. The pressures plotted are the ratios of the amplitude (maximum value) of the pressures in the sealed tube divided by the pressure amplitude of the sound waves that the same piston motion would produce in open air. The pressure in the small closed tube is significantly higher than in open air, except at high frequencies. This graph shows that at an instant in time that the pressure is very uniform along the 1 cm length of the tube.

Of course the pressure is also oscillating in time. FIG. 4 shows the profile at the time when pressure is maximum. The pressure profile is equally flat with distance along the tube, but at other pressure levels, at other points in the time oscillation. As the pressure in the tube changes, these changes must propagate across the tube from the moving piston at the speed of sound. The small length of the tube, relative to the wavelength of the oscillations, however, means that the pressure profile across the tube equilibrates at each time much faster than the overall pressure level is changing with time as a result of the piston oscillations. Thus the pressure across the tube can be considered constant at any instant.

The constant pressure amplitudes across the 1 cm sealed tube length, given in FIG. 4 are quite similar to the pressures in the trapped volume of the ear canal calculated for a much more involved model taking into account the compliances and motions of the structures of the middle ear (tympanic membrane, etc.). These more realistic values are plotted in FIG. 17, below. The values in FIG. 4 are a little higher than those in FIG. 17, because the Beranek model is for a completely rigid sealed tube, with no way to mitigate the pressure increase through the motion of its surfaces.

Beranek's model of acoustical waves in a closed, rigid cylinder shows that the pressure waves produced by the oscillating piston, at one end, interfere with waves reflected off the opposite end of the tube. The resultant pressure profile in the tube is the standing wave pattern associated with the interference of this forward and reflected wave. The pressure profiles plotted in FIG. 4, resulting from this model, show that in the case where the tube is a small fraction of the wavelength of the sound, that the standing pressure waves yield a flat pressure profile across the tube. There are no nodes and antinodes of high and low pressure of the type Beranek plots in his FIG.

2.6, if the tube length is very short. The result of the interference of forward and reverse traveling waves in the closed tube also leads to a 90 degree phase shift in the pressure wave relative to the motion of the driving piston. In Beranek's analysis this phase shift is seen to be a result of the interference of a forward and a reverse traveling acoustical wave.

The fact that the pressure profile in the short tube is quasi-static and thus may be analyzed as an oscillating static pressure, rather than as an acoustic wave, can be proved by transforming Beranek's equation 2.48, in the limit of small into an expression, which is the mathematical definition of the pressure vs. volume behavior of a confined volume under static pressure. We start with a simplified version of Beranek's Equation 2.48 for the peak pressure value (pressure amplitude) as a function of distance, x, along the tube.

$$P=\rho cu \cos(k(l-x))/\sin(kl) \quad \text{(Equation 1)}$$

We recognize that when $1/\lambda$ is very small that we can employ the normal approximations to the values of the cosine and sine functions when their arguments are small. The cosine with a very small argument is very close to one, and the sine with a very small argument is well-approximated by the argument itself. The validity of these approximations is the direct mathematical cause of the flatness of the pressure profiles in FIG. 4 for frequencies up to at least 1000 Hz. With these approximations the expression for the pressure becomes:

$$P=\rho cu/(kl) \quad \text{(Equation 2)}$$

The maximum speed of the piston, u, is equal to $\omega\delta$, where $\delta$ is the maximum displacement of the piston. Substituting this into Equation 2, along with the value of k in terms of wavelength, and utilizing the relationship $c=\omega\lambda/(2\pi)$, one obtains:

$$P=\rho c^2(\delta/l) \quad \text{(Equation 3)}$$

The total volume of the tube, V, is equal to Sl, where S is the cross-sectional area of the tube. The change in volume of the tube, $\Delta V$, is equal to $S\delta$. And, therefore, $(\delta/l)$ is equal to $(\Delta V/V)$, the factor of S cancelling out of the numerator and denominator. Additionally, the fundamental definition of the speed of sound in terms of the mass and compliance of the medium in which is traveling is: $c^2=B/\rho$, where B is the bulk modulus (resistance to change in volume). Therefore:

$$P=B(\Delta V/V) \quad \text{(Equation 4)}$$

Equation 4 is the very definition of the pressure vs. volume change properties of a gas undergoing a static pressure compression or rarefaction. This has been derived, starting from an acoustical equation and imposing the limit of small tube length relative to wavelength. This proves that in this limit, we can safely analyze the case of a speaker sealed in the ear canal in terms of its static pressure effects.

A further insight links the reflection of the sound wave at the rigid back wall of the sealed tube, in Beranek's acoustical derivation, with the concept of static pressure. When the piston in the tube moves forward and compresses the gas, the rigid boundary of opposite end of the tube can either be thought of as a wall which limits the volume change of the tube at its far end, and thus enables the piston to produce a $\Delta V$, or it can be considered a hard wall boundary condition, which reflects an acoustical wave and sends a reverse wave back down the tube. The result of either analysis is exactly the same for a small tube length. Therefore, a speaker sealed in ear canal operates like pneumatic piston, producing time oscillations in overall or static pressure (analogous to barometric pressure in open air) in the trapped volume of the ear canal. These static pressure oscillations certainly do move the tympanic membrane.

When the speaker is sealed in the ear canal, the peak oscillating static pressure is determined not by the maximum speaker diaphragm speed (as in the case of open air acoustic waves) but by the maximum speaker excursion, $\delta$ in Equation 3. This is, in fact, exactly the opposite of the open air operation of the speaker. However, this is also obviously true for the sealed volume case. When a speaker diaphragm moves forward into the trapped volume of the ear canal, it reduces that volume by the product of the speaker area and the distance the speaker is moving. The speed with which this occurs is not important to the static pressure achieved in the trapped volume. But the extent of speaker motion determines the amount of volume reduction, which is directly related to the corresponding static pressure increase by the compressibility of the air (Equation 4). As discussed below, this trapped volume mechanism can lead to static pressures in the ear canal which are much larger (up to hundreds of times larger) than the sound pressures present in open air sound waves. This can trigger the stapedius reflex, thereby reducing the sensitivity of human hearing, and results in strong motions of the tympanic membrane, which are also much larger than those in normal open ear hearing.

An oscillating speaker sealed in the ear canal produces large amplitude, static pressure waves associated with the maximum displacement of speaker motion. However, the acoustical science view of what is happening, as embodied in Beranek's analysis above, indicates that acoustical pressure disturbances are simultaneously being generated and are associated with the maximum speed of the speaker diaphragm. It is the interaction of the forward and reverse traveling acoustical waves that generates the static pressure in the small confined volume, and makes the overall phenomenon appear to be related to speaker displacement and to be 90 degrees out of phase with the speaker velocity. Thus the phenomena occurring in a small trapped volume, such as the ear canal, has a dual character, somewhat akin to the wave-particle dual character of light, and fundamental physical particles. The oscillating pressure effects in the sealed ear canal are both acoustical waves and static pressure oscillations at the same time. Which of these two aspects of the phenomena is dominant, depends on the conditions. For instance, smaller confined volumes and lower frequencies (longer wavelengths) favor an oscillating-static-pressure-like behavior, while larger trapped volumes and higher frequencies favor an acoustical-wave-like behavior.

It would be convenient to define a criteria or parameter that governs whether or not sound waves in a particular medium, at a particular frequency, can be interpreted as an oscillating static pressure in a confined volume of a specific size. The most rigorous test of static pressure character is that the standing wave pressure profile calculated from Beranek's Equation 2.48 (Eqn. 1 herein) is nearly constant at every location, x, along the length of the trapped volume. This profile as calculated from the Equations will never be mathematically, exactly constant due to the nature of the mathematics employed. However, the profile can be considered functionally constant, when the calculated variations in the pressure profile are smaller than what can be measured experimentally, or alternatively are smaller than the random and transient, natural thermal fluctuations in the pressure that are always present in any system. This is equivalent to the condition that kl is very small, which is in turn equivalent to the condition that $1/\lambda$ is very small. The criterion is expressed as the ratio of the length scale associated with pressure equilibration, l, to the length scale associated with pressure variation, $\lambda$, due to sound. Exactly the same criterion can also be expressed as the ratio of the time scale of pressure equilibration in trapped volume to the time of sound wave pressure variation, or (lv/c). Here ν is the frequency.

Experimental and modeling results, to be presented below, indicate that for frequencies below about 100 Hz, a speaker sealed in the ear canal is dominated by static pressure effects, and that for frequencies greater than a few thousand Hz the behavior is predominantly acoustical. In the middle range of frequencies between these two extremes, the static pressure and acoustical behavior overlap and are both evident.

Complex audio material comprising multiple frequencies will result in multiple pressure waves of varying acoustical and static pressure character superposing in the ear canal. The lower frequencies have more of a static pressure oscillation character and the higher frequencies have more of an acoustical character. The result on the tympanic membrane, of all these sound waves, is determined by their summation under the Superposition Principle. It seems likely that the tympanic membrane undergoes large amplitude excursions, due to the oscillating static pressure character of sound waves at low frequency, while at the same time it is undergoing smaller amplitude vibrations at a range of other frequencies as a result of acoustical waves, which are also present in the ear canal.

2.2 Direct Observation of Over-Excursions of the Tympanic Membrane

Gross over-excursions of the tympanic membrane have been directly observed and video of them has been recorded using the device shown in FIG. 5. This device is a modification of a digital, pneumatic, video otoscope, an instrument a doctor uses to look into an ear canal. A commercial Apple iPod ear-bud was sealed into the insufflation port, which is a hole in the side of the device (see FIG. 5b). When the otoscope is inserted tightly into the ear canal (FIG. 5c), it produces a trapped volume and allows the tympanic membrane to be observed and filmed while music or tones are played through the ear-bud. High volume, low frequency sound played through the ear-bud (sounds which were accessed using the volume and frequency capabilities of an Apple® iPhone®) produced visible motions of the tympanic membrane, which corresponded in frequency with the output from the earbud. This was particularly discernable at the lowest frequency tested, 2 Hz, in which to tympanic membrane can readily be seen to oscillate twice per second. The same frequencies, at even much higher volumes, would not produce visible motions of the tympanic membrane for open ear hearing. Typical open-ear tympanic membrane motions of tens to hundreds of nanometers are far too small to be visible with an optical microscope. Motions of the tympanic membrane must be at least 10-100 micrometers (or 100 to 1000 times larger than normal tympanic membrane motions) to be visible with the magnifying otoscope.

Another feature that distinguishes oscillating pneumatic pressure in a trapped ear-canal volume from open air sound is directional dependence. Open-air sound, especially at higher frequencies, is louder when it is projected directly at the listener, rather than heard from the side. The transmission of open-air sound around corners is imperfect and becomes worse as frequency increases. Static pressure, of the type generated by a speaker in a sealed ear canal, is not directional. It pushes equally on all surfaces exposed to the pressure regardless of their orientation. This is the same, for instance, as hydrostatic pressure, which pushes equally on all surfaces of an object submerged under water. This difference in directional dependence between sound waves in open air and static pressure oscillations is observable with the modified otoscope device of FIG. 5. The ear-bud on the side of the otoscope is mounted at a right angle to the snout of the otoscope, which is inserted into the ear canal. Thus the ear-bud is not projecting its sound down the ear canal but transverse to the ear canal. When higher, more directionally sensitive, frequencies are played through this ear-bud, there is a marked difference in how they sound when the otoscope is sealed in the ear and when the snout of the otoscope is loosened to break the seal. When the device is not sealed the sound is not as distinct. It becomes louder, but also harsher (more percussive on the tympanic membrane), when the ear canal seal is established.

3. Modeling of a Speaker in a Trapped Ear Canal Volume 3.1 Simple Model

A very simple model, shown in FIG. 6, was analyzed mathematically to get an initial indication of the order of magnitude of responses and the general trends associated with the static pressure effects of sealing a speaker in the ear canal. This model consists of a tube of length and diameter intended to approximate the dimensions of the trapped volume in the ear canal. It is taken to be 7 mm in diameter and the length, L (the same parameter as l used in Beranek), can be varied to simulate different speaker insertion depths resulting in different trapped volume sizes. Tube lengths of 1.0 and 0.5 cm were used for illustrative calculations. One end of the tube is covered by a flexible membrane which can be displaced to simulate the motion of the speaker diaphragm. The other end of the tube is covered by a membrane with an elastic modulus equal to an average value measured for human tympanic membranes: E (Young's Modulus)=3 N/m². Both the speaker diaphragm and the tympanic membrane are assumed to have the same diameter as the tube. The pressure outside the sealed tube is initially atmospheric pressure. On the other side of the tympanic membrane is another volume, which simulates that of the middle ear. This middle ear volume is also initially at atmospheric pressure, and it has a volume of 1.5 cm³, an average value for the human population.

The computational model, as shown in FIG. 6, is very similar to an actual physical model of the ear canal used in recently reported experiments on the acoustics of insert headphones.

When the speaker diaphragm is displaced toward the trapped volume (as a hemispherical deformation), decreasing the volume, the model system distributes the effect of this disturbance between the pressurization of air in the sealed volume of the ear canal and the displacement of the tympanic membrane. The displacement of the tympanic membrane also displaces and pressurizes air in the middle ear cavity. The pressurization of the air in the ear canal and in the middle ear volume is resisted by the compressibility modulus of the air, which is derived from the Ideal Gas Law. The Ideal Gas Law is an excellent representation of the behavior of air at body temperature and near atmospheric pressure, as the compressibility factor (Z) is essentially equal to one. The stretching of the tympanic membrane, due to the pressure differential between the sealed ear canal volume and the middle ear volume, is resisted by the stretching modulus of the tympanic membrane, and is modeled as in Reference. The actual vibrational modes and extensional geometries of the tympanic membrane may be quite complex. They are simpler and more similar to the simple hemispherical deformation model used here, at lower frequencies. This modeling yields a relationship between the displacement of the tympanic membrane and the pressure difference across the membrane. Equating the pressure difference across the tympanic membrane, in terms of the pressures in the ear canal and the middle ear, to the pressure driving force for deformation of the tympanic membrane allows one to solve for both the pressure increase in the trapped volume of the ear canal and extent of deformation of the tympanic membrane.

Calculations based on this simple model were performed for a range of speaker displacements from 1 to 400 microns, and for frequencies ranging from 10 Hz to 1000 Hz. The resulting tympanic membrane displacements and pressure increases in the closed, ear canal volume were calculated. And, the pressure increase in the closed, ear canal volume was compared to the sound pressure in open air that the same speaker motion would generate. In order to perform the open air calculation, the speaker displacement and frequency were used to calculate the maximum diaphragm velocity assuming sinusoidal diaphragm displacement vs. time. Under these conditions the maximum diaphragm velocity is $\omega L_s$, where $\omega$ is the angular frequency equal to $2\pi$ time the frequency, and $L_s$ is the amplitude of speaker displacement (similar to $\delta$ used above in Section 2.1).

FIG. 7 shows the calculated tympanic membrane displacement vs. speaker displacement, for the sealed ear case, with trapped volume lengths of 1 cm and 0.5 cm. Note that there is no frequency dependence of the tympanic membrane displacement since the displacement depends on static pressure, which is related to speaker displacement, not to speaker velocity.

Speaker displacements in the micron range produce static-pressure-driven, tympanic membrane excursions that are also in the micron range, these are 100 to 1000 time the normal tympanic membrane excursion amplitudes, which are tens to hundreds of nanometers. The smaller the trapped volume, the greater the tympanic membrane excursion. This is because the same speaker displacement, relative to a smaller trapped volume, produces a greater pressure increase.

FIG. 8 shows the same tympanic membrane displacement vs. speaker displacement except that the tympanic membrane displacement is shown as a percentage relative to the driving speaker displacement.

At relatively small speaker displacements, the excursions of the tympanic membrane, as predicted by this simple model, are nearly the same as those of the speaker. In this case, the air in the trapped volume is behaving like a piston, which transfers motion from the speaker diaphragm to the tympanic membrane with negligible air compression. This occurs because at relatively small displacements, the tympanic membrane is extremely compliant, and thus it takes less energy to displace the tympanic membrane than to compress the air. However, as the speaker displacements become large, the percentage of this speaker displacement that is transferred to the tympanic membrane drops. This is because the tensile modulus of the tympanic membrane resists extremely large excursions of the tympanic membrane. At these higher speaker excursions the tympanic membrane can only do so much to absorb the compressive energy and some of this must be taken up by compression of the air in the trapped volume.

For comparison to the trapped volume situation, FIG. 9 shows the SPL values that the same speaker motions would produce in open air for three different frequencies (10, 100, and 1000 Hz). Clearly, the larger speaker displacements produce louder sound. The speaker motions in this study would give open air SPL values that span the range from normal conversation to a jet engine.

FIG. 10 shows the peak sound pressure (not rms average) for open air sound and the static pressure oscillation amplitude for the sealed ear canal, as a percentage of atmospheric pressure. For the open air case, even speaker displacements producing extremely high SPL, result in peak sound pressures which are a small fraction of atmospheric pressure. The pressure in the trapped ear canal volume at corresponding speaker displacements is higher at large speaker displacements. Note that the trapped volume pressures would be much higher still across the whole range of speaker displacements and would exceed the open air peak sound pressure even for small speaker displacements if it were not for the fact that the tympanic membrane displaces, nearly simultaneously with the speaker, to relieve the building static pressure.

FIG. 11 shows the same data as FIG. 10 in a different way. Here the ratio of the sealed volume static pressure to the corresponding open air peak sound pressure is plotted vs. speaker displacement. When this ratio exceeds 1.0, the sealed volume pressure in the ear is greater than the corresponding open air peak sound pressure. The pressures shown in FIG. 4 for a trapped volume with completely rigid walls provide a comparison to FIG. 11. The pressures in a completely rigid piston are seen to be considerably higher than the ear canal with its compliant tympanic membrane.

3.2 A More Realistic Model

Clearly the model of the previous section is an oversimplification. The ear canal is not a smooth, straight tube. The tympanic membrane is not flat, but rather an asymmetric, shallow, conical shape. The speaker diaphragm is usually not a flat surface, and the tympanic membrane has different modes of deformation beyond the biaxial stretching used in the simple model.

Wada, Kobayashi and co-workers have done extensive measurements and mechanical modeling of different components of the human middle ear. They show that excursions of the tympanic membrane involve deformation not just of the tympanic membrane itself, but also of the connection between the tympanic membrane and the ear canal, and of the ossicular chain, which connects the tympanic membrane to the cochlea. They have determined mechanical moduli associated with these other aspects of tympanic membrane deformation, which are included in the model described in this section.

Modeling of the static pressure effects with a speaker sealed in the ear depends only on the net change in trapped volume associated with the combined motions of the speaker diaphragm and the tympanic membrane. These changes depend on speaker and tympanic membrane geometry, but not on the ear canal geometry, since the morphology of the ear canal along the trapped volume remains the same as the volume changes. The other piece of information required to do the model calculation is the resistance to deformation of the tympanic membrane, including all the modes of deformation and the resistance to deformation of structures attached to the tympanic membrane that must move with it.

Wada and Kobayashi give an equivalent (spring-like) modulus for the attachment of the tympanic membrane ($k_w$=4000 N/m$^2$) and for the ossicular chain connection between the tympanic membrane and the cochlea ($k_s$=700 N/m$^2$). Once again the model is evaluated, for a given speaker displacement, by setting the pressure difference between the trapped volume in the ear canal and the pressure in the middle ear volume equal to the pressure across the deformed tympanic membrane (now including deformation of the attachment of the tympanic membrane and of the ossicular chain). The model is solved numerically, and in addition to the total displacement of the tympanic membrane, it yields an estimate of the amount of this displacement that occurs due to stretching of the tympanic membrane vs. due to motion at the attachment of the tympanic membrane to the ear canal.

FIG. 12, shows total tympanic membrane displacement vs. speaker displacement. This can be compared with FIG. 7 of the simpler model. The trend is the same, tympanic membrane displacement is in the multiple micron range and goes up with increasing speaker displacement. There is a slight decrease in the tympanic membrane displacement for the detailed model (FIG. 12) over the simple model (FIG. 7) because the detailed model includes additional resistance to deformation associated with the ossicular chain.

FIG. 13 shows the same tympanic membrane displacement vs. speaker displacement data as FIG. 12 except that the tympanic membrane displacement is shown as a percentage relative to the driving speaker displacement. This can be compared to FIG. 8 for the simple model.

The simple model (FIG. 8) indicated that at small speaker displacements that the tympanic membrane to speaker membrane was nearly one-to-one, and as the speaker displacement increased the percentage of that motion transferred to the tympanic membrane dropped off considerably. The detailed model (FIG. 13) amends that view and shows that the percentage of speaker displacement transferred to tympanic membrane displacement is less than 50% for small speaker motions and, while it drops with increasing speaker displacement, the drop is slight.

FIG. 14 shows the percentage of total tympanic membrane displacement which is due to stretching of the tympanic membrane, as opposed to motion at the connection of the tympanic membrane with the ear canal. Stretching of the tympanic membrane is clearly the dominant mode of deformation, although the displacement at its connection around its edges increases slightly as the speaker displacement gets large.

FIG. 15 shows the peak sound pressure (not rms average) for open air and the static pressure for the sealed ear canal volume as a percentage of atmospheric pressure. This can be compared to FIG. 10 for the simple model. For the open air case, even speaker displacements producing extremely high SPL, result in peak sound pressures which are a small fraction of atmospheric pressure. The pressure in the trapped volume at corresponding speaker displacements is higher at all speaker displacements than open air peak sound pressure level.

FIG. 16 shows the maximum static pressure that would be generated in the trapped volume of the ear canal, by the speaker motion, if the tympanic membrane were not allowed to move (similar to Beranek's completely rigid, sealed tube in Section 2.1, above). These pressures are about double the pressures in FIG. 15 for the more realistic situation in which the tympanic membrane can move. However the maximum pressures in FIG. 16 are important reference valves because they indicate the full magnitude of the static pressure driving force that is displacing the tympanic membrane. This pressure is not realized, however, because the tympanic membrane is already moving and relieving some of this static pressure before the speaker reaches its full displacement.

FIG. 17, shows the same data as FIGS. 15 and 16 in a different way. Here the ratio of the sealed ear canal static pressure to the corresponding open air peak sound pressure is plotted vs. speaker displacement. This can be compared to FIG. 11 for the simple model and to FIG. 4 for Beranek's sealed tube. The sealed volume pressure is higher than the open air peak sound pressure across the entire range of speaker displacements. The maximum pressures that would occur if the tympanic membrane could not move are seen to always be larger than the actual pressure. The maximum pressure values agree very well with those given by Beranek's acoustical analysis of a sealed tube.

All the modeling in this and the previous section was couched in terms of positive excursions of the speaker and tympanic membrane that raise pressure in the trapped volume. The converse analysis (in terms of negative excursions of the speaker and the tympanic membrane that lower the pressure in the trapped volume) yield similar results in terms of negative displacement of the tympanic membrane.

3.3 Detailed Model Including Dynamic (Frequency Dependent) Processes

The models above are based solely on static air pressure in the trapped volume. Even though this pressure is changing rapidly as the speaker diaphragm moves back and forth, it is indeed a static pressure at any given instant. If one could instantly freeze the position of the oscillating speaker diaphragm at any point in its displacement, the pressure in the trapped volume at that instant will remain constant, or static. This is not true of the same speaker in open air. If the speaker in open air is instantly frozen at some position, the sound pressure it is generating will dissipate very rapidly.

Even though the pressure in the ear canal resulting from a sealed speaker in the ear is static at any given instant, it is oscillating rapidly, and this has the potential to produce dynamic effects. In particular, the tympanic membrane and the structures attached to it have mass and inertia and therefore take a finite amount of time to respond to the pressure exerted on them, by the oscillating speaker diaphragm. This results in a phase lag between the driving speaker oscillation and the responding tympanic membrane oscillation. Additionally, the real structures of the tympanic membrane, the ossicular chain and the cochlea dissipate energy as they move (i.e. there is a small friction-like resistance to their motion). This damps the vibrational response of the tympanic membrane. The presence of these factors suggests that one should expect a frequency dependence to the oscillating static pressure in the trapped volume.

As discussed by Wada, Kobayashi and co-workers the displacement of the tympanic membrane can be modeled with the following equation of motion:

$$m(d^2\delta/dt^2)+\zeta(d\delta/dt)+k\delta=SP\sin\omega t \quad\text{(Eqn. 5)}$$

Here m is the mass of the tympanic membrane and other structures to which it is attached and which must move with it. The damping parameter $\zeta$ includes the damping influences of the tympanic membrane as well as the structures attached to it. The spring constant, k, includes the spring like resistance to displacement of the tympanic membrane and the structures attached to it. The displacement of the tympanic membrane at any given time, t, is given by the parameter $\delta$.

The first term on the left-hand-side of this equation represents Newton's law that force is equal to mass times acceleration. The second term adds the influence of damping or resistance, which is proportional to velocity. There is more resistance the faster one tries to move the tympanic membrane. The final term on the left-hand side gives the restoring, spring like, force associated with motion of the tympanic membrane.

This equation has the form of forced mechanical vibrations with damping. The forcing function is provided by the oscillation of the speaker diaphragm, as transmitted to the tympanic membrane through the air in the trapped volume. This driving function (right-hand-side of Equation 5) is represented by a sine wave with angular frequency ($2\pi$ time the sound frequency) $\omega$, and an amplitude given by the product of S, the area of the tympanic membrane, and P, the pressure which drives the motion. The driving pressure is the hypothetical maximum static pressure calculated in the previous section for various diaphragm displacements when the tympanic membrane is not allowed to move. This represents the total pressure driving force available to cause the motion of the tympanic membrane as governed by Equation 5.

Various literature references provide information on the masses, damping characteristics, and spring constants of the tympanic membrane and all the various structures to which it is connected. These values were the results of measurements on live subjects and on cadavers, as well as detailed finite element, computer modeling studies. Using these component parameters, values of m, ζ, and k that are representative of the overall characteristics of the moving structure were calculated. These values, when used in Equation 5, produced calculated tympanic membrane displacements for open air hearing of around 10 nm for, 80 dB SPL in the frequency range from 100 to 1000 Hz. This agrees with the results in FIG. 13 of Reference 28, thus confirming that this model produces realistic results for known conditions.

The solution to Equation 5 yields values for the amplitude of tympanic membrane displacement, δ, as well as the phase lag of tympanic membrane vibration relative to the oscillation of the driving (speaker) pressure.

FIG. 18 shows tympanic membrane displacements in microns vs. frequency for the range of speaker displacements ranging from 1 micron to 400 microns for a 1 cm long trapped volume.

The tympanic membrane displacements, which are on the order of microns to tens or hundreds of microns increase with speaker displacement, and are nearly constant for frequencies from 10 to 100 Hz. The values in this range are about the same as those obtained with the detailed static pressure model for the same speaker displacements (FIG. 12). The static pressure model does not contain a frequency dependence and is expected to be most similar to the dynamic model of this section at low frequencies.

FIG. 19 shows tympanic membrane displacements in microns vs. frequency for the range of speaker displacements ranging from 1 micron to 400 microns for a 0.5 cm long trapped volume.

The tympanic membrane displacements, which are on the order of microns to tens or hundreds of microns increase with speaker displacement, and are nearly constant for frequencies from 10 to 100 Hz. The values in this range are about the same as those obtained with the detailed static pressure model for the same speaker displacements (FIG. 12). The static pressure model does not contain a frequency dependence and is expected to be most similar to the dynamic model of this section at low frequencies.

FIGS. 18 and 19 show that at frequencies between 100 and 1000 Hz that the displacement starts to fall off with increasing frequency. This is due to the fact that at higher frequencies, inertial effects prevent the tympanic membrane and its associated structures from fully responding to the driving force before that force changes in magnitude and/or direction.

This lagging aspect of the physical dynamics is further illustrated by FIG. 20, which shows the phase lag as a function of frequency. The phase lag shown here is that between the tympanic membrane response and the driving motion of the speaker. This is not to be confused with the phase lag of the static pressure oscillations, which are also in phase with the speaker displacement and are 90 degrees out of phase with the velocity of the speaker and the resulting velocity of air molecules in the trapped volume.

The phase lag is the increment in the angular argument of the sine function by which the tympanic membrane response lags the speaker diaphragm driving function. This phase angle corresponds to an actual physical time lag (FIG. 21) of the response of the tympanic membrane vs. the driving oscillation of the diaphragm.

FIG. 22 shows the tympanic membrane displacement as a percentage of speaker displacement for a 1 cm long trapped volume and frequencies of 10, 100, and 1000 Hz. Compare this to FIG. 13 for the detailed static pressure model. The results in FIG. 22 for 100 Hz are close in valve to those of the static pressure model. The static pressure model indicates that this value is relatively constant to slightly decreasing with increasing speaker displacement. The dynamic model of FIG. 22 again indicates that the value is relatively constant with speaker displacement, but with a slight increase. The tympanic membrane displacement as a percentage of speaker displacement is seen to be highly dependent on frequency. Lower frequencies producing higher percentage displacements and higher frequencies producing lower percentage displacements.

FIG. 23 shows the tympanic membrane displacement as a percentage of speaker displacement for a 0.5 cm long trapped volume and frequencies of 10, 100, and 1000 Hz. Compared to FIG. 22, the smaller trapped volume produces larger percentage displacements of the tympanic membrane. Compared to FIG. 13, for the detailed static pressure model, the results in FIG. 23 for 10 to 100 Hz range are close in valve to those of the static pressure model. The static pressure model indicates that this value is relatively constant to slightly decreasing with increasing speaker displacement. The dynamic model of FIG. 23 again indicates that the value is relatively constant with speaker displacement, but with a slight increase. The tympanic membrane displacement as a percentage of speaker displacement is seen to be highly dependent on frequency. Lower frequencies producing higher percentage displacements and higher frequencies producing lower percentage displacements.

3.4 Summary, and Conclusions from Modeling 3.4.1 Limitations of Modeling

Theoretical modeling of the relatively simple type applied here can generally capture or predict the major trends in a physical system. The exact values calculated for various parameters, such as tympanic membrane displacement and pressure in the ear canal, are less important than the order of magnitude and overall trends of these parameters. This is the case for a number of reasons:

There is variability in the size and mechanical properties of the middle ear structures in the human population, and thus theoretically calculated values or experimental values obtained from individuals or averages of individuals, are not likely to match those found in any particular other individual. This also applies to the parameters m, ζ, and k used in the dynamic modeling calculations. The parameters used were based on measurements on groups of human subjects and on fitting of model calculations to data obtained from human subjects. These parameters do not necessarily apply perfectly to any given individual.

The models used are relatively simple and thus cannot take into account the full complexity of the natural systems that they are simulating. The hope is that the models capture enough of the essence of what makes the physical system work to provide some predictions of trends and the magnitude of responses. The most sophisticated modeling employed in this study is based on Equation 5. This equation assumes that all dissipative (damping) processes are linear in the velocity and that all elastic restoring forces are linear in displacement. There is no physical law that dictates this to be the case, although it is often a very good approximation. It is likely, however, especially at the very large deformations that occur with static pressures in trapped volumes in the ear, that some non-linear components of damping and elasticity are present. Such complexities would require a very involved and very detailed model, such as the finite element modeling of Wada and co-workers to capture.

3.4.2 What can be Concluded with Confidence from the Models

One reason for building up the modeling effort in a sequence, starting with a simple static model, followed by a detailed static model, followed by a fairly detailed dynamic model is to get an idea of the aspects of the system and the large overall trends that characterize its behavior. Aspects of the results that are consistent across the models from the simplest to the most complex are likely to be true features of the real physical system. Other aspects that change as the model details change, one must be less certain about.

FIG. 8 for the simple model, FIG. 13 for the detailed static model, and FIGS. 22 and 23 for the dynamic model all show the tympanic membrane displacement as a percentage of the speaker displacement. FIG. 8 shows a high value at low speaker displacements that drops off dramatically with increasing speaker displacement. FIG. 13 shows relatively constant percentage values with a slight down trend for increasing speaker displacement. FIGS. 22 and 23 show relatively constant percentage values with a slight uptrend for increasing speaker displacement. This is an example of a detail that the models do not all consistently predict, and thus it is difficult to draw firm conclusions. It is likely, based on the two more detailed models, FIG. 13 and FIGS. 22 and 23, that this percentage is relatively constant, and for low frequencies the detailed static model and the dynamic model agree quite well on the percentage range. However, one cannot make any conclusion about any up or down trend.

However, all three models agree on the main conclusions of the study. Sealing a speaker in the ear can produce dramatic over excursions of the tympanic membrane on the order of a micron up to tens or even hundreds of microns depending upon the speaker displacement. This is 100 to 1000 or more times the normal excursions of the tympanic membrane in open ear hearing. This occurs because the trapped volume of air in the ear canal acts as a pneumatic air piston with a rapidly oscillating static pressure.

The magnitude of the over excursions obtained from the detailed static model (FIG. 12) agree quite well in size to those found for the dynamic model in the low frequency range (10 to 100 Hz) in FIGS. 18 and 19. This reinforces the validity of both models and is expected since the assumptions of the static model are most applicable to the dynamic model at low frequencies (i.e. when it is most static). At higher frequencies the dynamic model (FIGS. 18 and 19) shows a drop off in tympanic membrane displacement.

The static pressure oscillations in the trapped volume of the ear canal can produce very high SPL especially at lower frequencies, and these static pressure oscillations are distinct from open air sound waves because their pressure oscillations are 90 degrees out of phase with velocity components. Normal, open air sound waves have their pressure oscillations in phase with their velocity components.

4. Impacts of Static Pressure Oscillations and Tympanic Membrane Over-Excursions on the Listening Experience As stated above, it seems likely that static pressure oscillations in the ear canal and the resultant over-excursions of the tympanic membrane trigger the stapedius reflex, contribute to listener fatigue, and may, through long term exposure, contribute to hearing damage.

4.1 Trapped Volume Insertion Gain

Audiologists refer to a phenomena known as insertion gain. This is an increase in the SPL of especially lower frequencies when a device, such as a hearing aid is sealed in the ear. Insertion gain is frequently measured by a probe microphone inserted into the sealed volume between the speaker and the tympanic membrane. An audiologist will typically reduce the bass output of a device, such as a hearing aid, in order to compensate for the insertion gain. Here we define a variant of this phenomena, which we call Trapped Volume Insertion Gain (TVIG), and show the TVIG to be largely, or perhaps exclusively, the result of the high amplitude static pressure oscillations in the trapped volume of the ear canal described above. The TVIG is the difference between the SPL in the sealed ear canal vs. the SPL when the speaker is held in approximately the same position but not sealed with an airtight seal. This is also approximately the same as the difference between the SPL in the sealed ear canal and the SPL that the sound wave would produce in open air.

4.1.1 Modeling of Trapped Volume Insertion Gain

FIG. 24 shows plots of total SPL in the sealed ear canal, including both acoustic waves and static pressure oscillations, vs. frequency. For comparison, open air SPL (not including any closed volume static pressure effects) is also plotted for the same frequencies and speaker displacements. These results for total SPL were calculated from the dynamic model of Section 3.3. The open air SPL values represent the acoustic sound waves that coexist in the ear canal with the static pressure waves. Below about 2000-3000 Hz, the oscillating static pressure boosts the overall SPL in the ear canal above the level associated with the acoustic waves. This static pressure boost decreases with increasing frequency. Although the static pressure gain, or TVIG, is frequency dependent it is a constant or approximately constant addition to open air SPL at a given frequency, regardless of how large or small this open air SPL is. This can be seen by comparing FIG. 24a, b, c, which span different SPL ranges for the same 10 to 1000 Hz frequency range. The functional form of the TVIG vs. frequency, as shown in FIG. 24 agrees, with what is found experimentally, as discussed below.

There may be a significant difference in TVIG as experienced by a listener and as measured by a probe microphone. The tympanic membrane moves in response to the full static air pressure compression resulting from the motion of the speaker diaphragm. These pressures are those shown in FIG. 16. These maximum static pressures are never realized in the ear canal because the tympanic membrane moves to relieve the pressure even as it is building in magnitude. However, the total motion of the tympanic membrane is the motion that would be driven by the maximum calculated pressure in FIG. 16. Thus the tympanic membrane, and the listener, experience a larger TVIG associated with the SPL equivalent of the maximum theoretical pressures generated by the speaker motion. These are the values reflected in FIG. 24, and these larger values are the ones that should be considered relative to the threshold for triggering the stapedius reflex.

A probe microphone in the ear canal, however, will measure a smaller TVIG because the motion of the tympanic membrane prevents the buildup of the peak SPL, due to static pressure oscillations, from being achieved in the ear canal. The tympanic membrane absorbs these higher pressure levels via its motion, and thus prevents the probe microphone from recording them. The distinction between TVIG as experienced by the tympanic membrane and TVIG as experienced by a probe microphone is important to understand when comparing to experimental data based on the readings of a probe microphone. FIG. 25 shows the same plots as in FIG. 24, except that that total SPL levels in the ear canal are those that would be recorded by a probe microphone. The TVIG that would be measured by the probe microphone is about 5 dB lower than the TVIG experienced by the tympanic membrane across the whole frequency range in which a TVIG is found.

At each frequency the TVIG is the difference between the total SPL in the sealed ear canal, including the effect of static pressure oscillations, minus the SPL due only to acoustical waves, which is the same as the open air SPL for which would result from the same speaker motion. The TVIG vs. frequency, as calculated from the model is shown in FIG. 26.

4.1.2 Experimental Measurements of a Speaker Sealed in the Ear, Including Trapped Volume Insertion Gain (TVIG)

The trends of displacement vs. frequency shown in FIGS. 18 and 19 for the dynamic model are born out experimentally by studies involving "Skullcandy™" ear buds sealed in a Zwislocki Coupler and also sealed in a human ear.

FIG. 27a shows the commercially available ear buds used in this study. FIG. 27b shows one of these ear buds sealed in a Zwislocki Coupler for testing. FIG. 27c shows one of these ear buds sealed in a human ear (Robert B. Schulein or RBS) for additional testing. In these tests, tones of various frequency as well as other audio clips were played by the iPhone® seen in FIG. 27b, through the ear buds. A small probe microphone (Knowles FG), shown in FIG. 28, is placed in the Zwislocki coupler or in the human subject's ear canal to recorded relative sound pressure level SPL as it exists in front of the ear drum. FIG. 29 shows the output from the probe microphone in the Zwislocki coupler and FIG. 30 shows the output from the probe microphone in the human ear canal during frequency sweeps.

In FIGS. 29 and 30, the frequency range to look at for comparison to the dynamical modeling of the ear bud sealed in the ear canal, is the range below 1000 Hz. Above this frequency range, the validity of the modeling is less sound because the length of the trapped volume is no longer a tiny fraction of the wavelength. Below 1000 Hz, the experimental data in FIGS. 29 and 30 shows the same trend as the modeling data in FIGS. 18 and 19.

The dynamic model in FIGS. 18 and 19 is showing tympanic membrane displacement in microns, while the experimental data in FIGS. 29 and 30 is plotting a measured quantity referred to as relative SPL. The relative SPL is not absolute SPL, but a log output to indicate changes or differences in sound pressure detected by the probe microphone, in the same units as SPL. Static pressure oscillations detected by this microphone, especially at low frequencies, will produce the same type of response from the microphone as any other sound waves, and thus contribute to relative SPL. This relative SPL is proportional in some way to the pressure driving force in the trapped volume, including both true acoustic sound pressure and oscillating static pressure, the combination of which is responsible for the motion of the tympanic membrane. Thus one would expect the relative SPL in FIGS. 29 and 30 to show the same general trend or general functional shape as the model tympanic membrane displacement in FIGS. 18 and 19. Note that both sets of graphs are plotted on log-log scales. In FIGS. 18 and 19 the tympanic membrane displacement is shown on a logarithmic scale, while in FIGS. 29 and 30 relative SPL is shown directly. However, SPL is itself a logarithmic scale and thus both sets of graphs show the data on the same type of axes.

Clearly both sets of graphs show a similar trend below 1000 Hz, a relatively constant value below 100 Hz and then a gradual drop off up to 1000 Hz. The more dramatic changes in the experimental data above 1000 Hz are likely due to the acoustic resonances and impedances of the ear canal and the ear buds themselves and not due to the trapped volume effect that are the subject of this application.

A test procedure to detect and quantify the degree to which an in-ear listening device produces an oscillating static pressure was devised. The oscillating static pressure can be quantified by observing the boost in SPL in the sealed vs. the non-sealed ear canal (or coupler standing in for the ear canal) and by measuring the phase shift of the sound in the sealed ear canal vs. the same device in the unsealed ear canal or test chamber. FIG. 31 illustrates an earbud (Skullcandy™ earbud shown) fitted into a Zwislocki coupler for testing. In FIG. 31a the earbud is inserted into the coupler but not sealed, while in FIG. 31b the earbud is in the same position, but is sealed by a rubber gasket.

FIG. 32a shows SPL measured as a function of frequency with a probe microphone inside the coupler of the test set-up of FIG. 31. The blue curve is the SPL measured when the earbud is not sealed in the coupler and the red curve is the SPL, with the same driving signals sent to the earbud, measured when the earbud is in the same position, but is sealed. The green curve is a zero noise calibration of the probe microphone. Subtraction of the blue curve from the red curve gives the boost in SPL in the ear canal (coupler) resulting from the sealing of the device in the ear canal, as shown in the graph of FIG. 32b. As previously described, this frequency dependent quantity is defined as the Trapped Volume Insertion Gain (TVIG). Clearly, there is a large boost in the low frequencies in the sealed over the unsealed case. The experimental data below about 2000 to 3000 Hz is remarkably similar to the modeling results in FIGS. 24 and 25. The calculations behind FIGS. 24 and 25 are based on the dominant influence of oscillating static pressure at low frequencies.

FIG. 32c shows the phase shift measured between the sound waves in the unsealed case (FIG. 31a) and in the sealed case (FIG. 31b).

FIG. 33 shows the experimentally determined TVIG plotted along with the theoretically calculated values (reproduction of FIG. 26). The agreement between the experimental data and the model, based on oscillating static pressure in a sealed ear canal, is quite good, especially considering that the ear canal dimensions and characteristics used in the modeling do not exactly match those of the Zwislocki coupler. This general agreement with experiment speaks to the validity of the underlying physical understanding on which the model is based.

For comparison to the experimental data in FIG. 32, FIG. 34 shows recently published data on a very similar experiment using insert headphones in a simulated ear canal. Free corresponds to the speaker inserted, but not sealed, in the ear canal. Long corresponds to a shallow sealed speaker insertion, yielding a longer, and therefore larger, trapped volume. Small corresponds to a deeper sealed speaker insertion, yielding a shorter, and therefore smaller, trapped volume. This third party experimental data shows similar magnitudes and trends to our experimental data and our modeling. Additionally, it shows that the influence of oscillating static pressure is more pronounced for smaller trapped volumes than for larger trapped volumes.

The influence of oscillating static pressure in the sealed ear canal is manifested by both the TVIG and by the phase shift. These effects are observed to become more pronounced as the frequency decreases, i.e. the TVIG increases with decreasing frequency and the phase shift increases with decreasing frequency, approaching it maximum value of 90 degrees. A 90 degree phase shift indicates a pure oscillating static pressure phenomena, condition approximated below about 30 Hz in the example study. Lower degrees of phase shift indicate the coexistence of oscillating static pressure and normal acoustic sound wave character. Asius Technologies, the assignee of the present technology, has developed the test procedure discussed here, as well as a method for analyzing the data that combines the influences of TVIG and phase shift into a parameter or family of parameters, which quantifies the oscillating static pressure characteristics of a given listening device.

Data is collected from the experiment of FIG. 32 as follows: Red curve is SPL vs. frequency for earbud sealed in coupler. Blue curve is SPL vs. frequency for earbud not sealed in coupler. Green curve is the noise floor.

Work is preferably conducted with sound pressures in Pa on a linear scale not the common log (dB) scale used for SPL. It is possible to work with rms pressures or peak pressures, as long as the units are consistent. The calculations for the sealed and open scenarios are given as:

$$p_s(\nu) = 10^{-6} 10^{(SPLred - SPLgreen)/20} Pa = \text{absolute sound pressure in sealed case}$$

$$p_0(\nu) = 10^{-6} 10^{(SPLblue - SPLgreen)/20} Pa = \text{absolute sound pressure in open case}$$

Phase difference, $\phi$, between the sealed and unsealed case (FIG. 32c) is also measured as a function of frequency and is expressed as a positive number in degrees (or rads for computation purposes). The phase difference should theoretically approach 90 degrees as frequency approaches 0.

To determine the characteristics of the SPL and phase data vs. frequency, the limits of integration will be from the lowest frequency measured, $\nu_o$ up to the place where the phase shift goes to zero $\nu_h$. The place the phase shift disappears (and hence the upper limit of integration) can be determined for each test or can be set at a fixed, standard value. Since the phase shift is zero above a certain frequency, the upper limit of integration can be a constant frequency that is high enough that the phase shift is never finite above it.

The values are cumulative sound intensities over a range of frequencies. These are directly proportional to the power generated over this range of frequencies, the proportionality constant being a characteristic area, which may be the ear canal cross section or the tympanic membrane area. This area, as well as the factor of one half times the reciprocal of the characteristic impedance ($\rho c$), need not actually be used in the calculations since it is only the ratios which are of interest and all the units divide out.

For 90 degree out of phase, oscillating static pressure (sp) the sound intensity is calculated as:

$$I_{sp} = \frac{1}{2\rho c} \int_{\nu_o}^{\nu_h} (p_s - p_o)^2 \sin\varphi \, d\nu$$

In phase, acoustic pressure (ap), sound intensity calculation is:

$$I_{ap} = \frac{1}{2\rho c} \int_{\nu_o}^{\nu_h} (p_s - p_o)^2 \cos\varphi \, d\nu$$

The calculation for total, unsealed sound intensity (all in phase) is:

$$I_o = \frac{1}{2\rho c} \int_{\nu_o}^{\nu_h} p_o^2 \, d\nu$$

The integrated sound intensity values calculated above will vary from set-up to set-up and from test to test. The following ratios, however, give fundamental properties of the particular coupling of a sound producing device and an ear that are independent of measurement system details, such as power supplied to the receiver, probe microphone characteristics, etc.

$$\Phi_{sp} = \frac{I_{sp}}{I_o}$$

$$\Phi_{ap} = \frac{I_{ap}}{I_o}$$

$$\Phi_{s/a} = \frac{I_{sp}}{I_{ap}} = \frac{\Phi_{sp}}{\Phi_{ap}}$$

Software has been written that works with a probe microphone to collect the data discussed above, plot graphs of SPL and phase shift or phase angle vs. frequency and do the calculations outlined above. The software quantifies the presence and extent of oscillating static pressure by a parameter, which is referred to herein as the "Ambrose number." This parameter is equal to or proportional to the formula $\Phi_{s/a}$ given above. Different formulations of the Ambrose number may also include scaling factors and separate contributions from $\Phi_{sp}$ and $\Phi_{ap}$. In addition to quantifying TVIG and Oscillating Static pressure, this same software, as part of an integrated package detects the triggering of the stapedius (acoustic) reflex when the listener is exposed to a real world sound stimulus such as a piece of popular music. This approach differs from what is done by audiologist with Tympanometry, because tympanometry uses pure test tones rather than real world stimuli.

The stapedius (acoustic) reflex test uses a piece of popular music or some other real world audio program material as the test stimulus. As in tympanometry, a probe tone is also used to detect the triggering of the stapedius reflex by the stimulus. The real world stimulus (piece of music) has a small band of frequencies (a notch) removed from its spectrum in the vicinity of the frequency of the probe tone. This is to prevent interference of the stimulus with the probe tone. The triggering of the stapedius reflex by the stimulus is detected by an increase in the volume of the probe tone detected by a probe microphone. As in tympanometry, this increase in the detected probe tone volume can be associated with a decrease in the effected trapped volume of the ear canal brought about by the stapedius (acoustic) reflex.

The software also performs a test for what is known as "Occlusion Effect." In this test a probe microphone is sealed in the ear canal and the sound pressure level (SPL) present due to natural body noises, pulse (blood flow) etc., is recorded as a function of frequency. This is compared to the SPL measured with the same probe microphone in the same position in the ear, but with the ear unsealed, i.e. open to outside air. The Difference between the SPL due to body noise for the sealed ear vs. the open ear quantifies the occlusion effect as a function of frequency. A single parameter, $I_{OE}$, is calculated to quantify the occlusion effect as the sound intensity (proportional to power) produced by occlusion over the entire frequency range tested from the low $\nu_o$, to the high $\nu_h$. This calculation is given below.

$$I_{OE} = \frac{1}{2\rho c} \int_{\nu_o}^{\nu_h} (p_s - p_o)^2 \, d\nu$$

Here $\nu$ is frequency, $p_s$ is the sound pressure in Pa due to body noises in the sealed ear, and $p_o$ is the sound pressure in Pa due to voice and natural body noises in the unsealed ear.

Note that sound pressures in this equation are expressed on the linear Pa (N/m²) scale rather than the logarithmic SPL (dB) scale. As above, ρc is the characteristic impedance.

The software package integrates the measurement of oscillating static pressure (Ambrose Number), Stapedius Reflex and Occlusion Effect into a single diagnostic tool for in ear listening devices such as a hearing aid, earbud, and headset. Since oscillating static pressure is a unique, fundamental discovery of the present inventors, the relationship of oscillating static pressure (Ambrose Number) to Stapedius Reflex and Occlusion Effect is a totally new feature of this approach and this software.

FIG. 51 shows a screen shot of the software package used to evaluate the oscillating static pressure for an earbud tip fitted with a covered vent to reduce the impact of oscillating static pressure. The upper graph shows SPL for the sealed and unsealed conditions, and the graph on the lower right shows the phase difference. The phase difference is about 45 degrees over a broad range indicating a reduction of osciallating static pressure, which would be maximized at a larger phase difference approaching 90 degrees. FIG. 52 shows the result of the Ambrose number calculation produced by this software.

The software described above can be used with a probe microphone to test the characteristics (oscillating static pressure, stapedius reflex, isolation and occlusion effect) of a particular ear sealing audio device (hearing aid, ear bud, head set) in a particular ear. The results depend upon both the anatomy of the ear and the structure of the device. This is useful, for instance, in fitting and adjusting a hearing aid.

It is also useful to have a standardized test probe that can be used to characterize the influence of ear anatomy on oscillating static pressure, stapedius reflex, isolation and occlusion effect. As shown in FIG. 53a,b the preferred probe includes the following components: (1) an ear seal to produce an acoustic seal in the ear canal, (2) a speaker or sound source which directs sound into the sealed space of the ear canal, (3) a probe microphone measuring sound pressure level (SPL) in the sealed space of the ear canal, and (4) a port between the trapped volume inside the ear canal and the outside air. A microphone external to the ear canal for comparison in isolation analysis may also be necessary for certain uses. The port may be opened, closed, or covered with a vent with a flexible membrane covering. Working with the software described above, this probe can be used to evaluate the acoustical characteristics (e.g., oscillating static pressure, stapedius reflex, isolation, occlusion effect) for a particular ear and it may be used to try out different covered vent options to see which is best for a patient's device (e.g., a hearing aid).

The probe of FIG. 53 was constructed by modifying an otoscope. The probe may also be a device with the components described above, but not built on an otosocope. The probe may also contain a port (not shown) connected to a micromanometer in order to measure pressure changes in the ear canal associated with mandibular (jaw) motion.

The described software also works to test devices such as earbuds or hearing aids with a standard coupler. FIG. 54 shows a coupler with an inserted earbud. This coupler includes a port which may be open, closed, or covered with various covered vents to perform the measurements necessary to evaluate a particular device for oscillating static pressure. The coupler has a probe microphone built into it, which provides data for analysis by the software.

In a practical demonstration of the described concept, a looping clip of a conga drum playing in the song "Hotel California" by The Eagles was used as the audio material for a test. FIG. 35 shows the relative SPL as measured by the probe microphone as a function for frequency, comparing the Skullcandy™ earphones sealed in a Zwislocki coupler to an open-air, desktop speaker. The Skullcandy™ output in the sealed volume of the coupler (red curve) is dramatically higher at low frequencies than the open air speaker (green curve). FIG. 36 shows the TVIG calculated by subtracting the Skullcandy™ output (red curve) from the open air speaker (green speaker), and FIG. 37 compares this experimentally measured TVIG to the model calculations based on oscillating static pressure. The curves in FIG. 35 and the resultant experimentally determined TVIG are gyrating wildly due to the complex frequency and volume content of the particular musical clip used in this study. However, it is clear that TVIG in the bass frequencies, when the Skullcandy™ earphones were sealed in the coupler, are consistent with the effect of large static pressure oscillations in the ear canal.

Using the same experimental setup as in FIG. 31 (i.e. identical ear tip insertion into a Zwislocki coupler, comparing sealed to unsealed conditions), the relative phase of the sound/pressure waves in the sealed volume was compared for sealed vs. unsealed conditions. The results are shown in FIG. 38. As expected the relative phase difference between the sealed and unsealed condition at the lowest frequencies is 90 degrees because the oscillating static pressure, in the sealed case, follows maximum speaker displacement, while in the unsealed case the acoustic wave maxima track the maximum speaker velocity, which occurs at zero speaker displacement.

4.2 The Stapedius Reflex

The dynamic range of the human cochlea is about 30% narrower than the range of sound pressure levels that can be heard. Louder sounds, above around 80 to 90 dB, are compressed to fit into the dynamic range of the cochlea by a response of the middle ear known as the Stapedius Reflex. In response to loud sounds, the stapedius muscle, which is connected to the stapes (stirrup) bone of the middle ear, contracts and thereby tightens the tympanic membrane. The contraction of the stapedius muscle also repositions the ossicles to pull the stirrup back, reducing the amplitude of motions transferred to the oval window of the inner ear. These mechanical adjustments to the middle ear, reduce its sensitivity and thus allow it to process louder sounds. This is a bit like switching from the "fine" to the "coarse" setting on a sensing device such as a voltmeter. The coarse setting allows much larger signals to be measured, but at the cost of reducing the sensitivity to small changes in the signal.

The fact that the stapedius reflex reduces our sensitivity to sounds at moderate sound pressure levels can be appreciated because of the vocalization-induced stapedius reflex. When a person speaks they automatically trigger a tensioning of the stapedius muscle which reduces the perceived amplitude of outside sound reaching the ear by about 20 dB, even if that sound is not loud enough to trigger the stapedius reflex itself. Most people will recognize this effect. Those who do not, can simply try taking and listening to an outside sound, of low to moderate volume, at the same time.

Numerous studies have been reported that measure the onset or threshold SPL above which the stapedius reflex occurs. This threshold, in humans, has been reported to be as low as 60 dB and as high as 90 dB. Above this threshold tightening of the stapedius muscle, compresses dynamic range. FIG. 39 shows that one study reported that the stapedius reflex threshold is relatively uniform across a broad range of frequencies and falls in the 70 to 90 dB range for people with normal hearing.

If anything, the stapedius threshold appears to be a little lower at lower frequencies than at higher frequencies, registering as about 75 dB in FIG. 39 at 125 Hz.

It is proposed herein, to Applicants' knowledge for the first time, that the stapedius reflex, triggered by the high, oscillating static pressures and the corresponding high TVIG induced SPL in the sealed ear canal at low frequencies, is a major contributor to audio (listener) fatigue, and produces a diminishment of the quality of the listening experience. As shown above, through modeling and through experiments, sealing a speaker in the ear, as is done with insert headphones, results in oscillating static pressures in the ear canal, which can also be interpreted as equivalent SPL, and which produce abnormally large excursions of the tympanic membrane. At even moderate listening volumes, the TVIG at lower frequencies can easily push the SPL in the ear canal above the stapedius reflex threshold, which FIG. 39 indicates is about 75 dB at 100 Hz. Other studies report this threshold to be as low as 60 dB, and of course there is variation from individual to individual.

FIGS. 24 and 25 show modeling results indicating that playing audio, which would yield an SPL of 60 dB in open air, yields an SPL of over 100 dB in a sealed ear canal. This boosted SPL in the trapped volume would certainly trigger the stapedius reflex in an individual with normal hearing. FIG. 32a shows experimental data in which the SPL produced by a Skullcandy™ insert headphone sealed in the ear (red curve) is as high as 75 dB at 100 Hz and below. Absolute SPL values are obtained by subtracting the green background (taken as zero dB) from the graph of interest. Note that this experiment was actually performed at very low sound levels as indicated by the unsealed earbud data (blue curve), which is at only about 20 to 25 dB at 100 Hz and below. These low open air sound levels were used in the experiment of FIG. 32a so that the large TVIG upon sealing the speaker in the coupler did not produce red curve SPLs that exceed the linear response range of the insert microphone. Never-the-less, the data in FIG. 32a shows sealing in the ear can boost a whisper-quiet speaker output to a level where it can trigger the stapedius reflex.

If a person is listening to insert headphones at what would be considered a normal level, it is very likely that the low frequency content of the audio will produce oscillating, high amplitude pressures in the ear canal, which will trigger the stapedius reflex. It is likely that many or even most people who listen to insert earphones are doing so with their stapedius reflex constantly triggered. This can have a number of deleterious effects: The stiffening of the oscular chain and the tympanic membrane brought about by the stapedius reflex reduce the sensitivity of the hearing system to other frequencies (especially in the midrange), which may not be boosted above the stapedius reflex threshold. To use the voltmeter analogy, the booming, trapped volume, bass turns the meter on "coarse," which then means that it does a poorer job registering the smaller nuances and variations of the signal at other frequencies.

Also, the stapedius muscle is like any other muscle in the body in that it will fatigue from overuse. We believe that is a major cause of the listener fatigue reported by some users for insert headphones. In the natural conditions under which humans evolved, the stapedius reflex would likely be triggered somewhat rarely and not for extended periods of time. A person listening to insert headphones, however, may be placing their stapedius muscle in an unnatural state of permanent or near-permanent contraction. This will fatigue the muscle and perhaps other tissues in the ear to which it is connected.

4.3 Air Spring Resistance to Tympanic Membrane and Speaker Motion

FIG. 6 provides a schematic illustration of the fact that a sealed speaker in the ear interacts with the tympanic membrane through two different spring-like volumes of confined air: the trapped volume in the ear canal and the volume of the middle ear. In normal, open ear, hearing, the tympanic membrane rests on a single air spring, the air filled volume of the middle ear. This air spring influences the open ear response of the tympanic membrane and provides a component of the restoring force, which resists its normal displacement.

When the ear canal is sealed, a second air spring is created from the closed volume in the ear canal. Depending on how deep the seal is inserted, the trapped volume in the ear canal may be smaller than the middle ear volume. The stiffness of an air spring is inversely proportional to its volume, and thus the smaller trapped volume in the ear canal can be a stiffer resistance to tympanic membrane motion. With a sealed ear canal, the tympanic membrane is held on both sides by air springs that resist its motion.

This air spring effect contributes to the effectiveness of silicone ear plugs at reducing the perception of noise. The ear plug seals the ear canal creating a trapped volume, air spring, which resists motions of the tympanic membrane. The ear plug reduces what a person hears not only because it blocks sound from entering the ear canal, but also because it creates a trapped volume in the ear canal that helps hold the tympanic membrane still.

The large amplitude static pressure oscillations resulting from the motion of the speaker interacting with this trapped volume are an example of the air spring in the ear canal being used to drive motions of the tympanic membrane. However, other smaller amplitude acoustical waves that may co-exist with these static pressure oscillations may be fighting the trapped volume air spring as they attempt to move the tympanic membrane. This will lead to a damping of the acoustical waves (mainly higher frequencies) in the ear canal in favor of the static pressure oscillation waves (mainly lower frequencies).

As shown in FIGS. 24 and 25, the oscillating static pressure makes up a large portion of the audio signal at lower frequencies but at higher frequencies, the signal is predominantly acoustical waves. To the extent that the air spring resistance discussed above, damps out acoustical waves, this will disproportionately reduce and distort the high frequency content of audio.

Also, the air spring effect of the trapped air in the ear canal, will create a back pressure or load on the speaker diaphragm itself. This will require more power to drive the speaker at a given sound output and displacement than in open air. Additionally, this loading may distort the speaker's frequency response and dynamic range. The louder the sound produced by the speaker in a sealed ear condition, the larger the speaker displacement required. This in turn will cause an increasing air-spring resistance to the speaker motion. This will have the effect of resisting higher volume sound production. This effect can be understood quantitatively in terms of the mechanical impedance to sound radiating motion of the speaker as modeled in Beranek. The mechanical impedance of an oscillating surface, radiating sound, including a planar surface sealing off one end of a tube, is proportional to the density of the air in front of the surface. The mechanical impedance as discussed in Beranek refers to the impedance of the motion of the speaker associated with the production of acoustical sound waves. This model does not include any physics to take into account static pressure oscillations. However, it is clear that the static pressure oscillations result in corresponding oscillations in the density of the air in the trapped volume. This leads to oscillations in the mechanical impedance of the speaker, which impact the speaker's coincident production of sound waves. This oscillating impedance of the speaker, associated with lower frequency static pressure oscillations, may have an effect similar to that illustrated in FIG. 40, on the speaker's output of higher frequencies, i.e. a pulsing of the higher frequency wave associated with lower frequency oscillations in speaker impedance.

4.3 Large Excursions Stiffen the Tympanic Membrane

FIG. 40 illustrates a potential distortion that could result from large over-excursions of the tympanic membrane.

As indicated by the third term on the right-hand side of Equation 5, the spring-like resistance of the tympanic membrane to displacement increases with increasing displacement from its resting position (i.e. the zero displacement position of its motion). The lower curve in FIG. 40 shows the tympanic membrane's vibrational response when a high frequency tone is present along with a lower frequency tone, which is producing large over excursions of the tympanic membrane through trapped volume static pressure oscillations. The high frequency waves that occur when the tympanic membrane is near the extremes of its over-excursions produce less of a response (less motion) of the tympanic membrane because the tympanic membrane is stiffened at the extremes of the over excursions. Conversely, the high frequency waves that occur near the mid-point of the over-excursions produce a larger response from the tympanic membrane because the tympanic membrane is less stiff when it is near is zero of displacement. Note that in normal, open ear sound, all tympanic membrane displacements are small and thus this distortion is not present. The upper curve in FIG. 40 shows the resultant displacement of the tympanic membrane due to the higher frequency sound (amplitude expanded relative to the lower curve for clarity). The amplitude of this higher frequency sound beats at a frequency equal to double the frequency of the lower frequency tympanic membrane over-excursions. Beating of the amplitude of higher frequencies synchronously with lower frequency over-excursions may contribute to the audio fatigue and the percussive effect on the eardrum reported by some listeners. Even if the over-excursions of the tympanic membrane do not produce audible sound (because they are of very low frequency), the resultant beating of the volume of other frequencies in the audio material may produce these undesirable effects.

4.4 Infrasound

Sound at frequencies lower than 20 Hz is known as infrasound. Most people cannot hear these very low frequencies, but may feel them as vibrations. Although the experimental results presented above were only measured down to 20 Hz, the top end of this range, it is clear that insert headphones of the type tested will be able to produce frequencies in the infrasound range. Additionally, the trapped volume effect of the ear canal will boost these infrasound frequencies via oscillating static pressure effects.

The infrasound content of recorded music and other audio material is not well understood. Normal, open air sound equipment like home and car stereo systems cannot produce much output volume below about 50 Hz, and thus the low frequency content of recordings has not been considered important. However, insert headphone, like the Skullcandy™ tested in this study, can produce these low frequencies, and these frequencies are dramatically boosted by static pressure oscillations in closed volumes, such as the ear canal.

Exposure to infrasound has been linked to illness and health problems, and is even the basis for some sonic weapons. The use of headphones sealed in the ear may be exposing people to infrasound. Among other benefits, the inventive device described below, may lessen infrasound exposure.

SUMMARY OF THE INVENTIONS

There is disclosed herein an improved device for in-ear or over ear placement by a user which avoids the disadvantages of prior devices while affording additional structural and operating advantages.

Generally speaking, the invention of the present application, numerously embodied in countless combinations of components, is comprised of an in ear or over ear sound device which seals either within the ear canal of the user or over the outer ear of the user. A covered vent is provided in a sidewall portion of the sound device to reduce the trapped volume insertion gain as a result.

In embodiments of the invention, the vent is provided on an earbud portion of headphones. The vent is in communication with the sound tube of the device. The vent may be adjustable to change the opening of the vent. A plurality of adjustable vents may also be provided in specific embodiments.

In embodiments of the invention, the vent is provided on a housing of in-ear headphones. The vent is in communication with the sound tube of the device. The vent may be adjustable to change the opening of the vent. A plurality of adjustable vents may also be provided in specific embodiments.

In other embodiments of the invention, the vent is provided on an ear enclosure portion of over ear headphones. The vent is in communication with an interior volume of the ear enclosure of the device. The vent may be adjustable to change the opening of the vent. A plurality of adjustable vents may also be provided in specific embodiments.

Methods for manufacturing and retrofitting in-ear and over ear devices are also claimed.

BRIEF DESCRIPTION OF THE DRAWINGS

For the purpose of facilitating an understanding of the subject matter sought to be protected, there are illustrated in the accompanying drawings embodiments thereof, from an inspection of which, when considered in connection with the following description, the subject matter sought to be protected, its construction and operation, and many of its advantages should be readily understood and appreciated. The components in the drawings are not necessarily to scale, emphasis instead being placed upon illustrating the principles of the invention. In the following description and throughout the numerous drawings, like reference numbers are used to designate corresponding parts.

FIG. 26 is graphs showing TVIG vs. frequency;

FIGS. 27(*a-c*) are a series of images of a commercial brand earbud sold under the tradename Skullcandy™ used is a test apparatus and positioned in a user's ear;

FIG. 45(*a,b*) are images of embodiments of over-ear headphones made in accordance with the invention of the present application;

FIG. 57(*a,b*) are images illustrating the modification of a headphone tip in accordance with an embodiment of the present invention.

DETAILED DESCRIPTION OF EMBODIMENTS OF THE INVENTION

Figure 1:
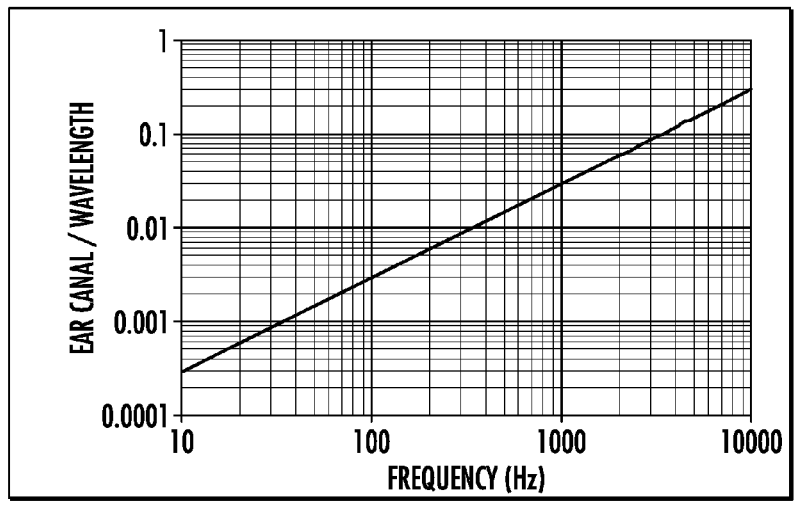
FIG. 1 is a graph showing the length of a trapped volume as a fraction of a wavelength of sound across a frequency range.
Figure 2:
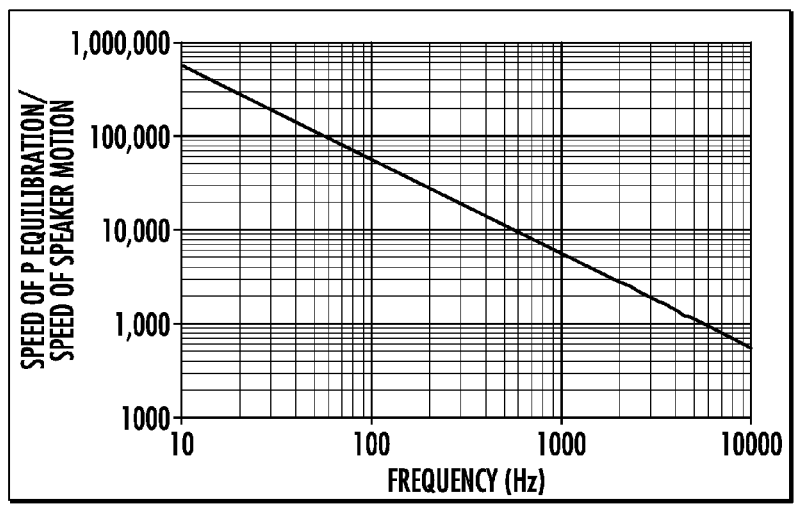
FIG. 2 is a graph plotting the ratio of the speed of pressure equilibration vs. peak speed of speaker motion across a frequency range.
Figure 3:
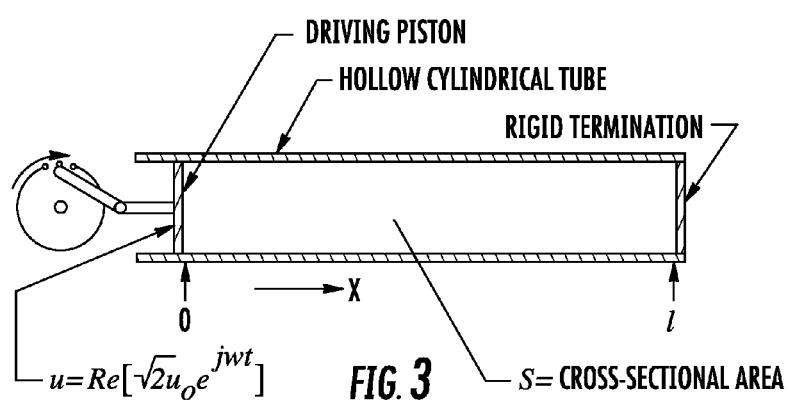
FIG. 3 is a reproduction of a prior art test apparatus having a rigid piston oscillating in one end of a rigid tube.
Figure 4:
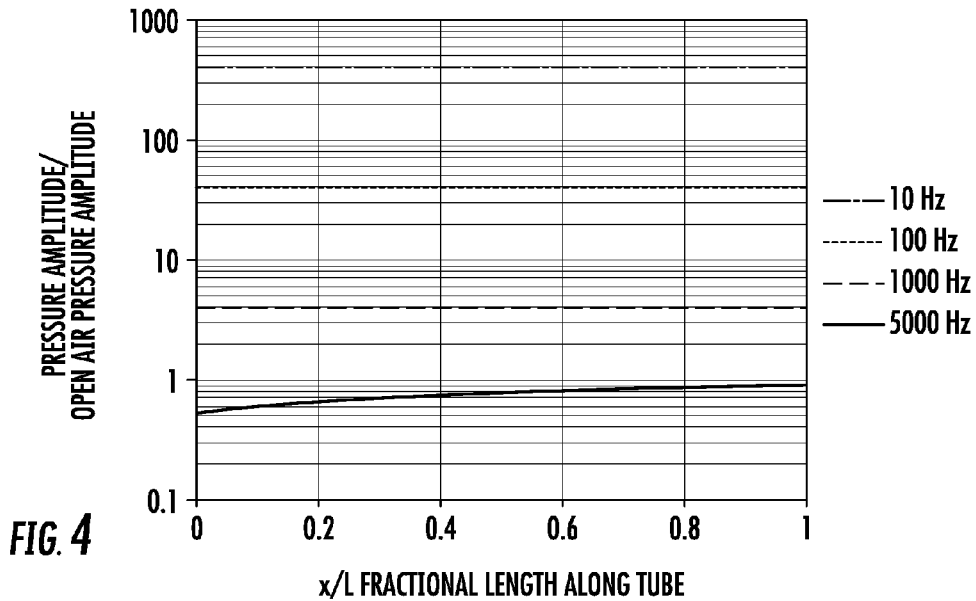
FIG. 4 is a graph showing pressure profiles along a one cm tube.
Figure 53A:
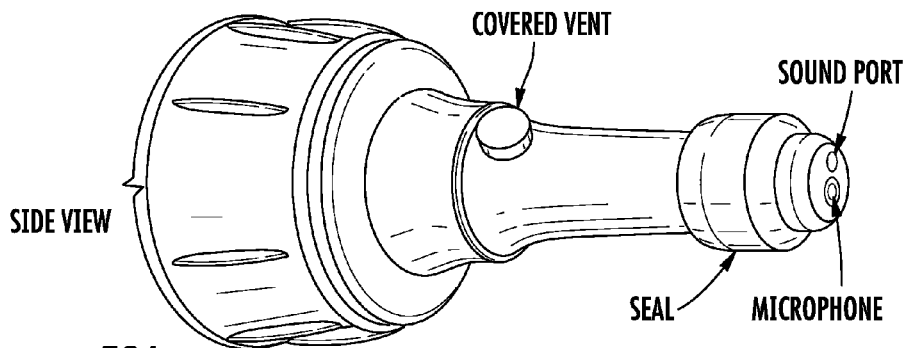
FIG. 53(*a,b*) are images illustrating an embodiment of an in ear probe design.
Figure 53B:
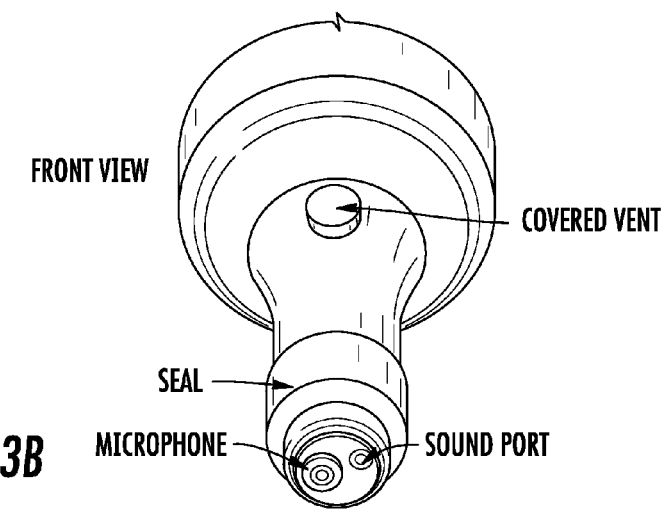
Figures 5A, 5B:
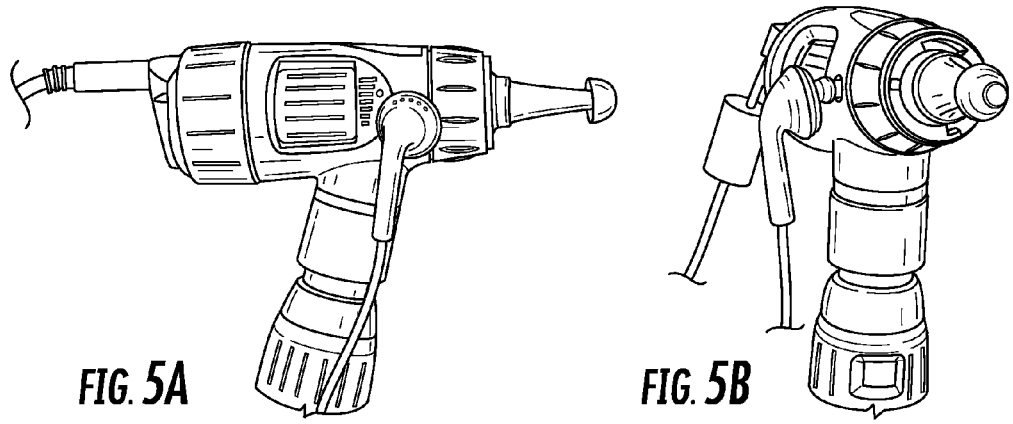
FIGS. 5(*a-c*) are photographs of an Otoscope having an attached earbud.
Figure 5C:
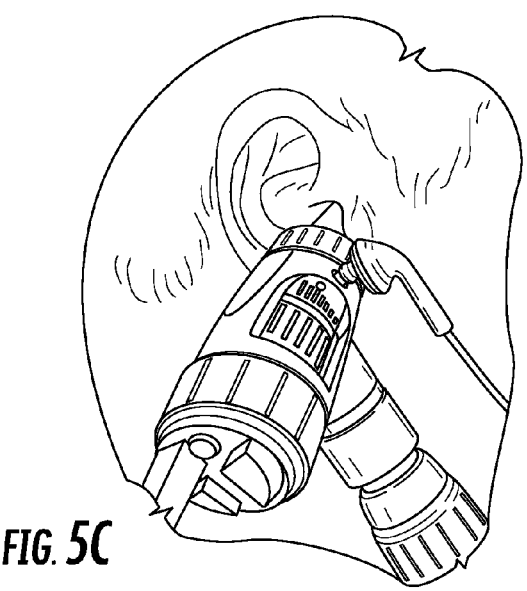
Figure 6:
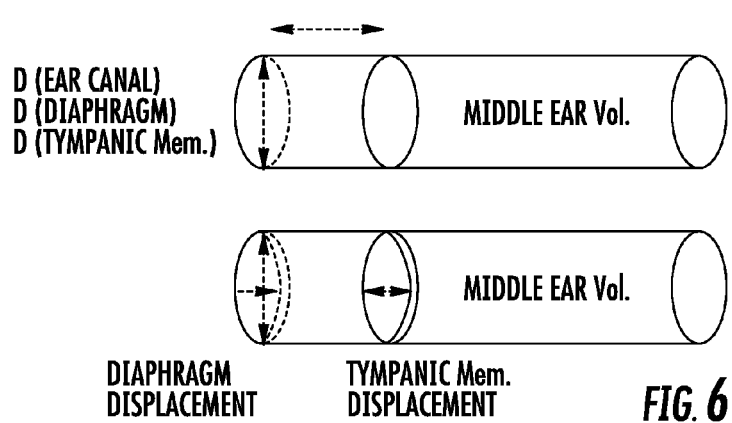
FIG. 6 is a schematic of a simplified model for trapped volume in an ear canal.
Figure 7:
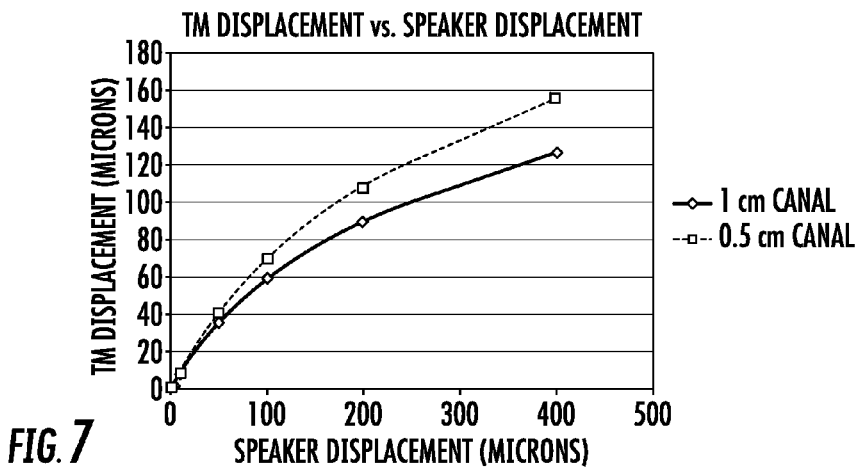
FIG. 7 is a graph showing a calculated tympanic membrane displacement vs. speaker displacement.
Figure 8:
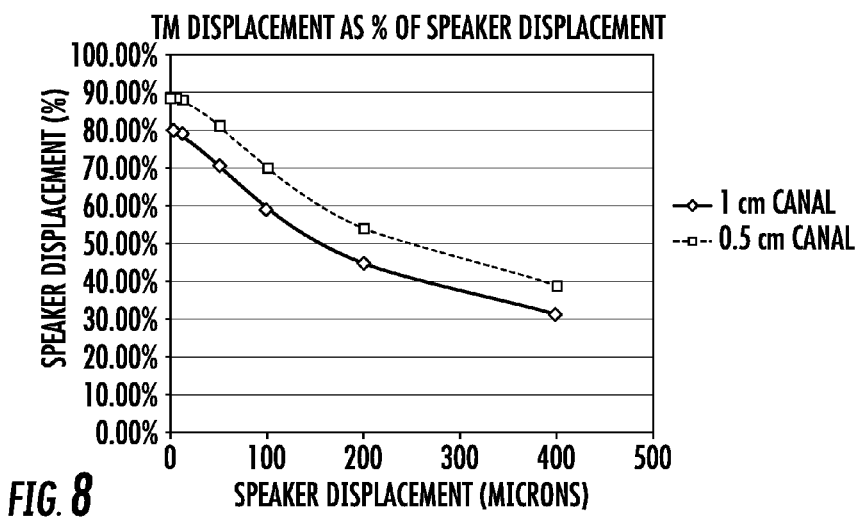
FIG. 8 is a graph similar to FIG. 7 except the tympanic membrane displacement is shown as a percentage relative to the speaker displacement.
Figure 9:
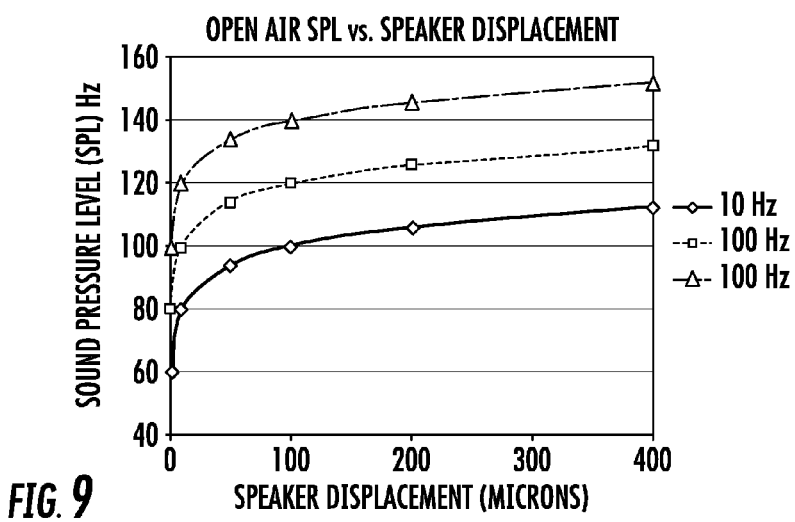
FIG. 9 is a graph showing SPL values for speaker motions in open air.
Figure 10:
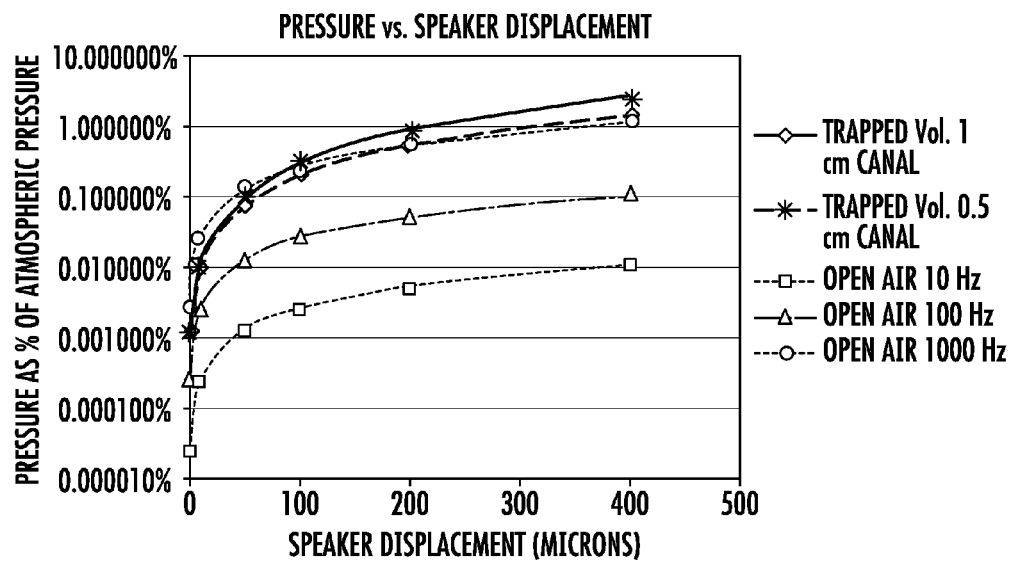
FIG. 10 is a graph showing peak sound pressures for open air sound and static pressure oscillation amplitude for a sealed ear canal.
Figure 11:
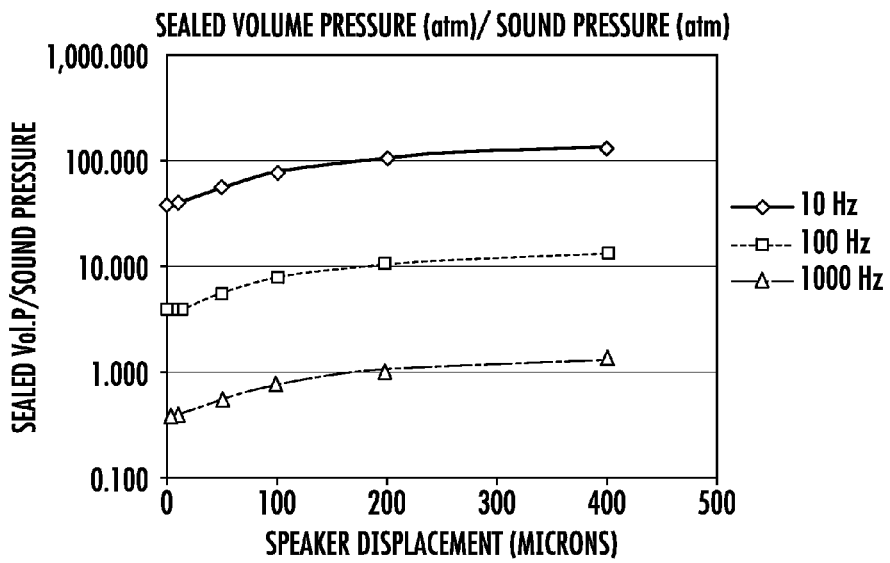
FIG. 11 is a graph similar to FIG. 10 showing a ratio of a sealed volume static pressure to the corresponding open air pressure.
Figure 12:
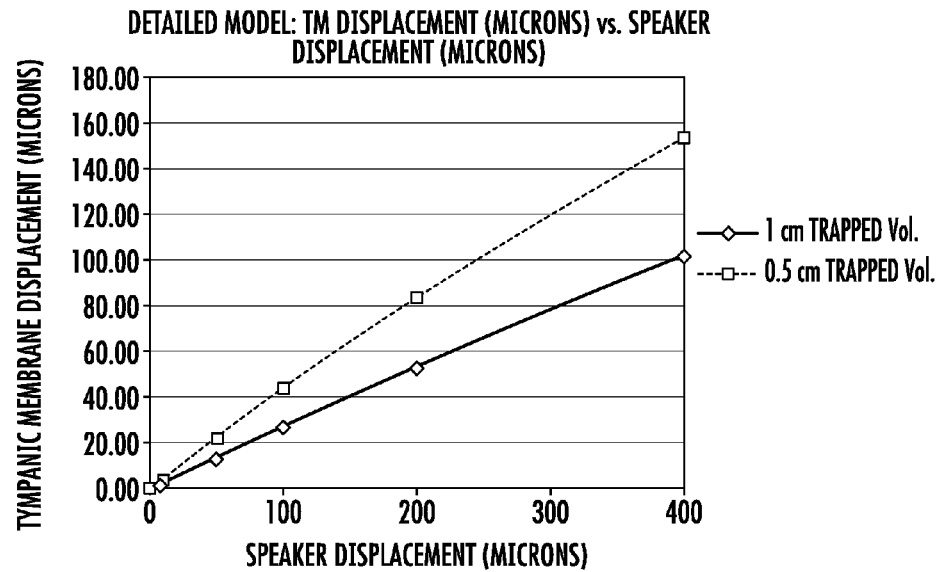
FIG. 12 is a graph showing tympanic membrane displacement vs. speaker displacement.
Figure 13:
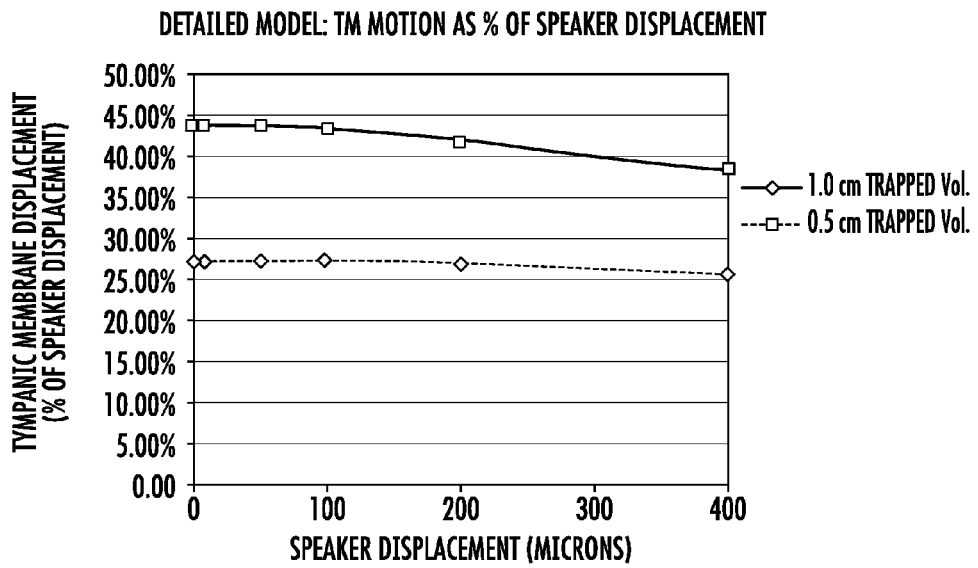
FIG. 13 is a graph similar to FIG. 12 showing tympanic membrane displacement as a percentage of speaker displacement.
Figure 14:
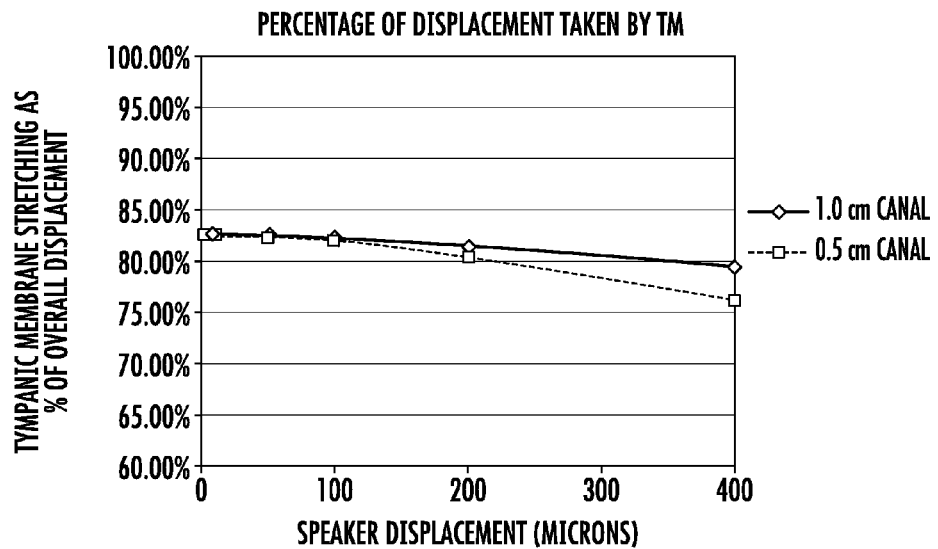
FIG. 14 is a graph similar to FIG. 12 showing tympanic membrane displacement as a percentage of overall displacement.
Figure 15:
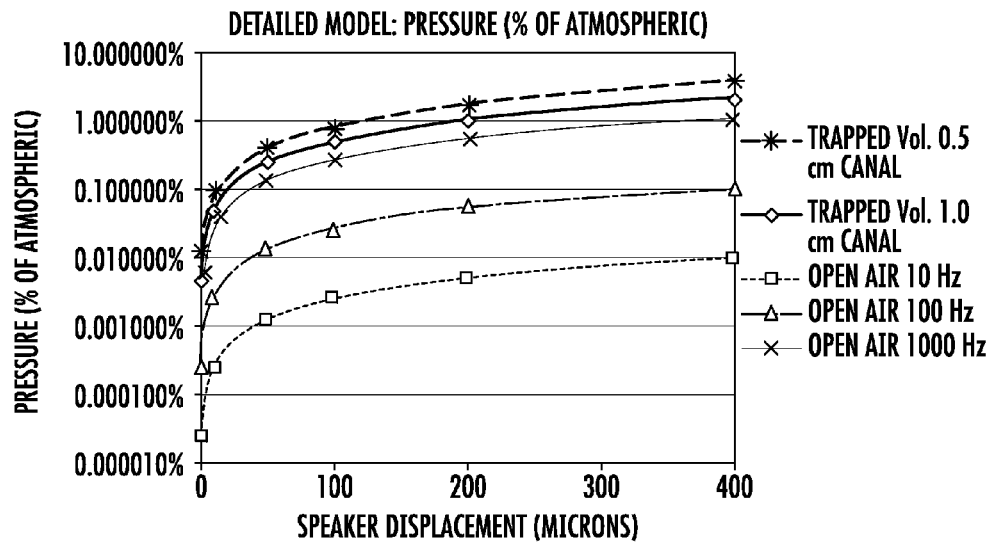
FIG. 15 is a graph showing peak sound pressure or open air and static pressure for the sealed ear canal volume as a percentage of atmospheric pressure.
Figure 16:
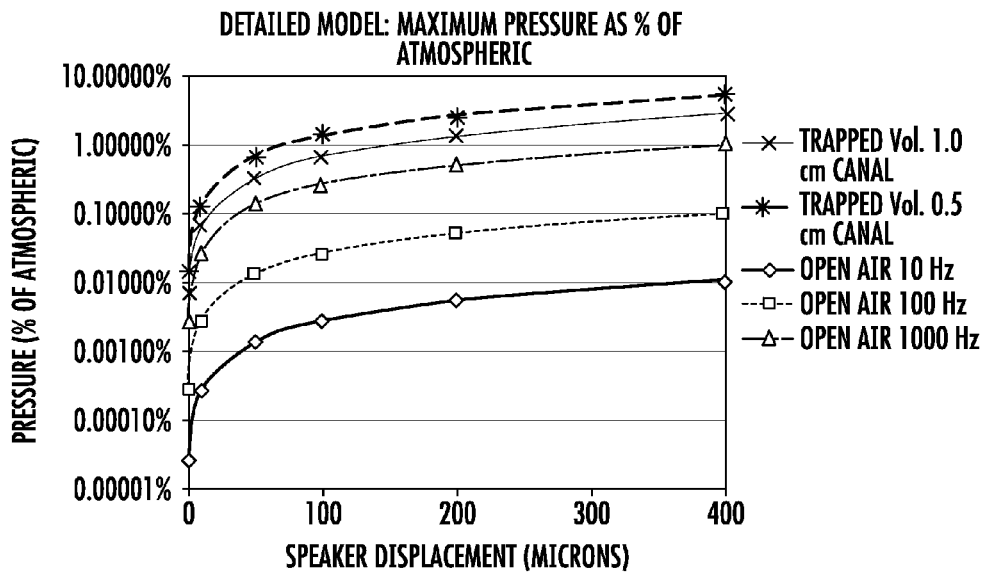
FIG. 16 is a graph showing maximum static pressure generated in a trapped volume of an ear canal.
Figure 17:
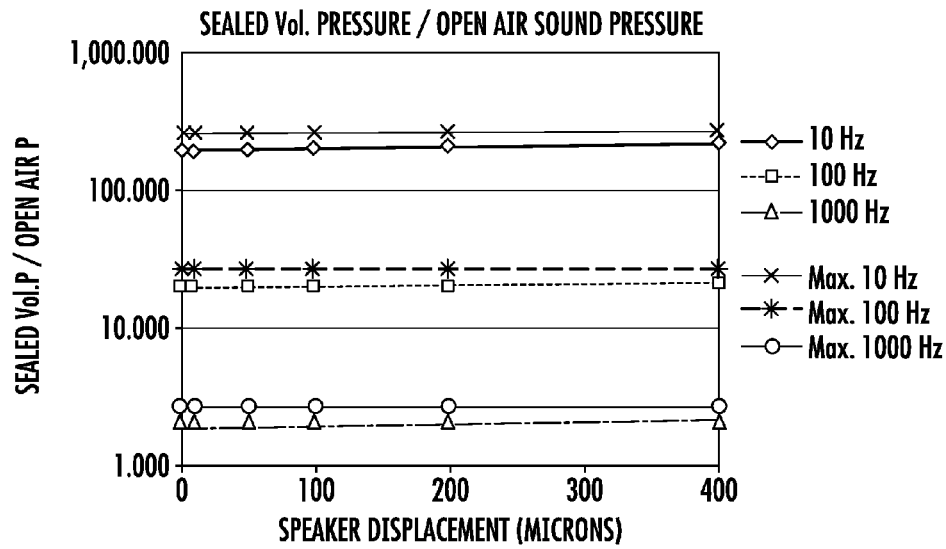
FIG. 17 is a graph showing data similar to that of FIGS. 15 and 16.
Figure 18:
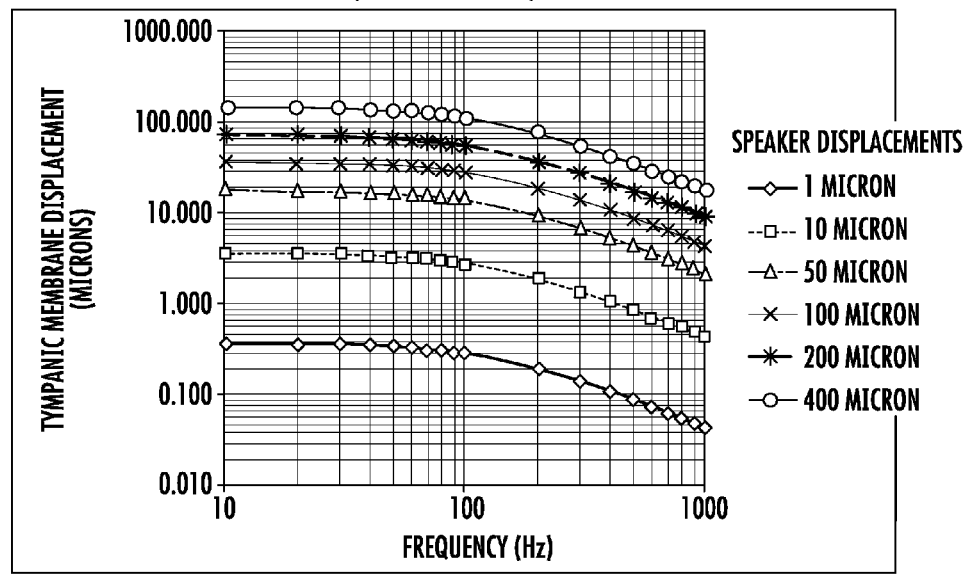
FIG. 18 is a graph showing tympanic membrane displacement vs. frequency for a range of speaker displacements for a one cm trapped volume.
Figure 19:
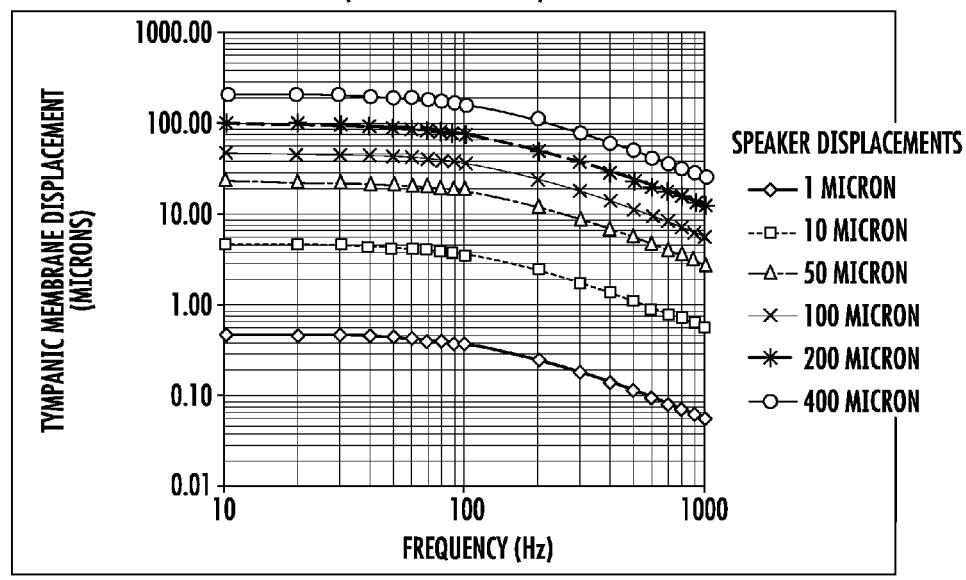
FIG. 19 is a graph showing tympanic membrane displacement vs. frequency for a range of speaker displacements for a 0.5 cm trapped volume.
Figure 20:
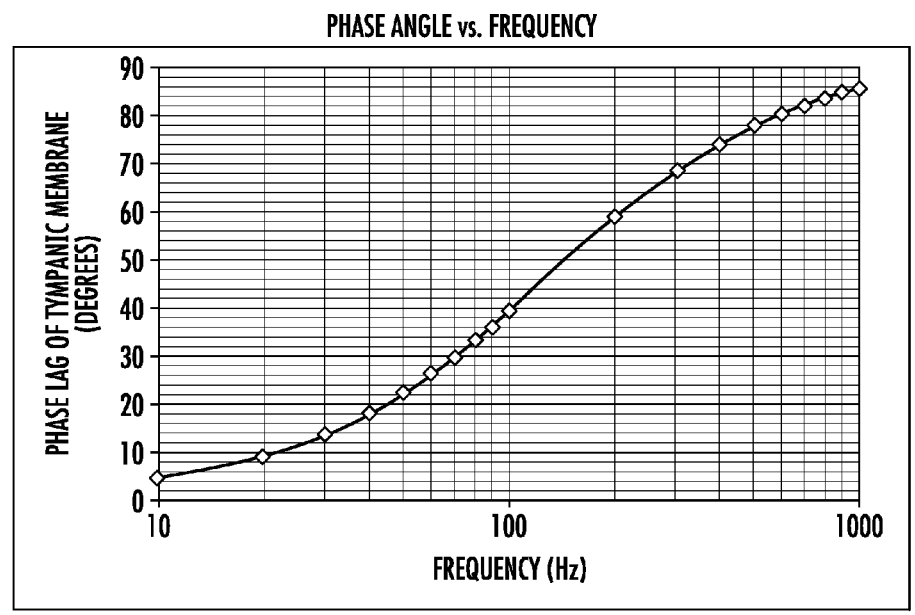
FIG. 20 is a graph showing a phase lag of the tympanic membrane response to a speaker motion.
Figure 21:
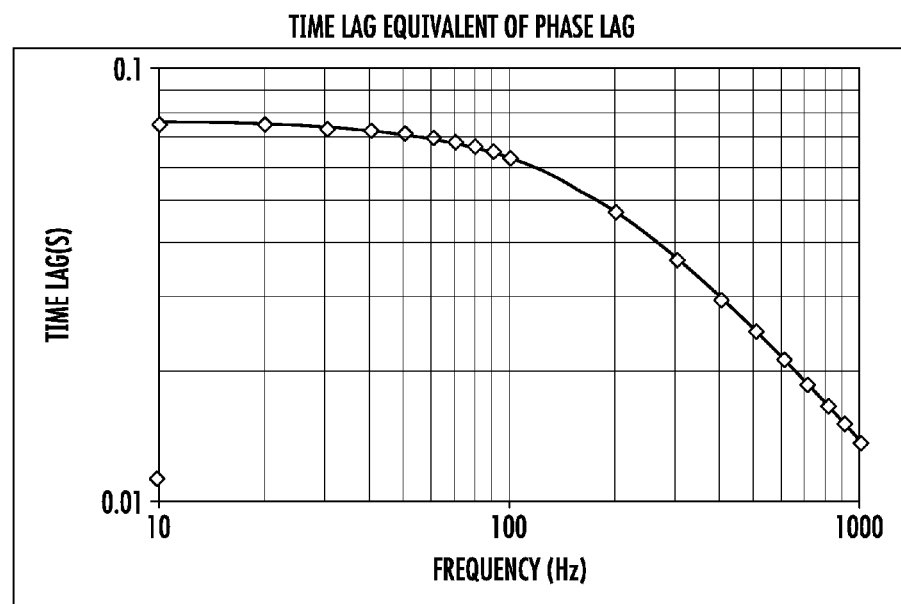
FIG. 21 is graph showing a time lag equivalent of the data of FIG. 20.
Figure 22:
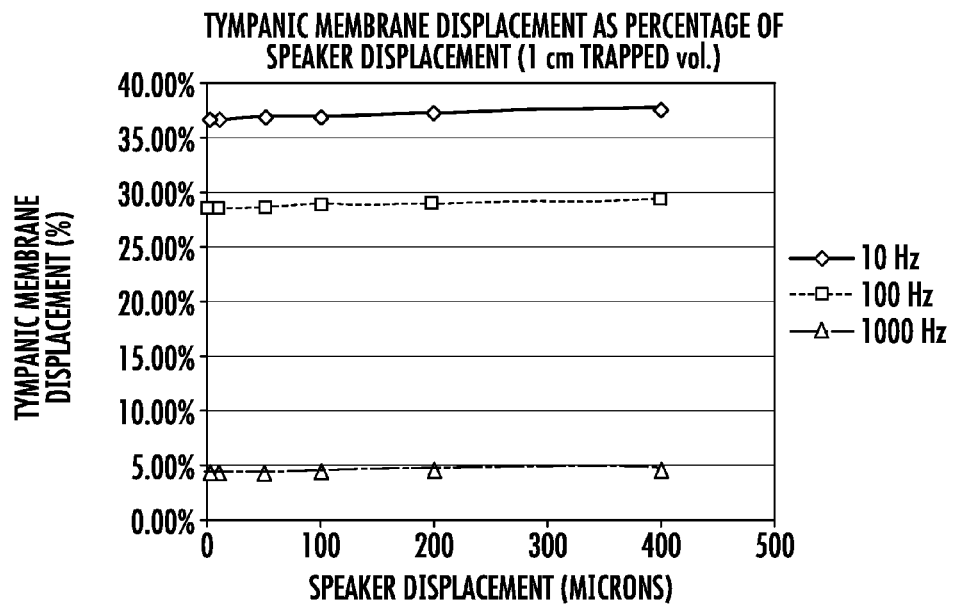
FIG. 22 is a graph showing tympanic membrane displacement as a percentage of speaker displacement for a one cm trapped volume.
Figure 23:
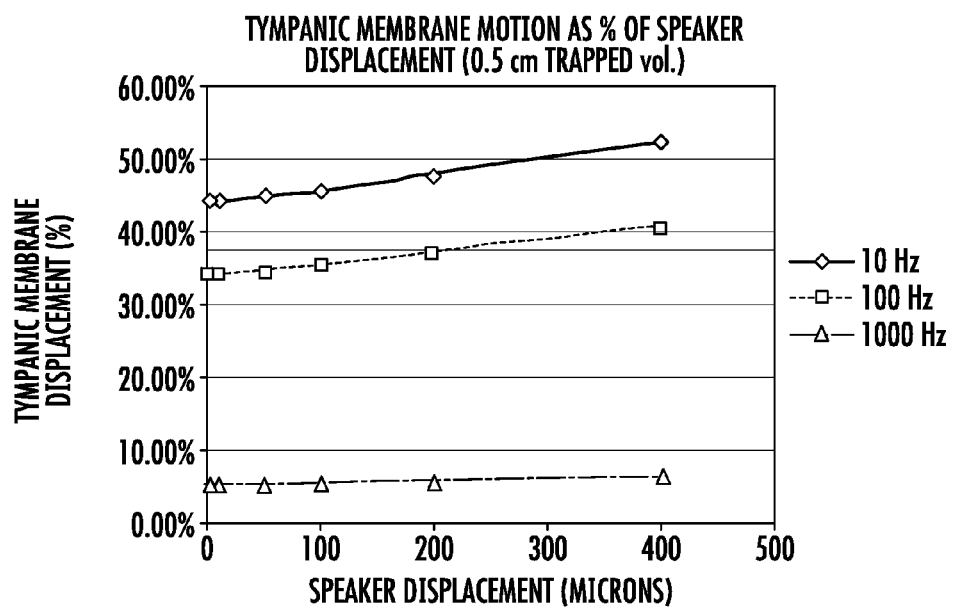
FIG. 23 is a graph showing tympanic membrane displacement as a percentage of speaker displacement for a 0.5 cm trapped volume.
Figure 24A:
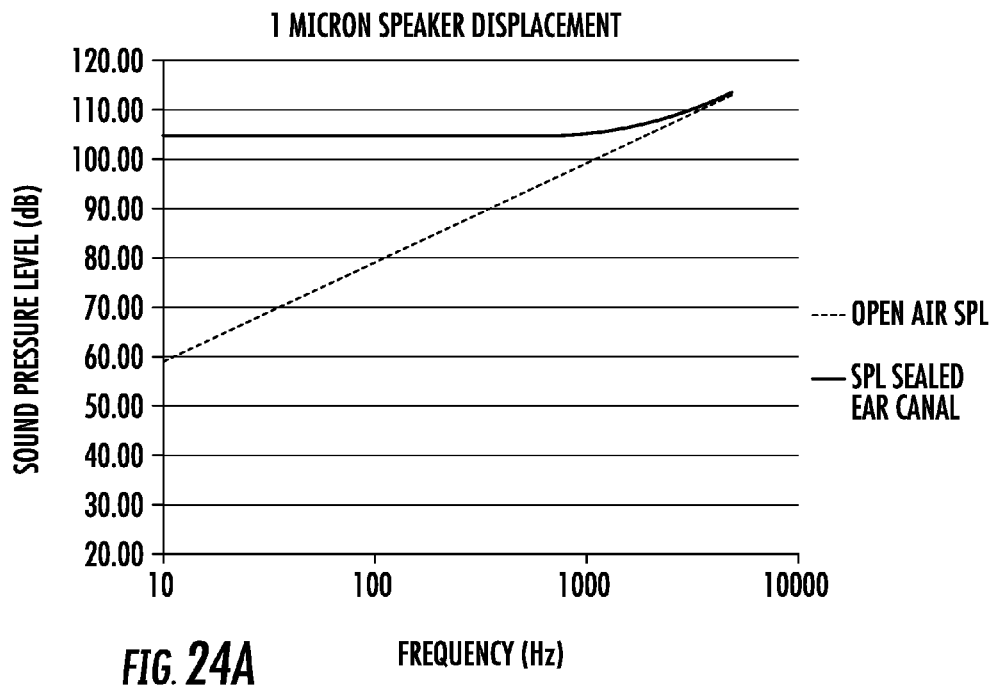
FIGS. 24(*a-c*) are graphs showing open air and sealed ear SPL data along a range of frequencies for 1, 10 and 100 micron speaker displacements.
Figure 24B:
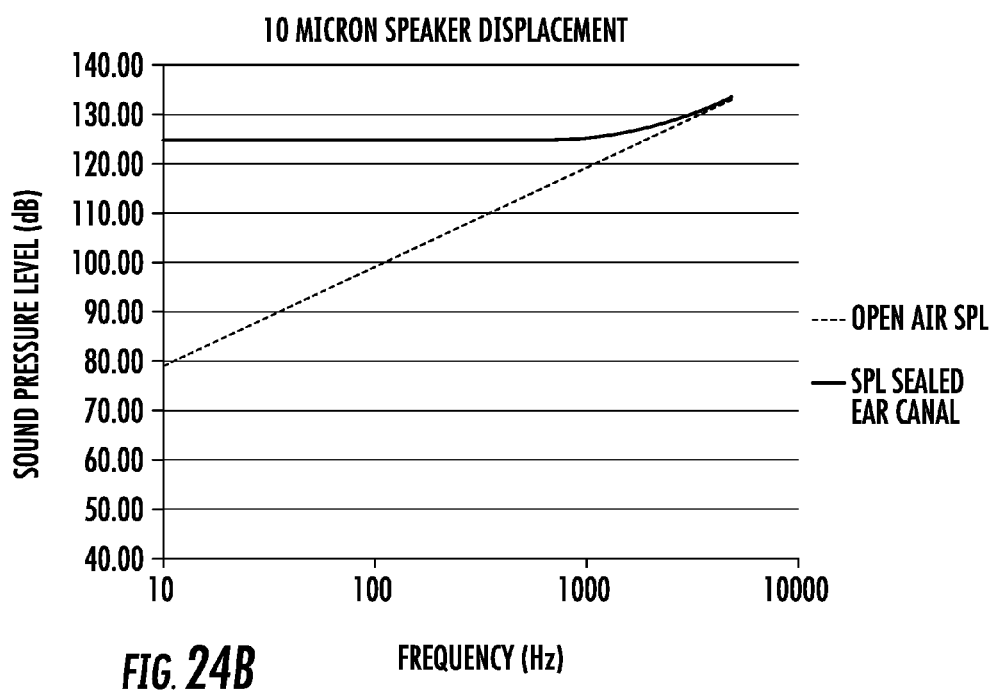
Figure 24C:
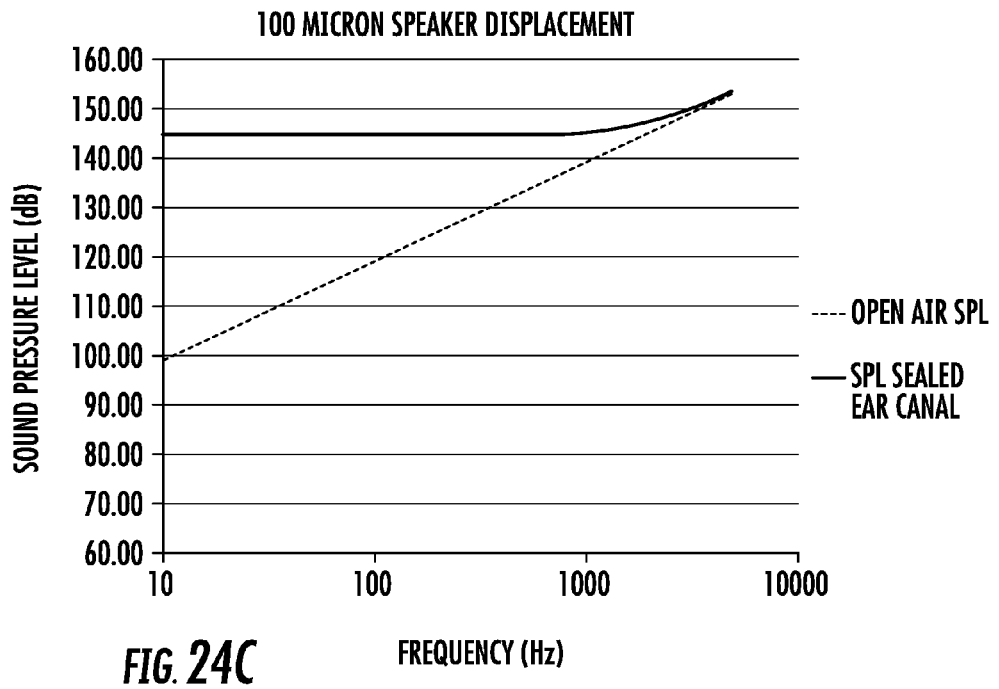
Figure 25A:
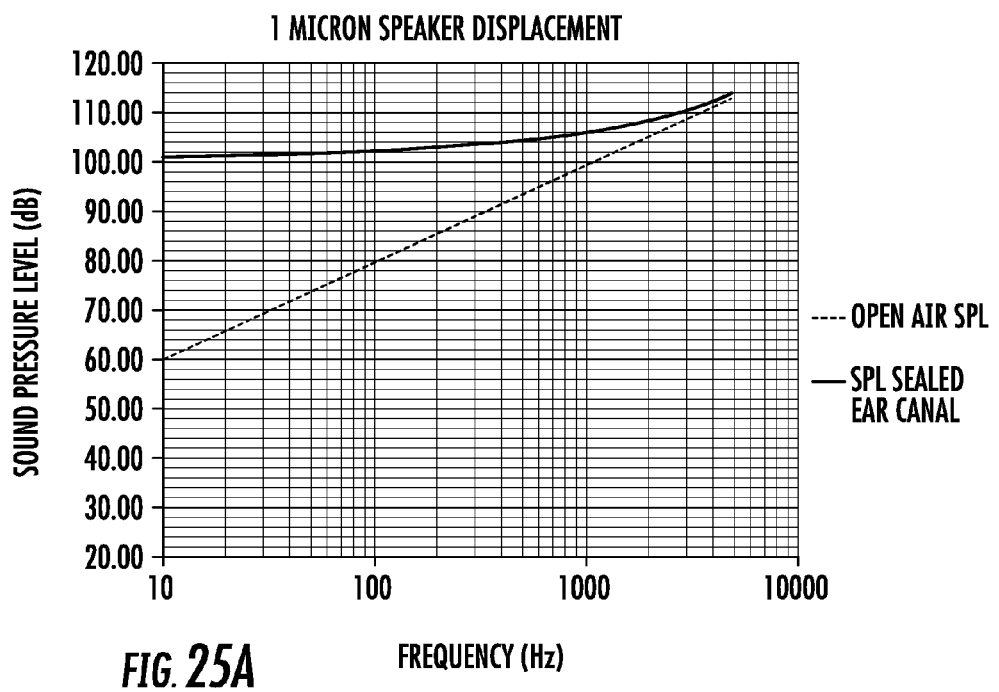
FIGS. 25(*a-c*) are graphs showing open air and sealed ear SPL data along a range of frequencies for 1, 10 and 100 micron speaker displacements as measured by a probe of the present invention.
Figure 25B:
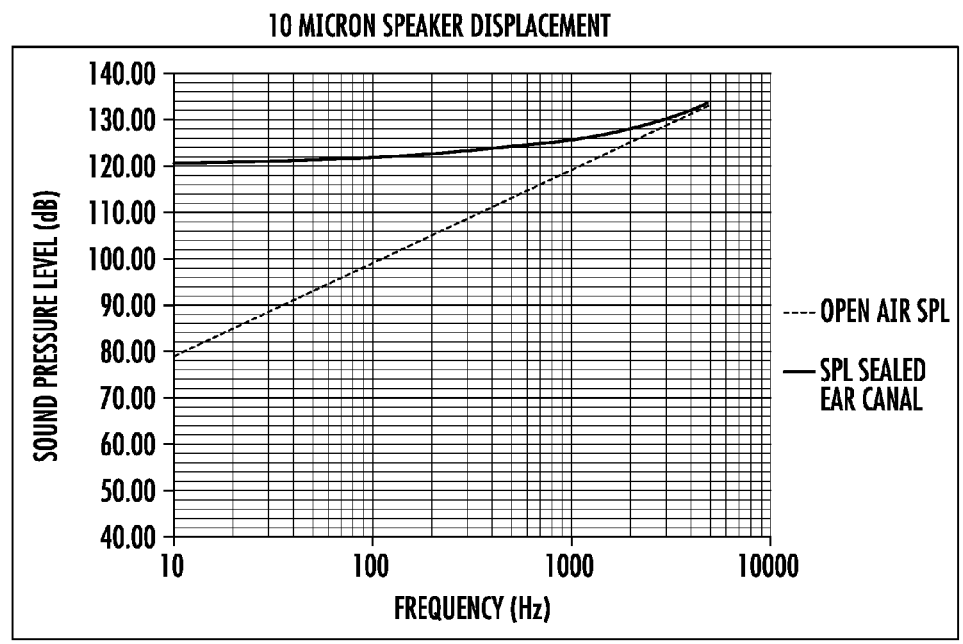
Figure 25C:
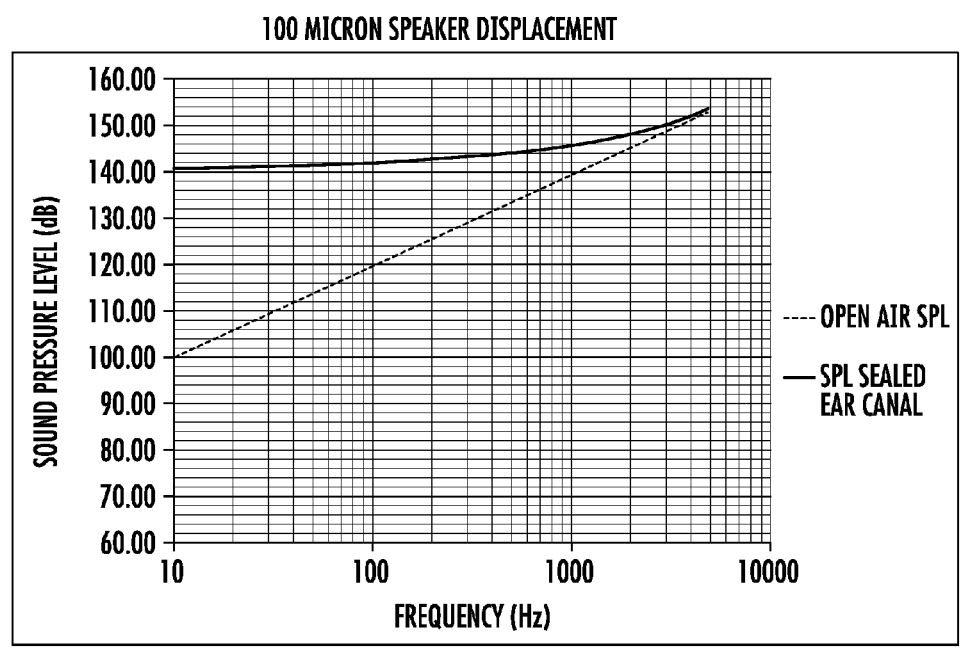

While this invention is susceptible of embodiment in many different forms, there is shown in the drawings, and will herein be described in detail, preferred embodiments of the invention, including embodiments of the various components of the invention, with the understanding that the present disclosure is to be considered as an exemplification of the principles of the invention and is not intended to limit the broad aspect of the invention to embodiments illustrated.

The large amplitude pressure oscillations resulting when a sound producing device is sealed in the ear canal produce a range of deleterious effects on the quality of the listening experience, and on listener comfort, and potentially on long term health (mainly hearing health, but also heath in general through the potential influences of exposure to infrasound). Of particular note are the trapped volume insertion gain (TVIG), large over-excursions of the tympanic membrane, 100 to 1000 times as large as in normal open air listening, and the triggering of the stapedius reflex, which reduces the sensitivity of the ear and may contribute to listener fatigue.

Some in-ear listening devices such as hearing aids and in-ear monitors for musicians require an acoustic seal in the ear to prevent feedback from nearby microphones. Thus it is not always desirable or possible to get rid of the static pressure oscillations and over-excursions of the tympanic membrane by breaking the ear seal or adding a vent to allow communication with the open air. It is therefore of great utility to invent new technology to mitigate the effects of oscillating static pressure and the resulting over-excursions of the tympanic membrane when a listening device is sealed in the ear.

This disclosure presents what is to our knowledge the first comprehensive recognition, integration and explanation of the effects described above. As such, we present and claim a full range of technologies, devices and approaches for detecting, and mitigating these problems.

The inventive theme, that runs through each of the embodiments presented below, is that a compliant surface added to some part of the enclosure creating the trapped volume in the ear canal acts to partially or fully alleviate oscillating static pressures, also referred to as alternating or changing pneumatic pressures, which are high in amplitude (and SPL) and which are as much as 90 degrees or more degrees out of phase with the velocity component of the otherwise unsealed sound waves, thereby allowing them to remain as normal sound waves which are lesser in amplitude which are more in phase with their velocity components. This then enhances speaker fidelity and reduces trapped volume insertion gain (TVIG) thereby alleviating premature triggering of the acoustic reflex, audio fatigue and potential hearing loss.

Figure 58:
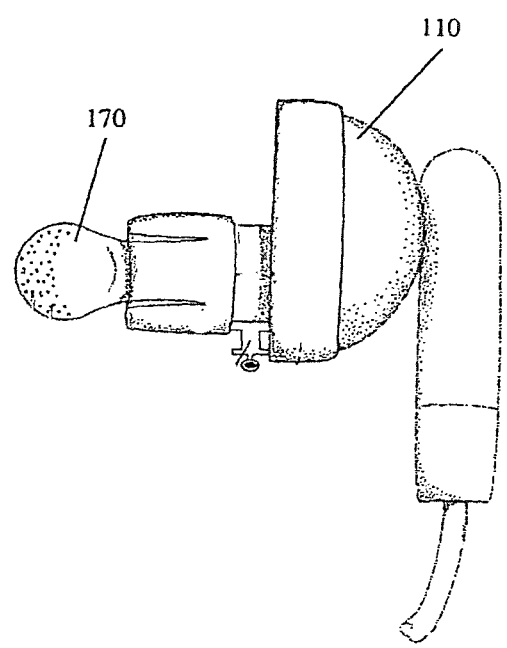
FIG. 58 is an image of an audio device with an inflatable member.

5.1 ADEL Ear Coupling Absorbs Static Pressure and Mitigates Tympanic Membrane Over-Excursions The ADEL inflatable seal for listening devices inserted into the human ear has been described in detail in our previous filings, as have the benefits of this device for comfort, and sound quality. In our first patent on this device, reference was made to static pressures in the sealed ear canal and the resulting over excursions of the tympanic membrane. In that patent application we made claims relating to the use of the inflatable ear seal as a means of lowering in-ear pressure and mitigating over excursions of the tympanic membrane. The detailed analysis in the current application clearly demonstrates the mechanism by which the inflatable bubble in the ear achieves these benefits. An inflatable bag shaped bubble 170 is shown in FIG. 58 on an ear bud with a transducer 110. The ADEL bubble is like a pneumatic shock absorber that deforms or flexes to relieve some of the static pressure build up, produced by the motion of the speaker, which is responsible for static pressure oscillations and tympanic membrane over excursions. When the speaker diaphragm moves forward into the trapped volume of the ear canal, the light and flexible bubble seal can retract slightly to negate some of the volume change and reduce static pressure buildup. One previously claimed embodiment of the ADEL bubble, a slightly under-inflated bag-like structure made of a non-extensible material such as expanded polytetrafluoroethylene (ePTFE), is ideal for performing this function. Thus we disclose the use of the inflatable ear seal as a means for reducing trapped volume insertion gain, and for preventing insert headphones or hearing aids from triggering the stapedius reflex. The compliance of the inflatable bubble seal acts to partially or fully transform oscillating static pressures, which are high in amplitude (high SPL) and are 90 degrees out of phase with the velocity component of the sound waves, into normal sound waves which are lesser in amplitude and are more in phase with their velocity components.

Figure 59:
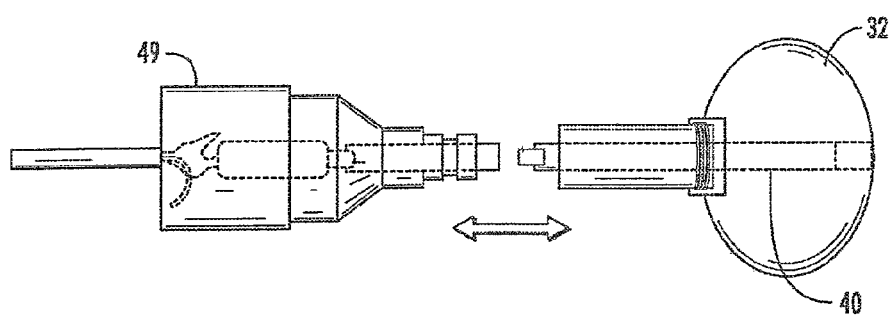
FIG. 59 is an image of an audio device with another form of an inflatable bubble.

Two major classes of the inflatable ADEL ear seal have been previously described: the donut bubble, in which there is an open sound tube piercing the middle of the inflatable seal providing a direct connection between the speaker diaphragm and the trapped volume in the ear canal; and the driven bubble, in which the inflatable member completely encloses the end of the sound tube. In the driven bubble embodiment, the speaker impinges upon a closed volume comprising the interior of the driven bubble, and this volume is separated by the bubble wall from the volume sealed in the ear canal. Both of these ADEL embodiments provide the mitigation and transformation of oscillating static pressure into normal acoustical waves as well as reduction in TVIG and reduction in the stapedius reflex. An inflatable donut shaped bubble is shown in FIG. 59 at 32 around a sound tube 40 mounted on a housing 49.

Additionally, both the donut bubble and driven bubble versions of the inflatable ADEL ear seal transduce sound energy directly into the ear canal wall. Direct transduction of sound through the ear canal walls and through tissue and bone directly to the cochea provides a path for sound energy that does not involve over-excursions of the tympanic membrane, and is therefore less likely to stimulate the stapedius reflex. Embodiments of the device may be used in noise cancellation applications. The alternate transduction paths which are traveled by the acoustic vibrations which enter the head through the eyes, nose, pharynx, sinus cavities, flesh covering of the face and head, etc. when the listener experiences external sound sources can be effectively damped by the transduction of these same vibrations emanating from the expandable bubble portion 170 directly out of phase and at the appropriate volume levels and audio frequencies necessary to noise cancellation. This affords effective hearing protection and isolation schemes which were never before possible. While ear plugs or muffs can dampen excessive noise pollution traveling down the ear canal, OSHA still warns of hearing damage which occurs through alternate transduction paths to the cochlea. Short of heavy enclosed helmets, no portable technology has existed which mitigates these dangers. Through noise cancellation via transduction schemes, embodiments of the acoustic device may offer many unique and vital sound isolation and noise protection applications.

Driven bubbles that fit loosely into the ear canal, and thus do not produce an acoustic seal, can provide protection from the effects of high SPL. such as the stapedius reflex and audio fatigue, when used with open ear devices, such as open architecture RIC hearing aids, and unsealed headphones. The driven bubble creates a closed volume including the speaker and the sound tube (if present). Large static or acoustical pressure oscillations are contained in the bubble. Depending upon the properties of the bubble material and its condition of inflation, this bubble may be used to manage the re-radiation of sound into the ear canal at a more controlled SPL, and without static pressure effects. This has the benefit of reducing the likelihood that the stapedius reflex is triggered.

5.2 Covered Vents and Bubbles Absorb Static Pressure, Mitigate Tympanic Membrane Over-Excursions, and Prevent the Stapedius Reflex in Headphones and Hearing Aids Some in-ear hearing devices require an acoustic seal isolating the ear canal from the outside air. Such devices are subject to the problems of static pressure oscillations, tympanic membrane over-excursions, and triggering of the stapedius reflex, as discussed above. Simply putting a vent or hole in the ear seal to prevent static pressure build up is not, in some cases a viable alternative because the device will feedback. Here we claim the invention of a vent in an ear seal that is covered by a thin flexible membrane. This covered vent allows the relief of static pressure build up (including both positive and negative pressures), through deformation of the thin flexible membrane. This deformation of the covering of the vent may include expansion or contraction; bowing out or bowing in; and performing these motions as vibrations at acoustical frequencies. Alternatively the function of the covered vents may be described as the radiating of acoustical energy out of the sealed volume of the ear canal. Either description leads to the same function for the covered vents: to reduce pressure and SPL in the ear canal so as to reduce over excursions of the tympanic membrane and to prevent to stapedius reflex. A wide range of vent geometries, numbers of vents, and the like are possible on a wide range of ear sealing devices. Vents filled with bubbles containing air or some other compliant filling can perform the same function as vents covered with thin flexible membranes. Some examples are given below:

5.2.1 Insert Ear Tip with Covered Vents

Figure 41A:
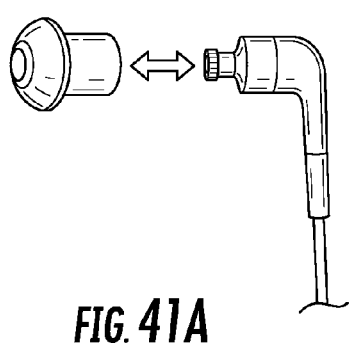
FIG. 41(*a,b*) are images showing a typical commercial form of an earbud construction.
Figure 41B:
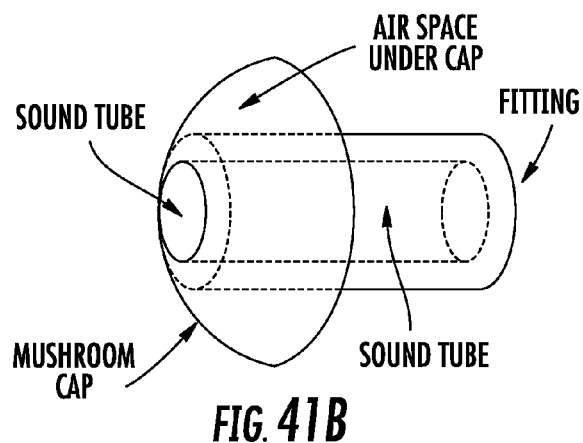

Ear buds or insert headphone tips of the sort shown in FIG. 27 often have structures as illustrated in FIG. 41. FIG. 41a shows how the insert headphone tip slips over the snout of the earphone body. FIG. 41b shows the structure of a typical insert headphone tip. A hollow, sound tube connects the sound source in the earphone body, through the ear tip, into the ear canal. The acoustic seal is provided by a "mushroom cap" structure which flares out around the end of the sound tube facing into the ear canal. There is an open (air filled) space underneath the mushroom cap, i.e. between the underside of the mushroom cap and the outside of the sound tube.

FIG. 42 shows one set of embodiments of the present invention. FIG. 42a shows an embodiment with a single hole in the sound tube. This hole is covered by a flexible membrane material. The hole in the sound tube, along with its covering, comprises a covered vent, as described above. FIG. 42b shows an embodiment in which a number of such covered vents are distributed around the circumference of the sound tube. Embodiments of this invention, with respect to the number, geometry and placement of covered vents, are not limited by FIG. 42. For instance, multiple covered vents may be distributed along the length of the sound tube, instead of, or in addition to around it circumference. Covered vents need not be circular holes, as in FIG. 42. They may have any other suitable shape including (but not limited to) slits, square, rectangular, triangular, or oval holes. The flexible membrane material covering the vents may be a polymeric membrane, or another membrane material including a lightweight metal foil or a metal covered polymer membrane. The flexible membrane covering the vents may be any one of the materials or classes of materials from which ADEL bubble can be produced, and which are listed in our previous patent filings. In FIG. 42, the covered vents in the sound tube are shown to be under the mushroom cap of the insert ear tip. This is not a requirement of the invention. These vents may be anywhere along the sound tube, however, placement under the mushroom cap is potentially desirable both esthetically and as a protection for the membrane coverings of the vents.

Figure 42A:
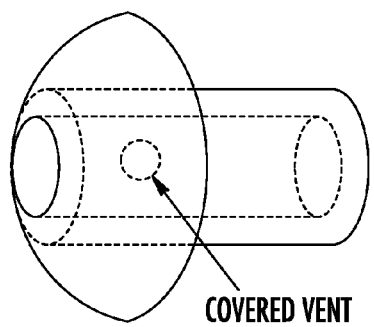
FIGS. 42(*a-h*) are images of earbud tips showing different embodiments made in accordance with the invention of the present application.
Figure 42B:
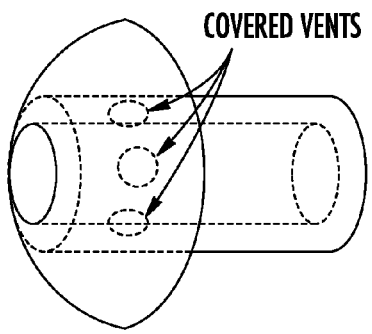
Figure 42C:
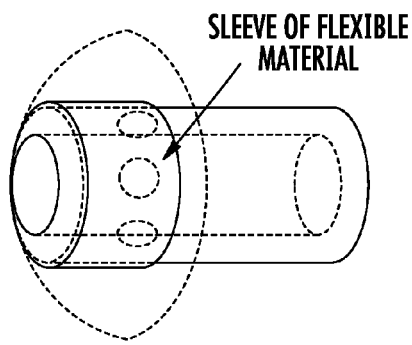

FIG. 42c shows an embodiment in which the covered vents, are not individually covered, as in FIGS. 42a and b, but rather are collectively covered by a snug fitting sleeve of the flexible membrane material, which surrounds a section of the outside of the sound tube.

Figure 42D:
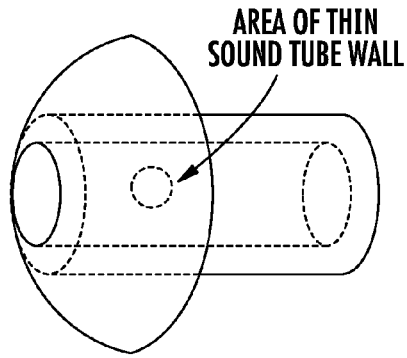
Figure 42E:
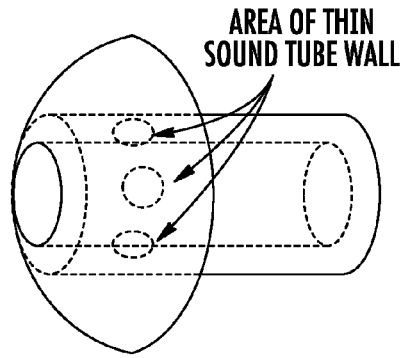

FIGS. 42d-h show embodiments in which the insert ear-tip with covered vents is molded as a single piece of polymeric material. This single molded piece includes the vent holes and the vent covers. This is accomplished by molding holes into the sound tube that do not penetrate all the way through the sound tube wall, leaving a very thin membrane of the same material that composes the sound tube covering the hole. This membrane of molded material is thinner than the wall thickness of the sound tube, and is preferably thinner than 100 micrometers, and is most preferably thinner than 40 micrometers. The remaining membrane of molded material covering the hole may be flush with the inside of the sound tube. It may be flush with the outside of the sound tube, or it may be at any other location throughout the depth of the hole(s) penetrating the sound tube. FIG. 42d shows an embodiment with a single hole in the sound tube, which thins the wall of the sound tube but does not penetrate all the way through the sound tube. FIG. 42e shows an embodiment with a number of such holes covered by films of the same molded material as the sound tube.

Figure 42F:
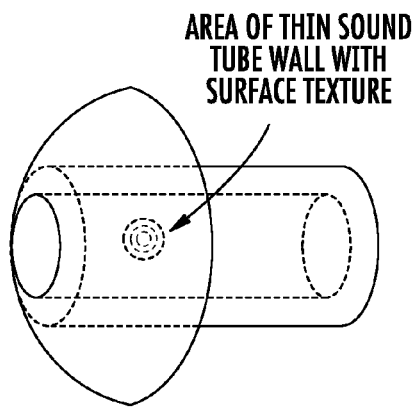
Figure 42G:
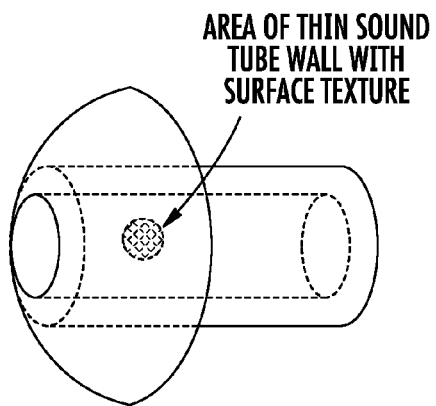
Figure 42H:
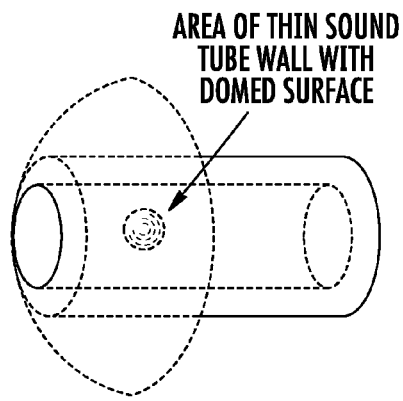

The membrane of molded material covering the hole(s) in the sound tube may be smooth, as in FIGS. 42d and e, or it may be textured or embossed as in FIGS. 42f and g. The texture may be concentric circles (FIG. 42f), a spiral, a dimpled or wrinkled pattern (FIG. 42g), or some other pattern or texture. Additionally, as in FIG. 42h, the thin membrane(s) of molded material may be a dome shaped and they may be convex (sticking out from the sound tube) or concave, sticking down toward the center of the sound tube.

All insert headphone ear tips with covered vents or other embodiments of this invention are designed with an elastic boot fitting that allows them to fit over the snout of virtually any commercially available insert headphone, as shown in FIG. 41a.

FIG. 43 shows an embodiment in which the pressure relieving function of the covered vents is adjustable. A snug fitting sleeve of a more rigid material covers the vents in the sound tube. The vents themselves are still covered by the flexible membrane material, either individually or via another sleeve of this flexible membrane material, which is beneath the sleeve of rigid material. There are holes in the outer, rigid sleeve which correspond in size and arrangement to the underlying covered vents in the sound tube. The entire outer, rigid sleeve can be rotated around the sound tube to either align (FIG. 43a), partially misalign (FIG. 43b) or completely misalign (FIG. 43c) with the underlying covered vents in the sound tube. When the holes in the outer, rigid sleeve are completely aligned with the covered vents, as in FIG. 43a, the covered vents function to their maximum pressure relieving capacity. When the holes in the outer, rigid sleeve are partially aligned with the covered vents, as in FIG. 43b, the covered vents function at a reduced pressure relieving capacity. When the holes in the outer, rigid sleeve are completely misaligned with the covered vents, as in FIG. 43c, the covered vents do not function to relieve pressure in the trapped volume. FIG. 43d shows another embodiment in which the holes in the outer sleeve are not open, but are themselves covered with a flexible material. The alignment or partial misalignment of this outer covered vent, over the inner covered vent, alters the pressure relieving and acoustical properties of the composite structure. The rigid, outer sleeve in FIG. 43 may be fitted with a manually operated handle or switch (not shown) that allows the user to adjust the alignment of holes and covered vents. The rigid outer sleeve may also fit into a coupling on the body of the headphone (not shown) when the ear tip is attached, as in FIG. 41a, and then the alignment of holes and covered vents may be controlled by a manual or power driven motion transmitted from the headphone body.

Other methods, besides the alignment of holes over the covered vents, may be used to adjust the pressure relieving response of the covered vents. These other methods include, but are not limited to, mechanisms by which the flexible membrane material covering the vents is stretched (tensioned) or allowed to relax. This may be done individually on membranes covering individual vents, or collectively by adjusting the fit or tension of a sleeve or other piece of the flexible membrane material covering a number of holes, as in FIG. 42c.

The sleeve of flexible membrane material (FIG. 42c) and the rigid, outer sleeve with holes (FIG. 43) have been shown on the outside of the sound tube. They can also be placed on the inside of the sound tube and perform the same function. For instance, the inside of the sound tube may be covered with a cylindrical lining of the flexible membrane material in the region of the vents. Additionally, a rigid, cylindrical, inner sleeve with holes in it can be inserted into the sound tube rotation of this inner cylinder to align or misalign its holes with the covered vents in the sound tube can perform the same pressure relief adjustment as the device shown in FIG. 43.

Figure 43A:
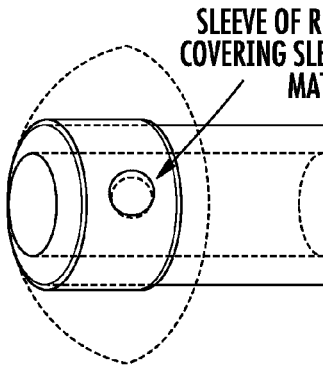
FIGS. 43(*a-f*) are images of earbud tips showing different embodiments made in accordance with the invention of the present application.
Figure 43B:
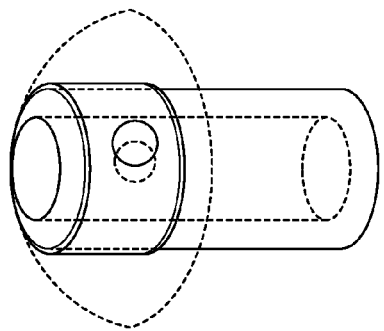
Figure 43C:
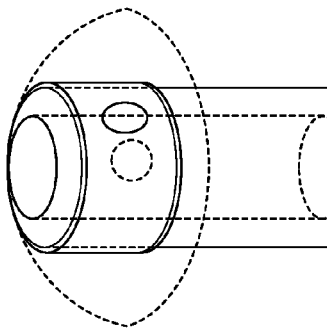
Figure 43D:
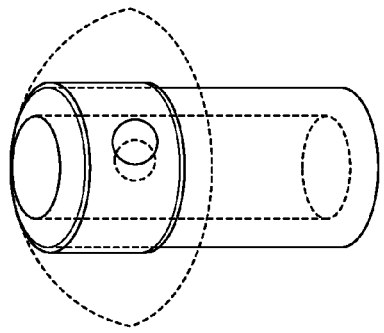
Figure 43E:
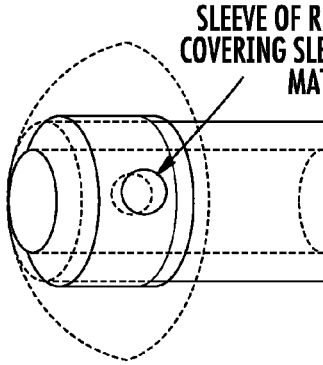
Figure 43F:
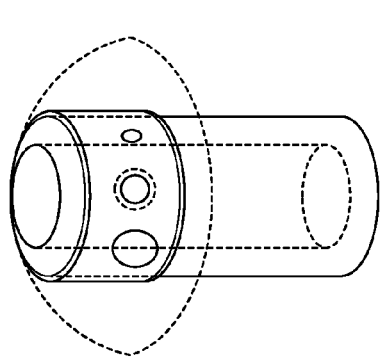

FIG. 43e shows an embodiment similar to FIGS. 43a-c, but with the difference that the sleeve of rigid material slides along the sound tube, rather than rotates, in order to align or misalign holes with covered vents. The sliding, rather than rotation sleeve, can be used either on the outside of the sound tube as shown in FIG. 43e, or on the inside of the sound tube (not shown). FIG. 43f shows an embodiment in the holes in a rotating sleeve of rigid, or semi-rigid, material have different sizes. The use of different sized holes may be used, rather than alignment and misalignment as in FIGS. 43a-c, as a means to adjust the activity of the covered vents in the sound tube. The sleeve with the different sized holes may be outside the sound tube, as shown in FIG. 43f, or it may be inside the sound tube. The different sized holes may be changed by rotation of the sleeve, as shown in FIG. 43f, or be sliding analogous to FIG. 43e.

All of the embodiments of FIG. 43 could also be constructed with the covered vents located in the rotating or sliding rigid (or semi-rigid) sleeve (placed inside or outside the sound tube). In these embodiments, there would be holes in the sound tube, which are either aligned or misaligned with the covered vents in the moving sleeve.

5.2.2 Insert Ear Tip with Closed Bubbles

The function of relieving static pressure build up in the sealed volume comprising the ear canal and the sound tube can also be accomplished, as shown in FIG. 44, by placing gas filled bubbles, or bubbles filled with some other suitably compliant fluid (such as a liquid or gel), in the wall of the sound tube or within the interior of the sound tube.

Figure 44A:
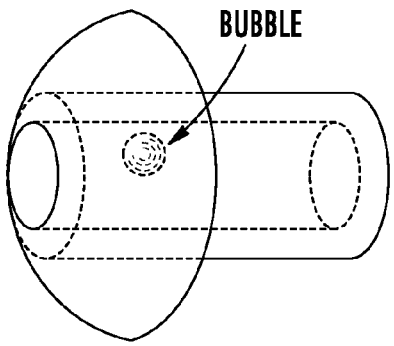
FIGS. 44(*a-e*) are images of earbud tips showing different embodiments made in accordance with the invention of the present application.
Figure 44B:
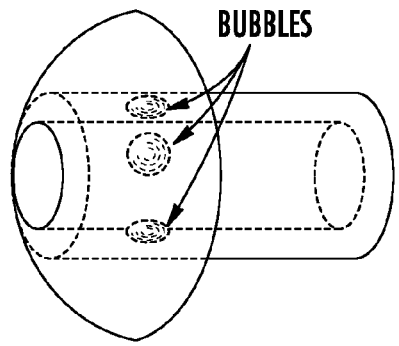
Figure 44C:
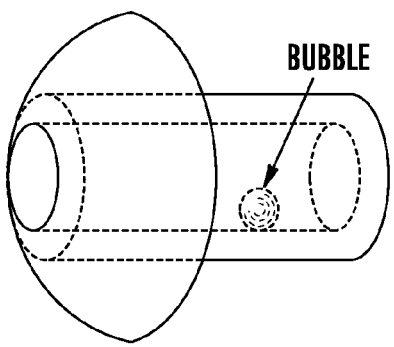
Figure 44D:
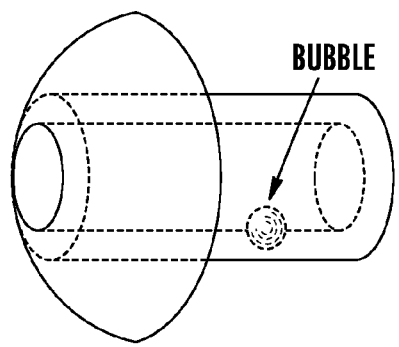

FIG. 44a shows an embodiment with a single bubble in the wall of the sound tube. The surface of the bubble is made of the same type of flexible membrane material as the vent covers discussed in the previous section. The interior of the bubble may contain a gas, which would commonly be air, but could be another gas such as helium, nitrogen, oxygen, argon, or the like. The interior of the bubble may also contain another fluid or compliant material such as a liquid or a gel. The bubble, in this embodiment, spans the wall of the sound tube, with part of the bubble surface exposed to the interior space of the sound tube and part of the bubble surface exposed to the outside of the sound tube. FIG. 44b shows an embodiment in which multiple bubbles, of the type in FIG. 44a, are distributed in the sound tube wall. FIG. 44c shows an embodiment in which a bubble of the same type is enclosed completely within the sound tube. Other versions of this embodiment may have multiple bubbles enclosed completely within the sound tube. Another working embodiment, FIG. 44d, has a bubble or bubbles, imbedded in the inner wall of the sound tube. These bubbles must have some of their flexible membrane outer surface exposed to the interior of the sound tube. The rest of the bubbles' surface is encased in the wall of the sound tube, and the bubble surface does not contact the space outside the sound tube.

Figure 44E:
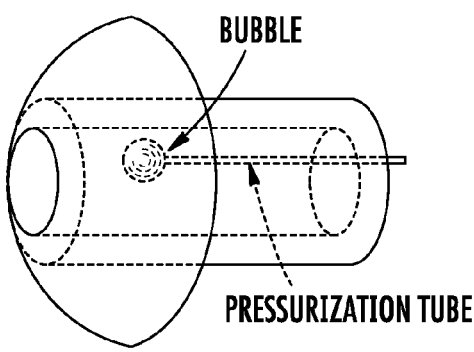

The bubbles may be fully inflated or they may be under-inflated so that the membrane material enclosing them is loose. This loose bubble covering may be wrinkled. The static pressure relieving function of the bubble(s) may be adjustable via an adjustment of pressure in the bubble through a pressurization tube, as shown in FIG. 44e. Embodiments with multiple bubbles may have multiple pressurization tubes, and may have a pressurization manifold that feeds multiple variable pressurization bubbles. The pressure relieving function of the bubbles may also be adjustable by partially covering their surfaces where they contact the interior of the sound tube or the space outside the sound tube. One embodiment that achieves this uses a rigid or semi-rigid, rotating sleeve with holes in it (as in FIG. 43), but now applied over bubble filled openings in the sound tube. Other means of covering part or all of the bubbles' surfaces are equally valid embodiments of this invention.

Figure 55:
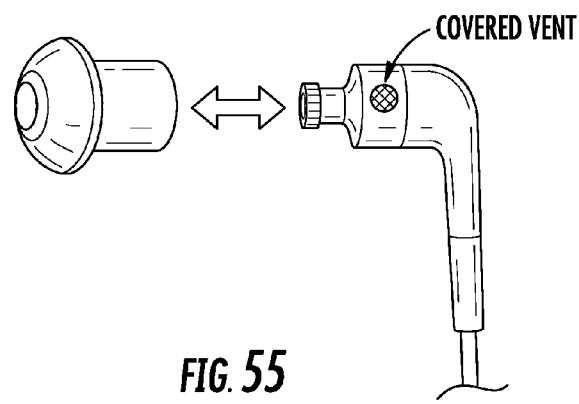
FIG. 55 is an image illustrating an embodiment of an earbud and headphone tip made in accordance with the present invention.

The covered vent or vents may also be placed in the hard plastic or metal case of the earbud which forms part of the front volume of the speaker and to which the rubber mushroom ear-tip attaches. FIG. 55 shows such a covered vent on an earbud case. As with other embodiments discussed, there may be one, two or more such covered vents around the case of the earbud. They may be circular in cross section or some other shape, including, but not limited to, oval, rectangular, tear drop, etc. The covered vents on the earbud case may be covered with a sleeve with holes in it in order to allow the user to adjust the influence of the covered vents. The holes in the sleeve may be any shaping, including circular, oval, rectangular, tear drop, etc. All of the schemes for arrangements of covered vents and a sleeve to adjust their effect, which were shown for use around the sound tube, may also be applied to the rigid case/housing of the earbud, where that case covers the front volume of the speaker.

Figures 56A, 56B, 56C, 56D:
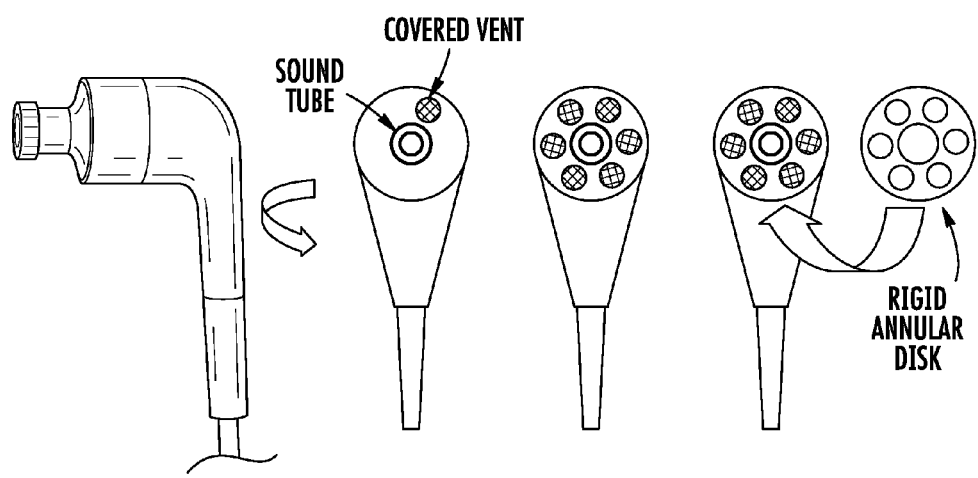
FIGS. 56(*a-d*) are images illustrating embodiments of a headphone tip made in accordance with the present invention.

The covered vents on the front volume of the earbud casing may also be placed on the front of the casing as shown in FIGS. 56(a-d), rather than on the side of the earbud casing, as shown in FIG. 55. One or more covered vents may be placed on the front of the earbud casing around the sound tube. These covered vents may also be covered by an annular disk of more rigid material having holes therein. This annular disc may be rotated to expose different amounts of covered vent surface are with the holes of the annual disc. This allows the user to adjust the amount of oscillating static pressure and thus the acoustical characteristics of the earbud. The covered vents themselves and the holes in the annual disk may be any convenient shape including, but not limited to, circular, oval, rectangular, tear drop shaped, etc.

The covered vents used in the inventions disclosed in this application may be constructed by placing a flexible membrane material, such as expanded polytetrafluoroethylene (ePTFE), over one end of a short cylinder, hoop, or islet, as shown in FIG. 57a. This allows for easy insertion into holes in the sound tube or the housing of the earbud.

Additionally, as shown in FIG. 57b, the short cylinder, hoop, or islet may be covered by a rigid surface, parallel to the compliant membrane, and this rigid surface may contain one or more ports (holes). These ports allow airflow to facilitate the movement of the compliant membrane, while adjusting the acoustical performance of the device.

5.2.3 Application to Over-Ear Head Phones

To the extent that over-ear headphones fit snuggly to the sides of the head, they can create a trapped volume that is continuous with the ear canal. Sealed, or partially sealed, over-ear headphones therefore can also subject the tympanic membrane to large amplitude static pressure oscillations resulting in over-excursions of the tympanic membrane. The effect is not as pronounced as in inert headphones due to the much larger size of the trapped volume. However, listener comfort and safety, as well as sound quality can still be enhanced by adding static pressure relieving elements, as shown in FIG. 45.

FIG. 45a shows over ear headphones with a covered vent in the wall of the ear enclosure. This covered vent is a hole connecting the interior of the enclosure with an outside that is covered by a flexible membrane material. The membrane material is from the same group as listed previously for covered vents in insert headphones. There may be one vent or multiple vents, of varying size and shape, and varying arrangement. These vents may be covered or partially covered by an adjustable cover of greater rigidity than the flexible membrane, analogous to the scheme of FIG. 43, for the purpose of allowing adjustment to the pressure relieving properties. These bubbles or vents may be in direct contact with the outside air or may face into a cavity inside the outer housing (can) of the headphone as long as this space is, in-turn vented to the outside atmosphere.

FIG. 45b shows over ear headphones with a bubble in the wall of the ear enclosure. This bubble may have free surfaces in contact with the interior of the enclosure and with the outside (either directly or through contact with another vented space), it may be embedded in the enclosure wall and thus only be in contact with the interior space, or it may be completely contained in the ear-enclosure of the headphone.

There may be bubble or multiple bubbles, of varying size and shape, and varying arrangement. The pressure relieving function of the bubbles may be adjustable by partially covering their surfaces where they contact the interior of ear-enclosure or the space outside the enclosure. The bubble(s) in the headphone of FIG. 45b may be fully inflated or they may be under-inflated so that the membrane material enclosing them is loose. This loose bubble covering may be wrinkled. The static pressure relieving function of the bubble(s) may be adjustable via an adjustment of pressure in the bubble through a pressurization tube (not shown). Embodiments with multiple bubbles may have multiple pressurization tubes, and may have a pressurization manifold that feeds multiple variable pressurization bubbles.

In another embodiment a toroidal or donut shaped bubble completely surrounds the inside of the earphone on the inside of the foam enclosure which surrounds the ear. In another embodiment, a toroidal or donut shaped bubble completely surrounds the inside of the earphone taking the place and performing the function of the foam enclosure that surrounds the ear.

5.2.3 Covered Vents in the Outer Housing of a Balanced Armature Transducer

Figure 46A:
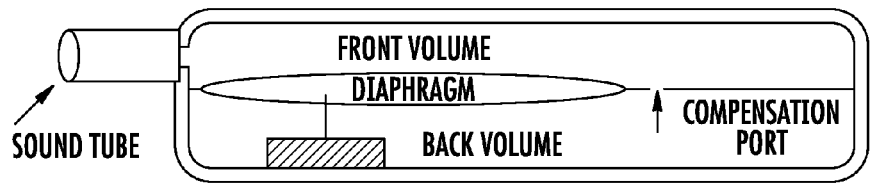
FIGS. 46(*a-d*) are images of embodiments of a balanced armature transducer made in accordance with the invention of the present application.
Figure 46B:
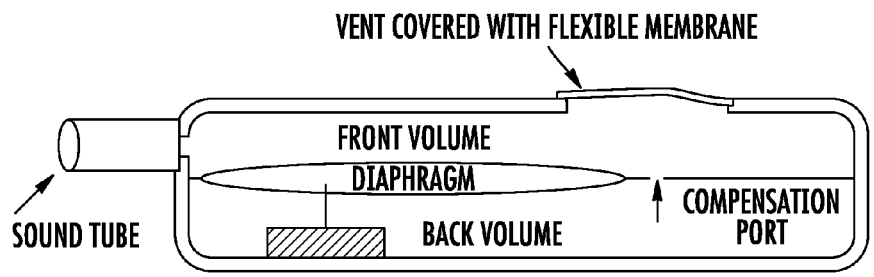

Devices such as professional in-ear monitors, high end insert headphones, or a receiver in canal (RIC) hearing aids use balanced armature transducers as their sound sources. As shown in FIG. 46a, the open space on the front side of the diaphragm, but within the outer housing or case of the balanced armature transducer is known as the Front Volume. When a device using one of these transducers (receivers) is sealed in the ear canal, the Front Volume is part of the trapped air volume which includes the sealed part of the ear canal. Placing a covered vent, as shown in FIG. 46b, in the outer housing of the balanced armature transducer that can relieve static pressure and radiate acoustical energy in the front volume is another embodiment of the inventive technology of this disclosure. This covered vent can reduce oscillating static pressure, reduce trapped volume insertion gain, and prevent the triggering of the stapedius reflex. There may be one or multiple covered vents in the outer housing of the balanced armature transducer and these vents may be arranged in any location as long as they access or partially access the front volume of the transducer. As in the other embodiments disclosed above, closed bubbles in the outer housing of the front volume or fully or partially contained in the front volume may also be used to achieve these benefits.

Figure 46C:
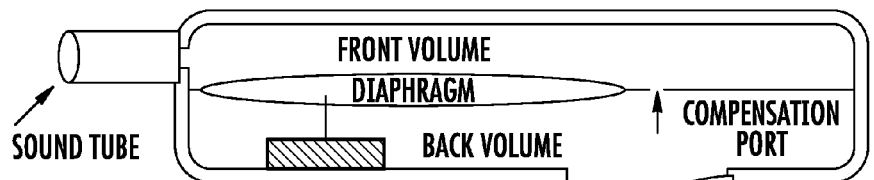

FIG. 46c shows a balanced armature transducer with a vent covered with a flexible membrane in its back volume. This location of the covered vent does not reduce static pressure in the ear canal, does not reduce trapped volume insertion gain, and does not prevent the triggering of the stapedius reflex. The device shown in FIG. 46c is a separate invention that allows the transducer to operate acoustically and mechanically as if its back volume is much larger than the actual space it occupies. This allows improved speaker performance and eliminates that need for a tuned vent or port in the back volume. Such a vent or port may be disadvantages because it can cause feedback. There may be one or multiple covered vents in the outer housing of the balanced armature transducer that access the back volume and these vents may be arranged in any way and in any location.

Figure 46D:
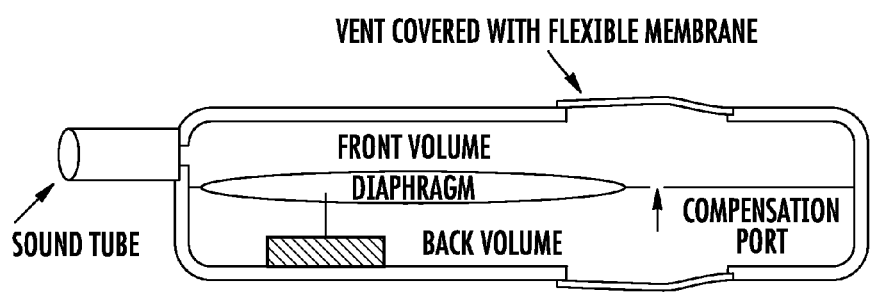

FIG. 46d shows an embodiment in which there are vents covered with flexible membranes in both the front volume and the back volume of the balanced armature transducer. This embodiment allows the advantages of increased effective back volume as in FIG. 46c, while also reducing static pressure in the trapped volume of the ear canal, reducing trapped volume insertion gain, and mitigating the stapedius reflex.

5.2.4 Hearing Aid Embodiments

Hearing aids that seal in the user's ear produce the same undesirable trapped volume effects (high pressures and over-excursions of the tympanic membrane) inset headphones. The strategies based on adding covered vents or bubbles into the ear seal, the sound tube, the diaphragm, or the outer housing of the front volume of a balanced armature transducer, all apply to hearing aids.

Figure 47A:
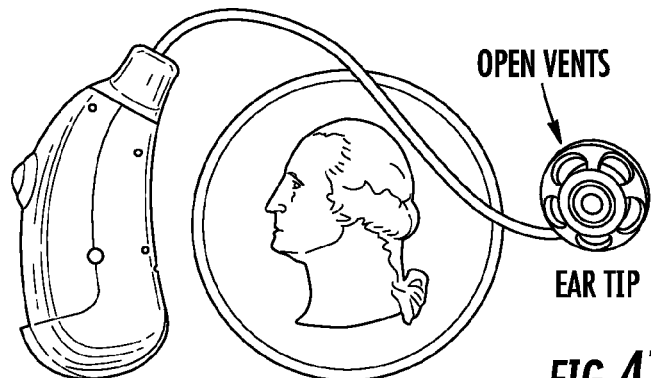
FIG. 47(*a,b*) are images showing a hearing aid tip as it might be modified in accordance with the invention of the present application.

FIG. 47a shows a commercial, receiver in canal (RIC) type hearing aid with an open-ear architecture. As indicated in the FIG., this device includes open-hole vents in the ear tip. This type of device is not suitable for people with severe hearing loss because feedback caused when large amplifications are used. This device can be modified according to this invention by placing thin flexible membranes over the vent holes in the ear tip. Alternatively gas filled bubbles could be placed in these holes, or these holes could be closed and a sealed vent or bubble could be placed in the diaphragm of the receiver in the ear tip. RIC devices like this generally use balanced armature transducers, and thus this device could also be made to practice our invention by putting a covered vent or vents or a bubble or bubbles in the front volume.

Figure 47B:
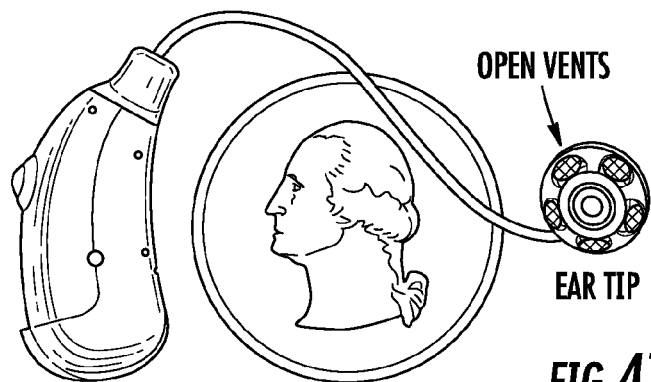

A hearing aid with covered vents in the ear seal, as shown in FIG. 47b, (or another embodiment of the present invention) will have greatly reduced insertion gain (which is related to the trapped volume insertion gain measured in this disclosure), thus making at least one of the adjustments that an audiologist performs when fitting a hearing aid to a patient, un-necessary. Thus the present invention will aid the development of hearing aids which do not need professional fitting, but still perform well. This development will greatly decrease the cost and increase the availability of hearing aids.

5.2.4 Laboratory Demonstration of the Efficacy of the Invention

The Skullcandy™ insert ear tips, analyzed above in Section 4, were modified in accordance with this invention and retested.

Figure 48A:
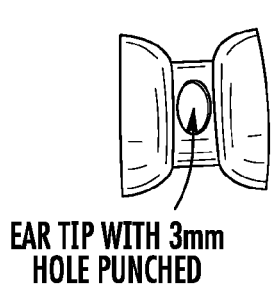
FIGS. 48(*a-c*) are images illustrating the modification of a earbud in accordance with an embodiment of the present invention.
Figure 48B:
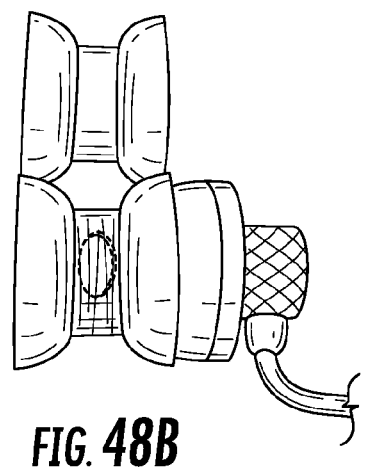
Figure 48C:
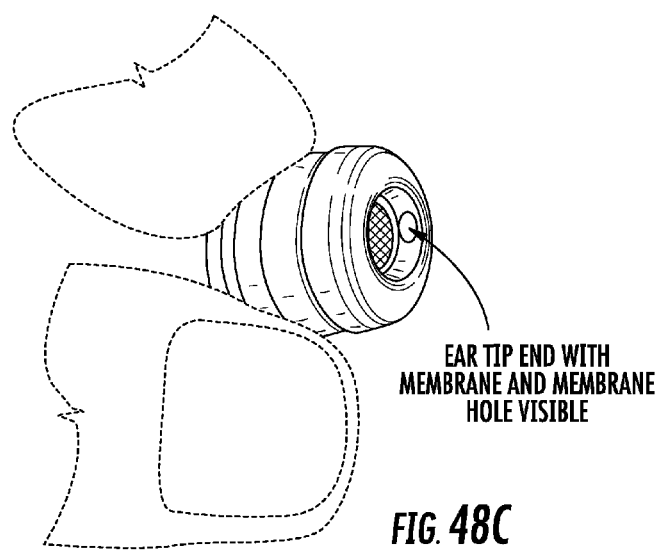

FIG. 48a shows a Skullcandy™ ear tip on a wooden mandrel with its mushroom cap turned up. A 3 mm diameter hole has been punched into its sound tube. On the upper left, a sleeve of expanded polytetrafluoroethylene (ePTFE), a light weight, flexible membrane material, is waiting to be used. FIG. 48b shows the Skullcandy™ ear tip with the ePTFE sleeve covering the hole in the sound tube, thereby creating a covered vent of the type disclosed in this filing. FIG. 48c shows the same modified ear tip with the mushroom cap turned down (its normal position). The ePTFE covered sealed vent is visible from the inside of the sound tube.

Figure 49A:
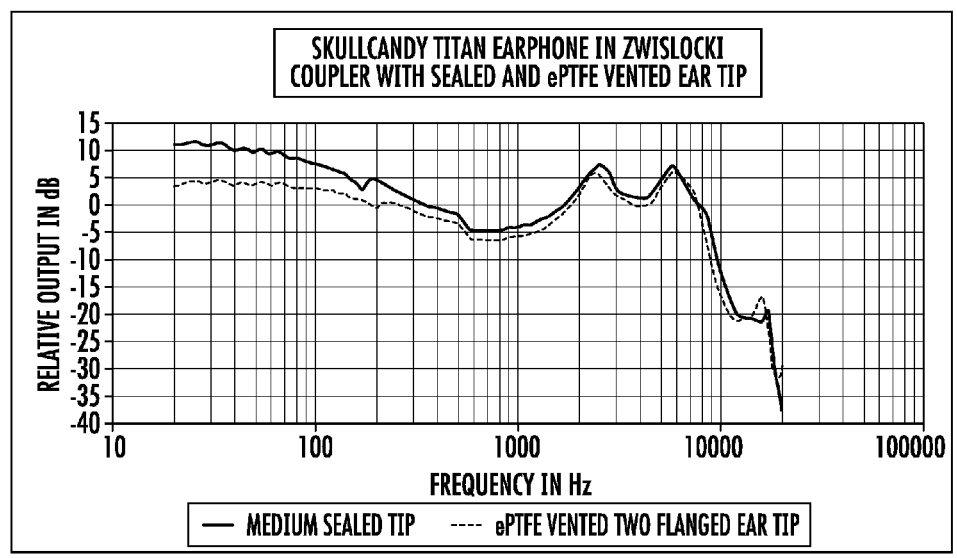
FIG. 49(*a,b*) are graphs showing data comparing the SPL of the device of FIG. 48 to that of a similar non-vented earbud tip.
Figure 49B:
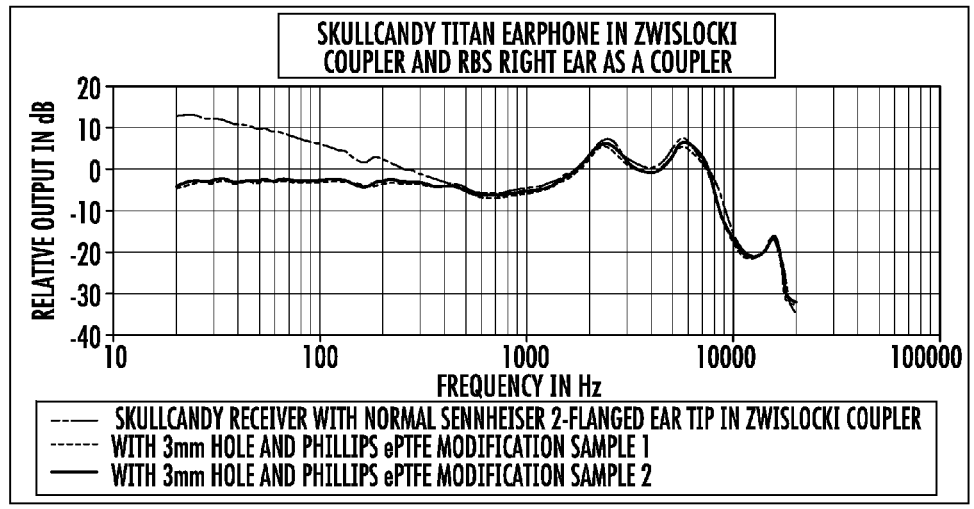

FIG. 49 shows the results of testing on this inventive ear tip with a covered vent. FIG. 49a shows the relative SPL vs frequency for the inventive ear tip as compared to the same type of ear tip without the covered vent, both sealed in a Zwislocki coupler. There is a clearly a marked reduction in relative SPL for frequencies below 3000 Hz, showing the inventive ear tip reduces static pressure oscillation in the ear canal, and therefore reduces SPL and over-excursions of the tympanic membrane. FIG. 49b shows similar experimental data comparing the inventive device sealed in a human ear vs. the unmodified ear tip. Again, the ear tip with covered vents is shown to reduce SPL, indicating a reduction in pressure in the ear canal and therefore and reduction in over-excursions of the tympanic membrane. Reductions of 5 to 20 dB were brought about by the inclusion of a single covered vent in the ear tip. This reduction in the trapped volume insertion gain has strong likelihood of preventing the stapedius reflex under normal listening conditions, and thereby preventing audio fatigue and potentially preventing long term hearing damage.
Use of Equalization to Reduce Trapped Volume Insertion Gain and to Prevent the Triggering of the Stapedius Reflex It is possible to consider using equalization or other frequency specific sound processing or volume control to reduce the amplitude of the lower frequency components of recorded audio material or of audio material as it is played real time by a device in the listener's ear. This may be done to counteract the effects of oscillating static pressure, trapped volume insertion gain, and the triggering of the stapedius reflex. We disclose the use of these techniques as part of our invention when used for the specific purpose of reducing trapped volume static pressure oscillations, and the triggering of the stapedius reflex.

The use of equalization and other electronic means of audio signal processing to achieve these ends has some efficacy, but we believe that it produces an inferior result to the inventive devices described above utilizing inflatable ear seals (ADEL), covered vents and bubbles. This is because the high amplitude oscillating static pressures that are the root cause of the problems are not simply confined to very low frequencies, but extend up through the prime range for voice and music. It is difficult to produce an equalization or mix that eliminates the oscillating pressure effects at these frequencies without also diminishing the desired material. The choice is to use a one size fits all equalization scheme to reduce TVIG, or to try to do the equalization real time on each new piece of program material. This, however, requires extensive sensing and signal processing which is generally not available in consumer devices. The inventive devices of this application provide a mechanical solution to this problem which naturally adjusts itself to the audio content and the individual.

The inflatable ear seal and the vented ear tips work better because they have an automatic sensing and response mechanism built in that allows them to respond to the static pressure oscillations while they are occurring and simultaneously allow the acoustical content to pass through. This actually performs a transformative function in which the static pressure oscillations are partially or fully converted into true acoustical waves. That is, the interaction of the oscillating static pressure with the compliant surfaces of the covered vents or the inflatable ear sealing bubble, or the bubbles in the sound tube, relieves or partially relieves the confinement that results in a 90 degree phase shift from ordinary sound waves. The inventive devices, thereby convert oscillating static pressure waves, or at least enough of this pressure to improve the listening experience, back into normal acoustical sound energy in which the pressure oscillation and the velocity component are in phase.

5.4 Consumer Device for Sensing and Displaying the High Pressures and High SPL in the Trapped Volume of the Ear Canal Additionally, devices for sensing higher pressure levels and high SPL levels in the trapped volume of the ear canal when a sound producing device is sealed in the ear canal are disclosed. These devices detect high pressures or high SPL though the use of a pressure sensitive material. This pressure sensitive material coated onto or incorporated into the surface or structure of a part or parts of the ear tip, ear seal, sound tube, etc. that is in contact with, or contiguous with, the trapped volume in the ear canal. This pressure sensing material undergoes a change when exposed to a given level of static pressure and/or SPL, and this change results in an indication of exposure to said pressure or SPL.

Examples of useful sensing materials for this application are piezoelectric materials that produce an electrical voltage when subjected to a pressure. A number of polymer (plastic) materials, suitable for incorporation into ear buds, insert eartips, headphones, and the like are piezoelectric, notably polyvinylidenefluoride (PVDF). A piezoelectric material incorporated into ear-tips may produce an electrical signal warning of high pressure or SPL which is picked up by connections on the headphone housing and transferred to a readout on the headset or on the electronic audio device. The electrical signal generated by high pressure or high SPL may also lead to a secondary effect, such as a change in color of the material, which warns the user.

Another example of a sensing material is a polymer or other material containing microscopic or nanoscopic vesicles, micelles, or other small containment vehicles (particles), that contain or sequester a dye or other chemical agent. These containment vehicles (vesicles, micelles, or the like) are engineered, based on their size and surface tension, to rupture at a given pressure or given SPL. Upon rupture the chemical content (dye, etc.) results in a change in properties of the overall material, which is noticeable. For instance, when a given pressure or SPL is exceeded, the material comprising the sound tube of insert headphones changes from clear/translucent to red or some other color.

These pressure or SPL sensitive ear tips, headphones, RIC hearing aid ear pieces, and the like may be designed for one time use, i.e. they turn color when exposed to dangerous pressure or SPL and they do not change back when the pressure or SPL is removed. Alternatively these pressure or SPL sensitive ear tips, headphones, RIC hearing aid ear pieces, and the like may produce a continuous readout of pressure level. This may be a two state readout indicating a dangerous level has been exceeded or not, and once the pressure or SPL is removed or lowered, the device may change back from its excited or warning state to its normal state. Alternatively the device may provide more detailed, ongoing indication of pressure or SPL level, either through an electronic readout or by some other change like progressing through a spectrum of colors.

5.5 Diagnostic Tool for Testing Whether Insert Headphones or Hearing Aids are Triggering the Stapedius Reflex.

Figure 50A:
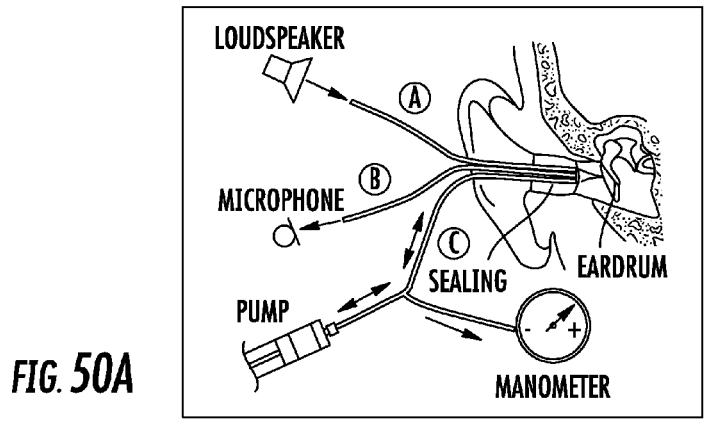
FIG. 50*a* is an image reproduced from "A Guide to Tympanometry for Hearing Screening" by T. K. Mikolai, J. Duffey, D. Adlin, MAICO DIAGNOSTICS, 7625 Golden Triangle Drive, Eden Prairie, Minn.

Audiologists use a version of tympanometry known as reflex tympanometry to study the stapedius reflex. FIG. 50a shows the general scheme of the insert ear-piece used for tympanometry. Three different tubes piece the ear seal to provide sound from a speaker, access for an external microphone, and pressure regulation via an external pump and manometer. This device, as shown, is not suitable for testing to see whether commercial insert headphones, ear buds, or hearing aids trigger the stapedius reflex during normal use.

Figure 28:
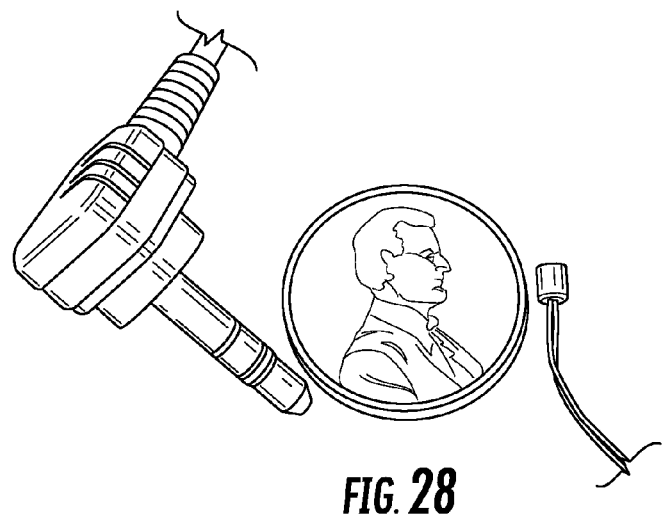
FIG. 28 is an image showing a probe microphone sold by Knowles
Figure 54:
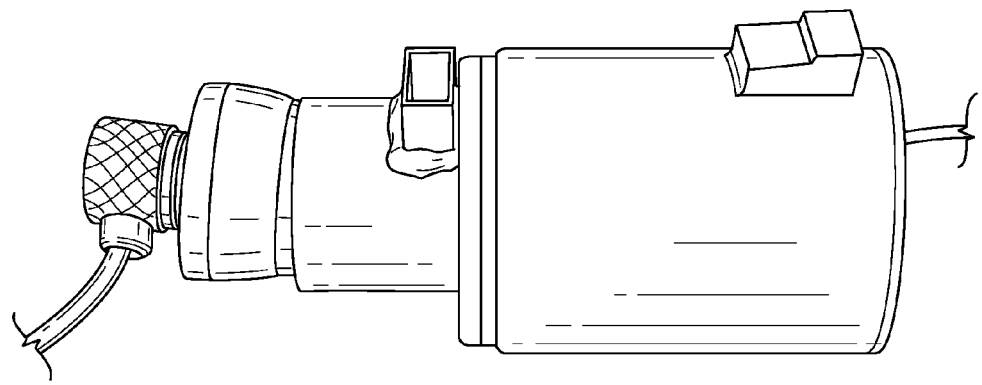
FIG. 54 is an image of a coupler with an inserted earbud.
Figure 29:
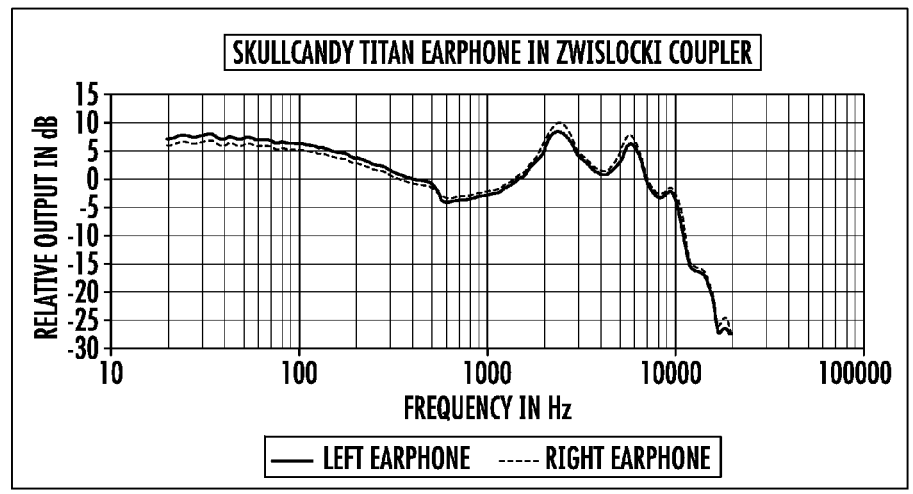
FIG. 29 is a graph showing data results of the set-up illustrated in FIG. 27(*b*)
Figure 30:
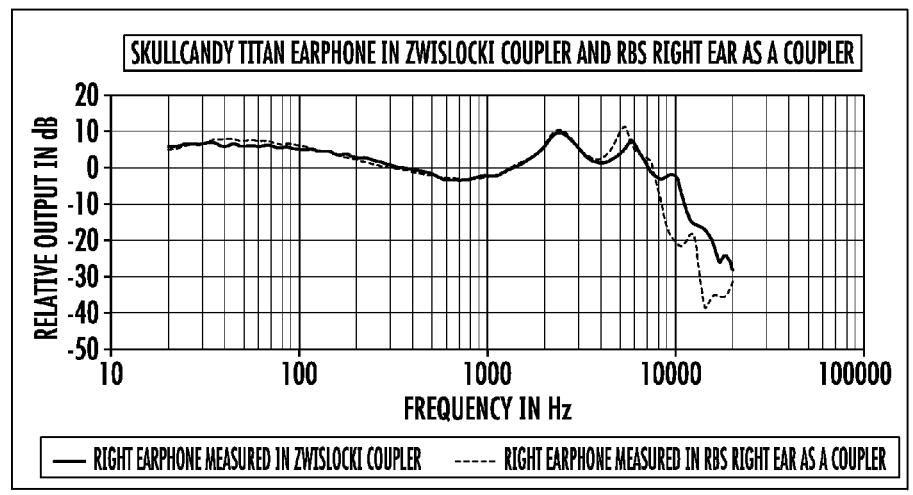
FIG. 30 is a graph showing data results of the set-up illustrated in FIG. 27(*b*) vs. the set up in FIG. 27(*c*)
Figure 31A:
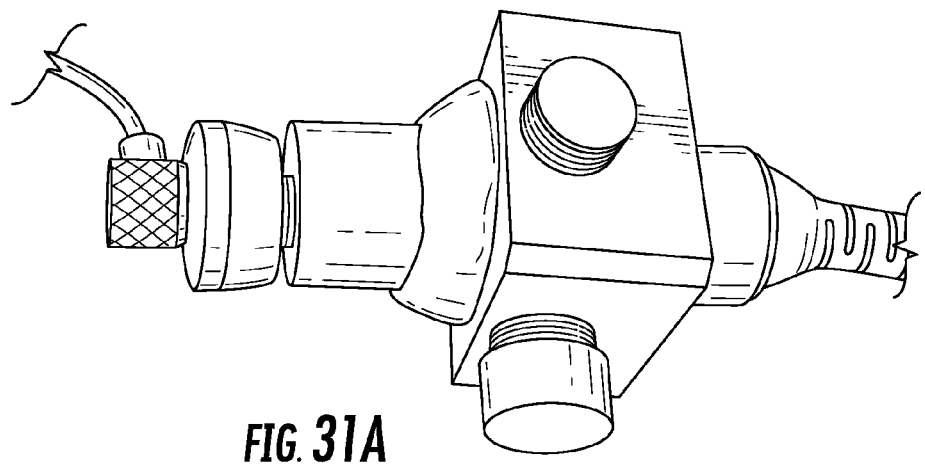
FIG. 31(*a, b*) are images of a ear-tip in a Zwislocki coupler, unsealed and sealed, respectively.
Figure 31B:
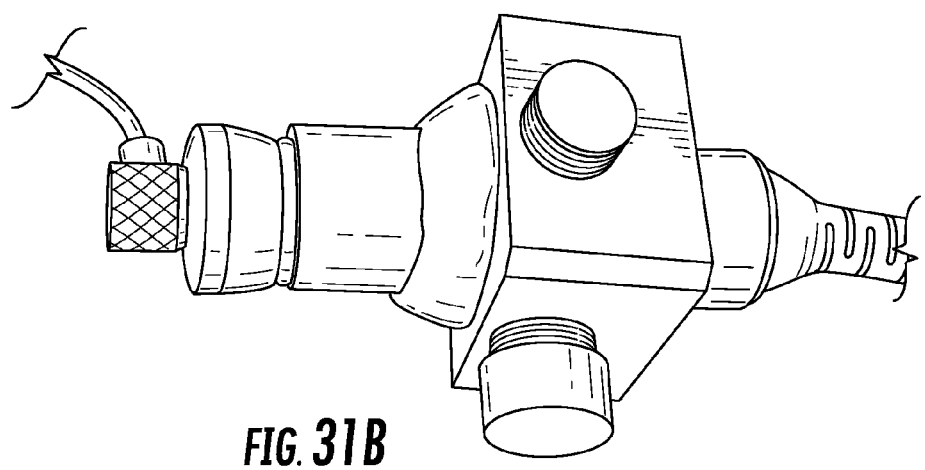
Figure 32A:
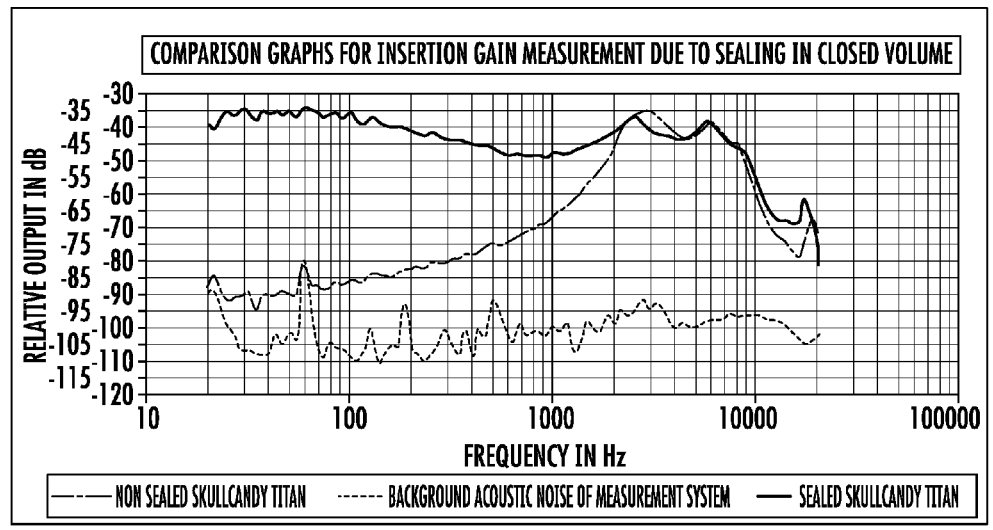
FIGS. 32(*a-c*) are graphs showing data results of the set-ups illustrated in FIG. 31*a,b;*
Figure 32B:
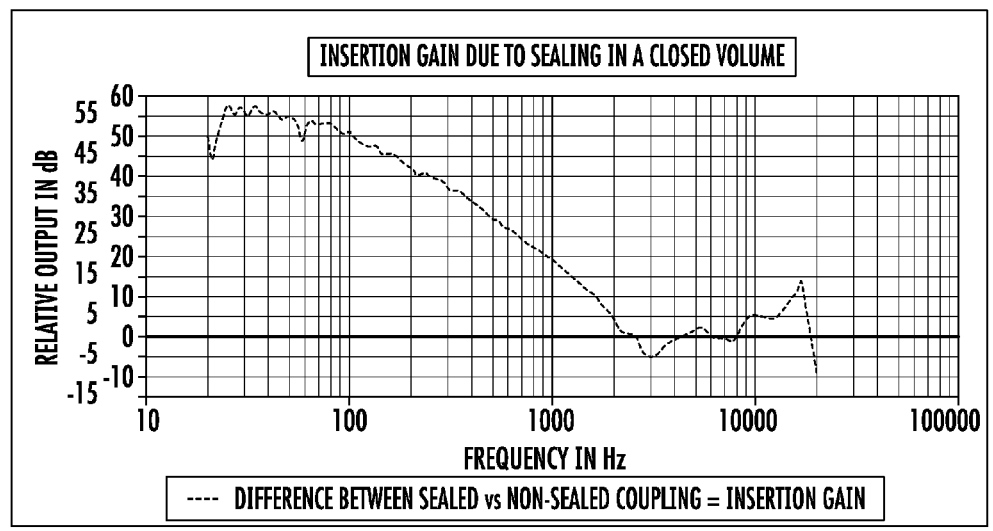
Figure 32C:
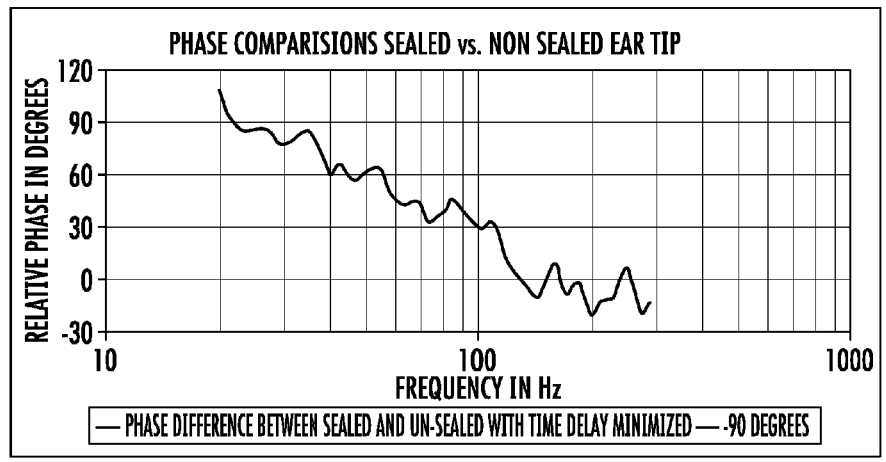
Figure 33:
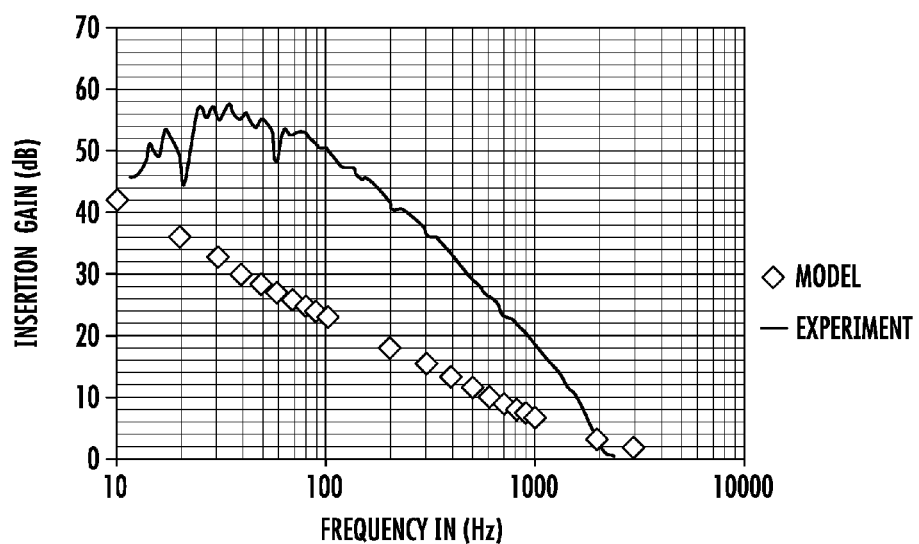
FIG. 33 is a graph comparing the experimental data to the model for determining insertion gain.
Figure 34:
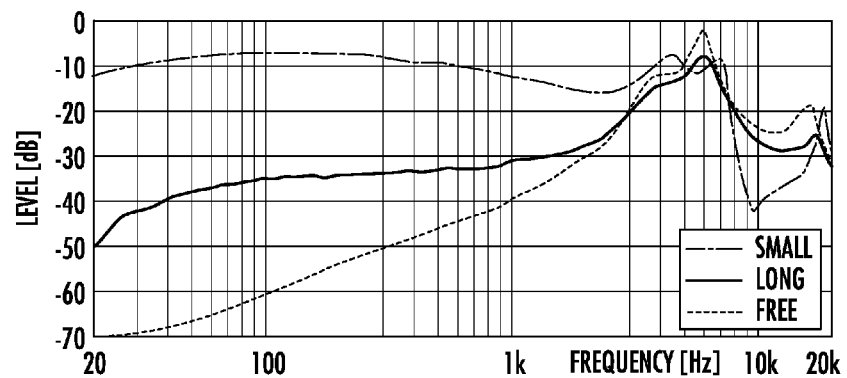
FIG. 34 is a graph reproduced from "Modeling of External Ear Acoustics for Insert Headphone Usage" *J Audio Eng. Soc.*, Vol. 58, No. 4, 2010, pp. 269-281.
Figure 35:
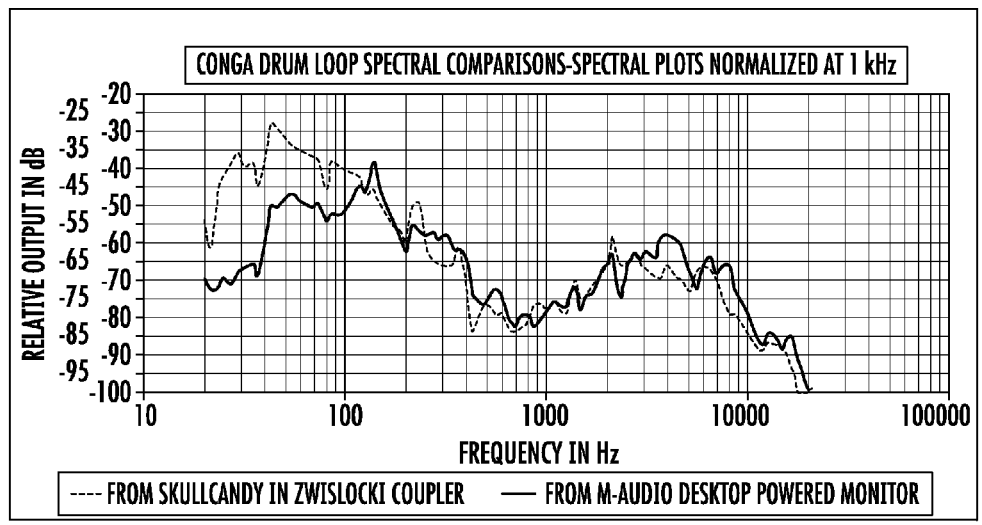
FIG. 35 is a graph showing relative SPL for a "Conga Drum" loop measured by the apparatus of FIG. 31*b* and a open air desktop speaker.
Figure 36:
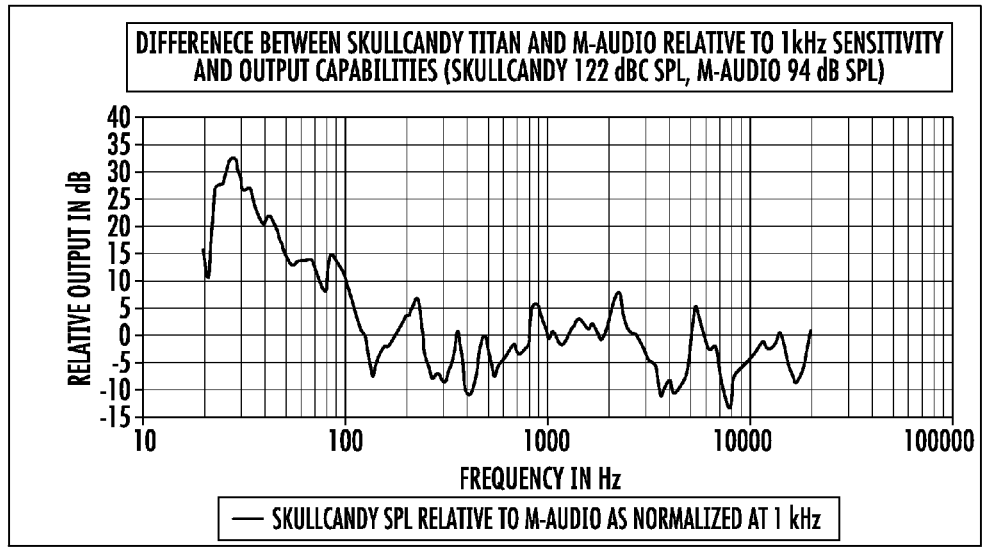
FIG. 36 is a graph showing a difference between the two apparatus charted in FIG. 35.
Figure 37:
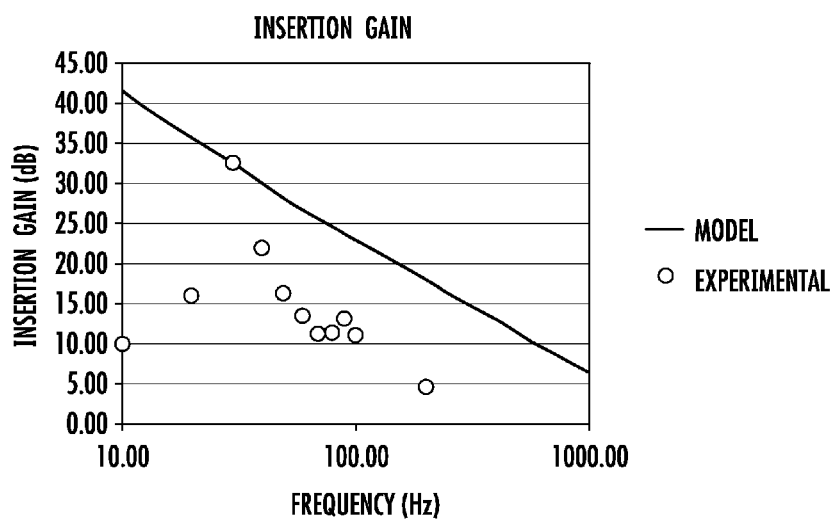
FIG. 37 is a graph showing model vs. experimental data for insertion gain at a range of frequencies.
Figure 38:
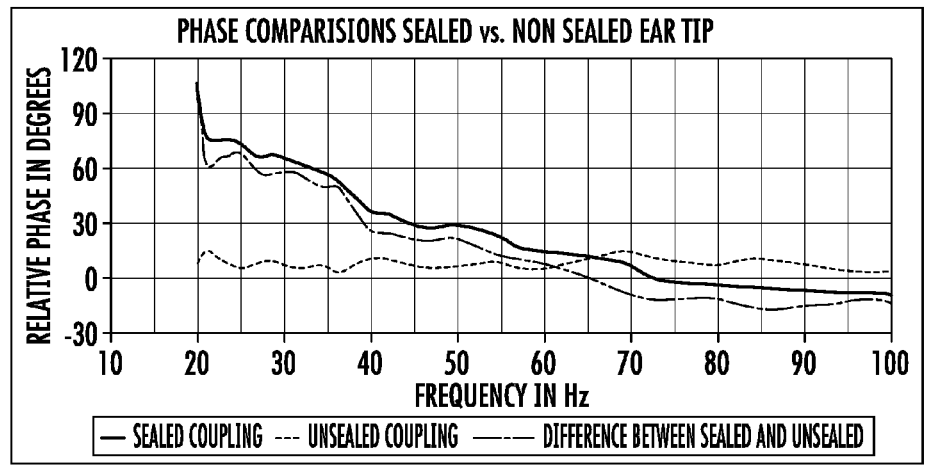
FIG. 38 is graph comparing relative phase in degrees of sealed and non-sealed couplings.
Figure 39:
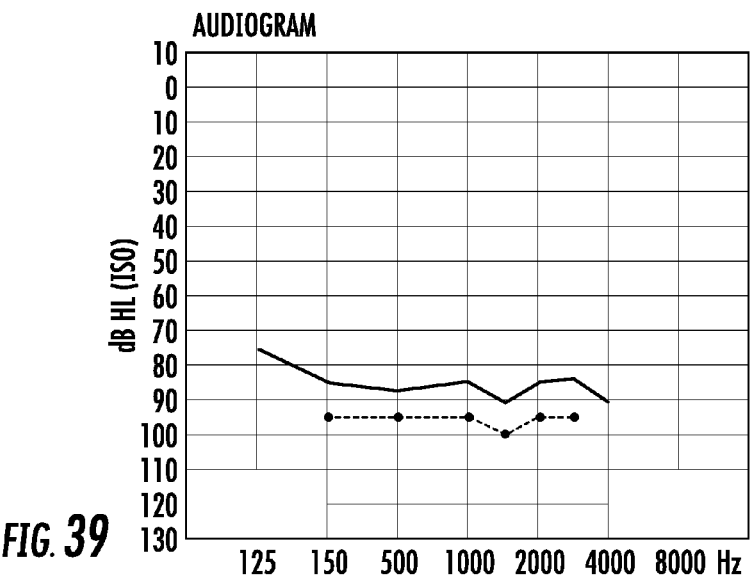
FIG. 39 is graph reproduced from "Stapedius Reflex Test, Brainstem Audiometry and Opto-Vestibular Tests in Diagnosis of Acoustic Neurinomas" *Scand. Audiol.*, 12: 3-9, 1983.
Figure 40:
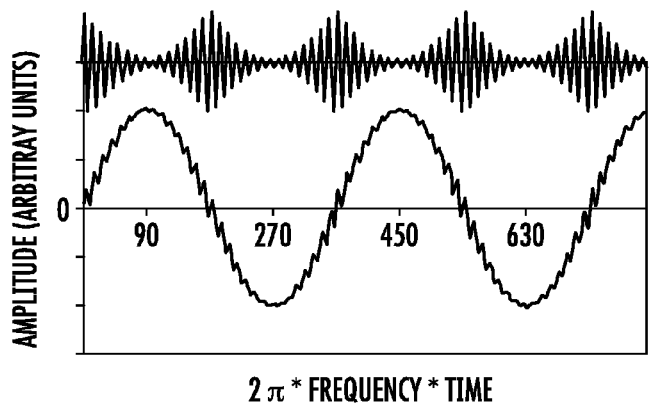
FIG. 40 is a graph illustrating a potential distortion from large over-excursions of the tympanic membrane.
Figure 50B:
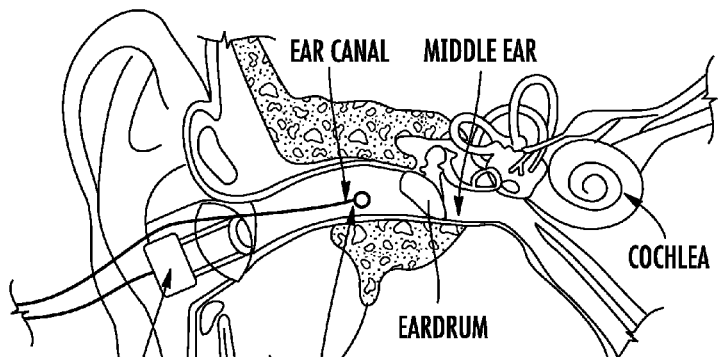
FIG. 50*b* is an image showing modification of the device shown in FIG. 50*a;*
Figure 51:
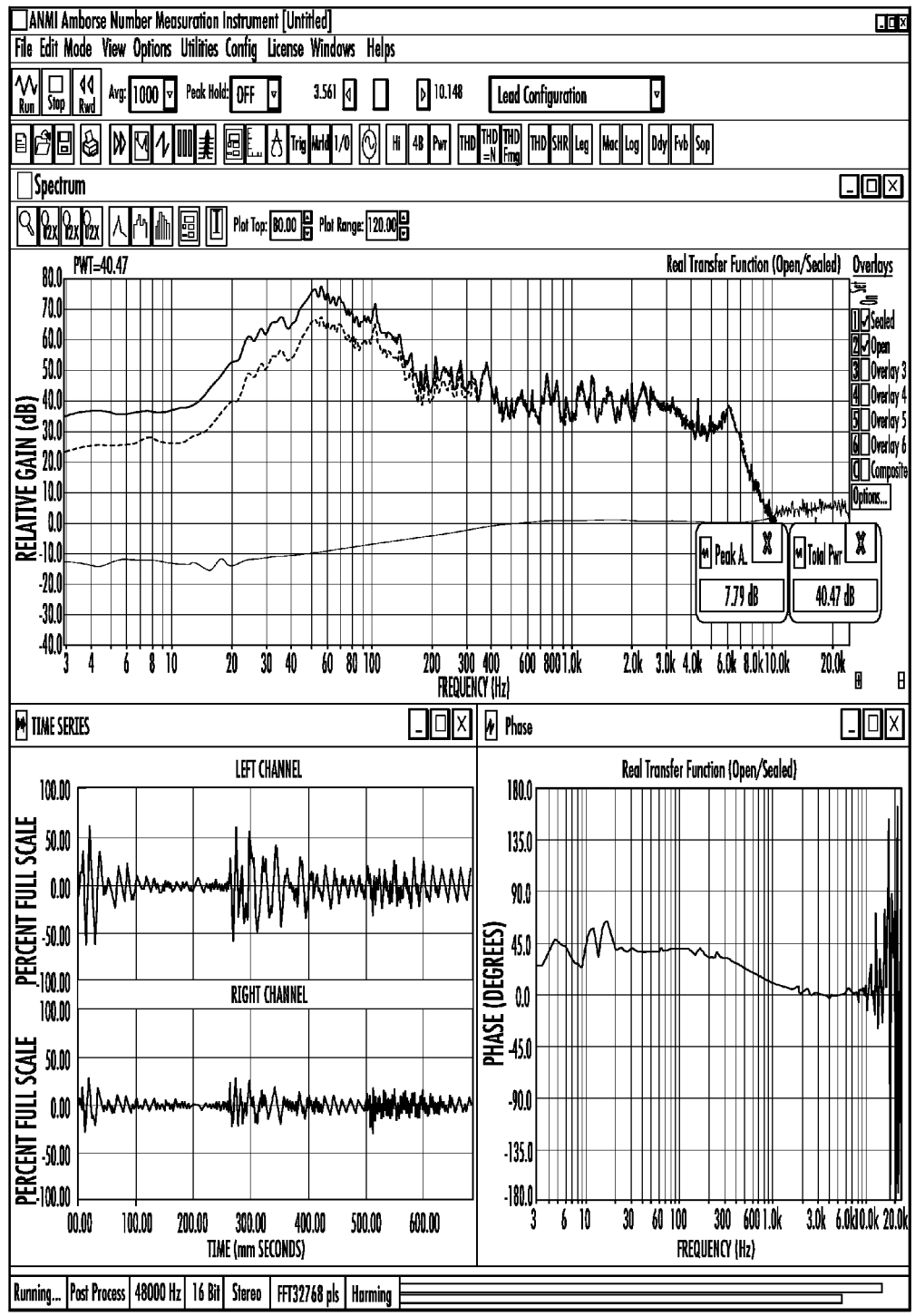
FIG. 51 is a screen shot showing a graph from a software test on oscillating static pressure.
Figure 52:
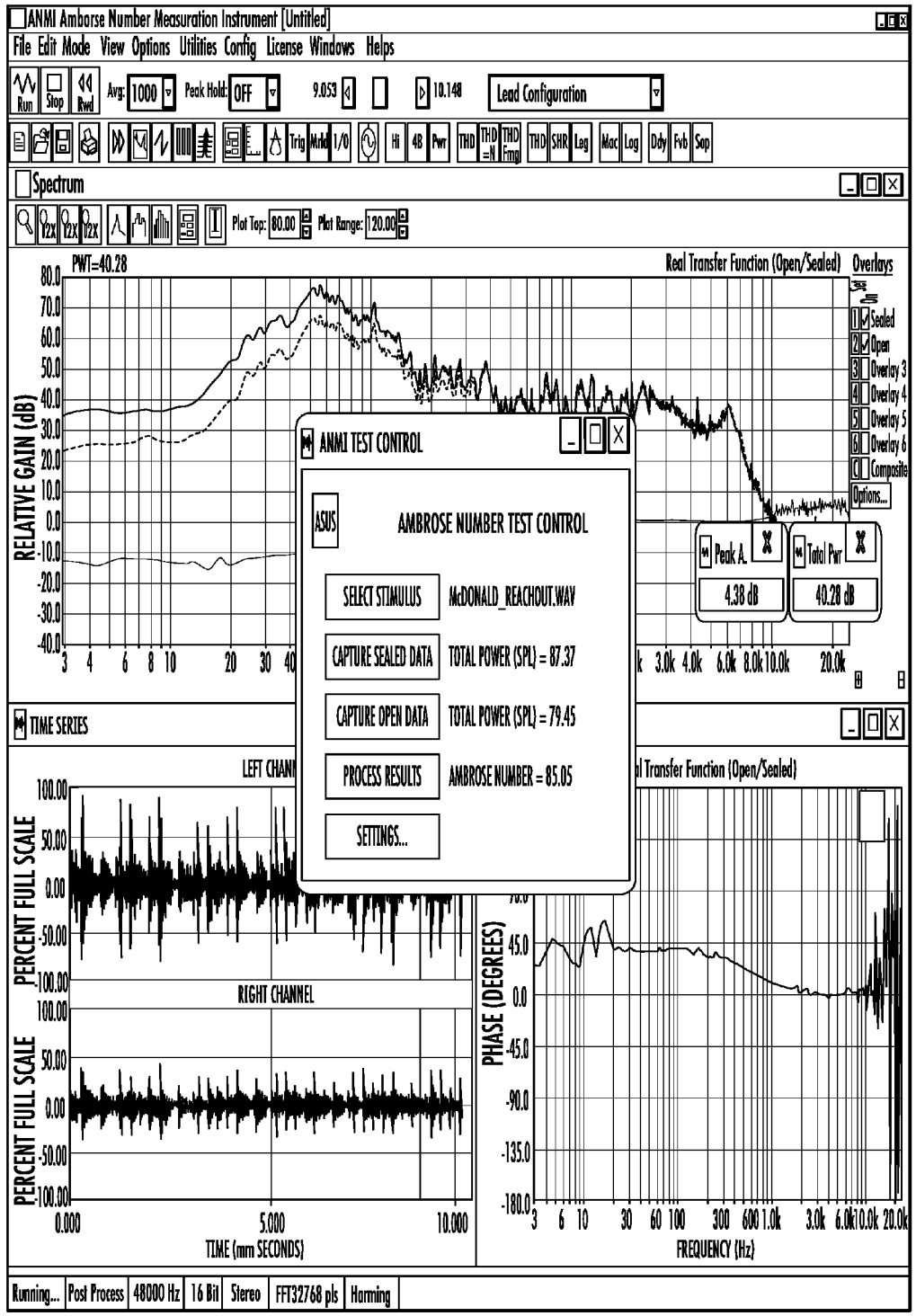
FIG. 52 is a screen shot from software showing the "Ambrose number" calculated.

In order to do a realistic test of real in-ear devices, the schematic is modified, as shown in FIG. 50b. The ear seal and the speaker of FIG. 50a are replaced by an insert headphone or hearing aid to be tested (such as the Skullcandy™ used above). This allows removal of the long tube to the speaker in FIG. 50a. The external microphone and tube leading to it are replaced by an insert probe microphone of the type shown in FIG. 28. This microphone can be inserted in the ear canal during testing, and its wire connection can be threaded through the ear seal without breaking the seal. The source of pressure in FIG. 50a is replaced by the static pressure induced in the sealed ear canal by the speaker of the device to be tested. The elimination of all the tubes running through the ear seal to external devices dramatically decreases the size of the trapped volume and allows realistic testing of the influence of effects such as oscillating static pressure and trapped volume insertion gain on the triggering of the stapedius reflex.

The procedure to do a reflex tympanometry test on real headphones or hearing aids, using the layout of FIG. 50b, can be the same or similar as the usual diagnostic procedure. In this case a probe tone is used to measure the impedance of the tympanic membrane to detect stiffening due to the stapedius reflex, while another louder tone, at a different frequency is used to induce the stapedius reflex.

Alternatively, one can do a test with the device of FIG. 50b to see whether listening to music or other audio material with the device to be tested (insert headphones, hearing aids, etc.) induces the stapedius reflex. This is done by taking a piece of audio program material (music, etc.) and using a notch filter to remove a specific band of frequencies, around the frequency of the probe tone to be used for tympanometry, from this audio program. Then the tympanometry test is performed using the audio program material played at different volumes. The test tone frequency, which is not interfered with by the audio program, is simultaneously used to measure the impedance of the tympanic membrane to detect the onset of the stapedius reflex, as the SPL from the audio material is increased.

The invention of FIG. 50b can be used to test for the threshold of the stapedius reflex when fitting hearing devices and hearing aids to patients. It can be performed using the actual device being fitted (rather than the standard tympanometry earpiece) because this allows the real trapped volume effects including TVIG and triggering of the stapedius reflex to be tested for real listening conditions with the actual device. The invention of FIG. 50b may be used to properly select and proscribe an ear-tip with sealed vents, an ADEL bubble ear tip, or any of the other embodiments disclosed in this application, to prevent TVIG and the stapedius reflex.

It should be emphasized that the above-described embodiments of the present invention, particularly, any "preferred" embodiments, are possible examples of implementations merely set forth for a clear understanding of the principles for the invention. Many variations and modifications may be made to the above-described embodiment(s) of the invention without substantially departing from the spirit and principles of the invention. All such modifications are intended to be included herein within the scope of this disclosure and the present invention, and protected by the following claims.

By way of summary, this specification has described a number of audio devices for transmitting sound. These audio devices include in-ear insertion tips, for example ear buds, with an enclosure having a sound transducer and opened at its other end into the ear canal toward the tympanic membrane. These audio devices also include an over-ear headphone which has an outer portion which fits snuggly against the side of the head and forms an enclosure which has a sound transducer and is opened toward the tympanic membrane. Another included audio device includes hearing aids which have an enclosure extending from a sound transducer and is opened toward the tympanic membrane.

All of these devices have in common that they can be open to the ambient surroundings, in which case pressure does not build-up in the ear canal so there are no detrimental effects of pneumatic pressures. For example, if ear buds are not fully inserted into the ear canal, or if over-ear headphones do not cover the ear canal sufficiently to create pressure therein, or hearing aids have an open-ear architecture, the ears will be at ambient pressure with no harmful effects of pneumatic pressures. Conversely, any one of these audio devices could be constructed or manipulated to substantially seal the ear canal. For example ear buds and hearing aids can be pushed slightly into the ear canal or be constructed to have an ear canal sealing member. Over-ear headphones may have an outer portion which tightly engages the side of the head.

The term "substantially seal" or "substantially trapped volume" means the degree of sealing, whether by manual movement of the audio device or by the use of a specially constructed seal, when harmful pneumatic pressures are created and impinge on the tympanic membrane.

The matter set forth in the foregoing description and accompanying drawings is offered by way of illustration only and not as a limitation. While particular embodiments have been shown and described, it will be apparent to those skilled in the art that changes and modifications may be made without departing from the broader aspects of applicants' contribution. The actual scope of the protection sought is intended to be defined in the following claims when viewed in their proper perspective based on the prior art.

What is claimed is:

1. An in-ear audio device comprising:
an enclosure having a sound transducer and open toward the tympanic membrane,
a seal which substantially seals the ear canal to form a substantially trapped volume in the enclosure and the ear canal up to the tympanic membrane, and
an alleviating means, which comprises a passageway from the substantially trapped volume to an unsealed space at ambient pressure, and a flexible compliant member blocking the passageway, for alleviating the effects of alternating or changing pneumatic pressures in the substantially trapped volume, when sound is transmitted from the sound transducer through the substantially trapped volume to the tympanic membrane, by partially or fully alleviating alternating or changing pneumatic pressures and allowing them to remain as normal sound waves.

2. An in-ear audio device according to claim 1, wherein the compliant member bows in and out in the course of alleviating the alternating or changing pneumatic pressures.

3. An in-ear audio device according to claim 1, wherein the in-ear audio device is an insert headphone tip comprising an elongated enclosure and a seal located on the outside of the enclosure which seals the ear canal.

4. An in-ear audio device according to claim 3, wherein the passageway and its compliant member are located in a sidewall of the enclosure.

5. An in-ear audio device according to claim 4, wherein there are a plurality of passageways and their respective compliant members in the sidewall.

6. An in-ear audio device according to claim 5, wherein the enclosure is an elongated tube, and the plurality of passageways and their respective compliant members are arranged either circumferentially about the exterior of the enclosure or longitudinally along the enclosure.

7. An in-ear audio device according to claim 1, wherein the compliant member comprises a sleeve which fits over the enclosure and covers all of the passageways.

8. An in-ear audio device according to claim 1, wherein the compliant member is made of a polymeric material or a lightweight metal or metal foil combined with a polymeric membrane.

9. An in-ear audio device according to claim 1, wherein the compliant member is made of ePTFE.

10. An in-ear audio device according to claim 1, including a tip extending out from the end of the enclosure and the passageway and compliant member are formed on the ear tip.

11. An in-ear audio device according to claim 1, wherein the passageway and compliant member are molded as a single piece of polymeric material.

12. An in-ear audio device according to claim 1, including a sleeve covering the passageway and its compliant member, which sleeve is movable on the enclosure to adjust the area of the passageway and its compliant member exposed to the unsealed space.

13. An in-ear audio device according to claim 1, wherein the compliant member comprises the surface of a bubble located in the passageway.

14. An in-ear audio device according to claim 1, wherein the audio device is a hearing aid.

15. An in-ear audio device according to claim 14, wherein the hearing aid has an ear tip, and the compliant member is in the ear tip.

16. An in-ear audio device according to claim 1, including a case surrounding the enclosure, and the passageway from the trapped volume passes through the casing.

17. An in-ear audio device according to claim 16, wherein the passageway passes through an outer circumferential part of the case.

18. An in-ear audio device according to claim 16, wherein the case has a front facing the tympanic membrane, and wherein the passageway passes through the front of the case.

19. An over-ear audio device comprising:
an enclosure having a sound transducer and open toward the tympanic membrane,
wherein the enclosure includes an outer portion which fits snuggly against the user's head outwardly of the ear canal and substantially seals the ear canal to form a substantially trapped volume from the outer portion to the tympanic membrane,
and an alleviating means, which comprises a passageway from the substantially trapped volume to an unsealed space at ambient pressure, and a flexible compliant member blocking the passageway, for alleviating the effects of alternating or changing pneumatic pressures in the substantially trapped volume when sound is transmitted from the sound transducer through the substantially trapped volume to the tympanic membrane, by partially or fully alleviating alternating or changing pneumatic pressures and allowing them to remain as normal sound waves.

20. An over-ear audio device according to claim 19, wherein the passageway and its compliant member extend from the trapped volume through the outer portion to the unsealed space.

21. An over-ear audio device according to claim 19, wherein the compliant member comprises a membrane.

22. An over-ear audio device according to claim 19, wherein the compliant member comprises a bubble located within its passageway.

23. An over-ear audio device according to claim 19, including a plurality of passageways with respective compliant members.

24. An over-ear audio device according to claim 19, including an enclosure wall supporting the outer portion, and the passageway passes through the wall.

25. An over-ear audio device according to claim 19, wherein the cross sectional size of the passageway is adjustable.

26. A method of reducing the sound pressure level experienced in a substantially trapped volume in a substantially sealed ear canal of a user of an audio device which transmits pressure and acoustic waves, comprising the step of alleviating the effects of alternating or changing pneumatic pressures in the substantially trapped volume by partially or fully alleviating alternating or changing pneumatic pressures and allowing them to remain as normal sound waves by having the substantially trapped volume communicate with a passageway extending from the substantially trapped volume to an unsealed space at ambient pressure, with a flexible compliant member blocking the passageway.

27. The method of claim 26, wherein the audio device is an in-ear audio device having an enclosure, in which the substantially trapped volume extends from a transducer to the tympanic membrane.

28. The method of claim 26, wherein during the alleviating step the compliant member bows in and out.

29. The method of claim 27, wherein the enclosure is elongated and the passageway and its compliant member are located in a sidewall of the enclosure.

30. The method of claim 29, including a plurality of passageways and respective compliant members.

31. The method of claim 26, wherein the compliant member is made of a polymeric material or a lightweight metal or metal foil combined with a polymeric membrane.

32. The method of claim 26, wherein the compliant member is made of ePTFE.

33. The method of claim 26, wherein the compliant member is a bubble located within the passageway.

34. The method of claim 27, wherein the compliant member is a sleeve encircling the enclosure and all passageways therethrough.

35. The method of claim 26, wherein a portion of the cross section of the passageway and its compliant member exposed to an unsealed space at ambient pressure is adjustable.

36. The method of claim 27, including a case surrounding the enclosure, and the passageway from the trapped volume passing through the case.

37. The method of claim 36, wherein the passageway passes through an outer circumferential part of the case.

38. The method of claim 36, wherein the case has a front facing the tympanic membrane, and wherein the passageway passes through the front of the case.

39. The method of claim 26, wherein the audio device is an over-ear audio device having an enclosure with a sound transducer and opened toward the tympanic membrane, and an outer portion engaging the side of the user's head outwardly of the ear to substantially seal the ear canal to create the substantially trapped volume from the outer portion to the tympanic membrane.

40. The method of claim 39, wherein the passageway and its compliant member extends from the substantially trapped volume through the outer portion to the unsealed space.

41. The method of claim 39, wherein the compliant member is a bubble.

42. The method of claim 39, wherein there are a plurality of passageways with respective compliant members.

43. The method of claim 27, including an enclosure wall supporting the outer portion, and the passageway passes through the wall.

44. A balanced armature transducer comprising:
a housing having a sidewall defining an interior volume,
a pliable membrane dividing the interior volume into a front volume and a back volume, and
a sound tube fluidly coupled to the front volume of the interior volume and an alleviating means, comprising a passageway extended from the front volume to an unsealed space at an ambient pressure and blocked by a flexible compliant member for alleviating the effects of alternating or changing pneumatic pressures within the interior volume when sound is transmitted through the balanced armature transducer by partially or fully alleviating alternating or changing pneumatic pressures and allowing them to remain as normal sound waves.

45. An in-ear audio device according to claim 1, wherein the compliant member is an inflatable bubble.

46. An in-ear audio device according to claim 45, wherein the inflatable bubble is an inflatable bag shaped bubble covering the end of the enclosure.

47. An in-ear audio device according to claim 45, wherein the inflatable bubble is a doughnut shaped bubble surrounding the enclosure.

48. An over-ear audio device according to claim 19, wherein the compliant member is an inflatable bubble.

49. An over-ear audio device according to claim 48, wherein the inflatable bubble is an inflatable bag shaped bubble covering the end of the enclosure.

50. An over-ear audio device according to claim 48, wherein the inflatable bubble is a doughnut shaped bubble surrounding the enclosure.

51. A method according to claim 26, wherein the audio device has a transducer, an enclosure leading from the transducer and wherein the alleviating step includes using an inflatable bubble mounted on the enclosure.

52. The method according to claim 51, wherein the inflatable bubble is an inflatable bag shaped bubble covering the end of the enclosure.

53. The method according to claim 51, wherein the inflatable bubble is a doughnut shaped bubble surrounding the enclosure.

54. A method of reducing the sound pressure level experienced in a substantially trapped volume in a substantially sealed ear canal from acoustic vibrations which enter the ear canal by transduction through the user's head and which cause transmission in the ear canal of pressure and acoustic waves, comprising the step of alleviating the effects of alternating or changing pneumatic pressures in the substantially trapped volume by partially or fully alleviating alternating or changing pneumatic pressures and allowing them to remain as normal sound waves by having the substantially trapped volume communicate with a passageway extending from the substantially trapped volume to an unsealed space at ambient pressure, with a flexible compliant member blocking the passageway.

55. A method according to claim 54, wherein the compliant member is an inflatable bubble.

* * * * *